(12) United States Patent
Crich et al.

(10) Patent No.: US 8,114,872 B2
(45) Date of Patent: Feb. 14, 2012

(54) TRIAZOLYL AMINOPYRIMIDINE COMPOUNDS

(75) Inventors: Joyce Z. Crich, Indianapolis, IN (US); Delu Jiang, Westfield, IN (US); Hong-Yu Li, Zionsville, IN (US); William Thomas McMillen, McCordsville, IN (US); Jason Scott Sawyer, Indianapolis, IN (US); Melissa Kate Slater, Carmel, IN (US); Yan Wang, Carmel, IN (US); James Robert Henry, Indianapolis, IN (US); Hong Hu, Chapel Hill, NC (US); Sachin Govindlal Maniar, Beech Grove, IN (US)

(73) Assignee: Eli Lilly and Company, Indianapolis, IN (US)

( * ) Notice: Subject to any disclaimer, the term of this patent is extended or adjusted under 35 U.S.C. 154(b) by 289 days.

(21) Appl. No.: 12/596,957

(22) PCT Filed: May 7, 2008

(86) PCT No.: PCT/US2008/062799
§ 371 (c)(1),
(2), (4) Date: Oct. 21, 2009

(87) PCT Pub. No.: WO2008/144222
PCT Pub. Date: Nov. 27, 2008

(65) Prior Publication Data
US 2010/0130466 A1    May 27, 2010

Related U.S. Application Data

(60) Provisional application No. 60/938,333, filed on May 16, 2007.

(51) Int. Cl.
*C07D 409/14* (2006.01)
*A61K 31/506* (2006.01)

(52) U.S. Cl. ............... 514/235.8; 514/252.18; 514/275; 544/122; 544/295; 544/331

(58) Field of Classification Search .............. 544/122, 544/295, 331; 514/235.8, 252.18, 275
See application file for complete search history.

(56) References Cited

FOREIGN PATENT DOCUMENTS

| WO | WO89/07599 | 8/1989 |
|---|---|---|
| WO | WO2004063192 | 7/2004 |
| WO | WO2004089913 | 10/2004 |
| WO | WO2006066172 | 6/2006 |
| WO | WO2007092095 | 8/2007 |
| WO | WO2007117465 | 10/2007 |
| WO | WO2008076704 | 6/2008 |
| WO | WO2008144222 | 11/2008 |
| WO | WO2008144223 | 11/2008 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20$^{th}$ Edition, vol. 1, pp. 1004-1010, 1996.*
Strebhardt, Multifaceted polo-like kinases: drug targets and antitargets for cancer therapy, Nature Reviews, vol. 9, Aug. 2010, pp. 643-660.*

* cited by examiner

*Primary Examiner* — Deepak Rao
(74) *Attorney, Agent, or Firm* — Tina M. Tucker

(57) ABSTRACT

The present invention provides triazolyl aminopyrimidine compounds useful in the treatment of cancer.

9 Claims, No Drawings

TRIAZOLYL AMINOPYRIMIDINE COMPOUNDS

This application claims the benefit under 35 U.S.C. §371 of International Application No. PCT/US2008/06279 filed May 7, 2008 which claims benefit under 35 U.S.C. §119(e) of U.S. Ser. No. 60/938,333 filed May 16, 2007.

Plk1 belongs to a small family of protein kinases characterized by a phosphoserine/threonine binding domain known as the polo box domain. Plk1 plays a central role in the regulation of the cell cycle. Among other functions, Plk1 is thought to regulate initiation, progression, and exit from mitosis, the stage when cancer cells divide. Consequently, blocking Plk1 in cancer cells prevents their division or mitosis.

Potent anticancer agents have been identified that interfere with mitosis such as the vinca alkaloids (NAVELBINE®), taxoids (TAXOTERE®) and topoisomerase II inhibitors (ADRIAMYCIN®). VELCADE® is an antineoplastic agent that inhibits the 26S proteosome. However, these drugs cause considerable side effects upon normal, non-dividing cells. Mk inhibitors specifically target dividing cells and may be able to avoid the undesirable toxicities.

Inhibitors of Plk1 are known in the art. See for example, WO 06/066172. Additionally, WO 06/021548 discloses certain dihydropteridinone analogs (e.g., BI-2536) as inhibitors of Plk1. Currently, BI-2536 is in phase II clinical trials but has high clearance (CL>1000 mL/min) and is dose limited by myelosupression in man. There is still a need for further compounds that inhibit Plk1 which possess improved potency or pharmacokinetic properties.

The present invention provides novel triazolyl aminopyrimidine compounds believed to have clinical use for treatment of cancer through inhibiting Plk1. Certain of these compounds are believed to have improved potency over compounds disclosed in WO 06/066172. Additionally, certain of the compounds of the present invention are believed to have improved pharmacokinetic properties, for example, clearance, over BI-2536. Further, due to the oral bioavailability of the compounds of the present invention that were tested, it is believed that certain of these compounds could be dosed orally.

The present invention provides compounds of Formula I:

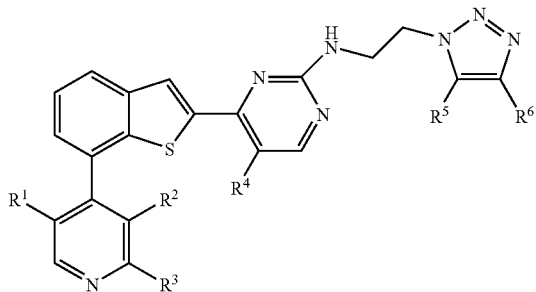

wherein:
$R^1$ is hydrogen, methyl, cyclopropyl, cyclopropylamino ($C_1$-$C_2$ alkyl), fluoro, ethoxy, hydroxy, 1-(hydroxy)ethyl, 2-(hydroxy)($C_2$-$C_3$ alkoxy), 2-(hydroxy)ethoxymethyl, 1-(chloro)ethyl, 1-((2-fluoro)ethylamino)ethyl, 2-(methylamino)ethoxy, (2-hydroxyethyl)amino, (2-hydroxyethyl)amino($C_1$-$C_2$ alkyl), amino, amino($C_1$-$C_4$ alkyl), amino($C_2$-$C_3$ alkoxy), aminocarbonylmethyl, (1-methyl)-(1-aminocarbonyl)ethyl, ($C_1$-$C_3$ alkyl)amino($C_1$-$C_2$ alkyl), methoxyethylamino, N—($C_1$-$C_3$ alkyl)-N-methyl-amino ($C_1$-$C_2$ alkyl), pyrrolidin-1-yl-methyl, 3-(dimethylamino)-pyrrolidin-1-yl-methyl, 3-(pyrid-3-yl)-pyrrolidin-1-yl-methyl, 3-(amino)pyrrolidin-1-yl-methyl, 3-(methylamino) pyrrolidin-1-yl-methyl, (4,4-dimethyloxalidin-3-yl)methyl, [N-(2-hydroxy)ethyl-N-methyl]-aminomethyl, (azetidin-1-yl)methyl, piperidin-1-yl-methyl, 4-(methoxy)piperidin-1-yl-methyl, 4-(hydroxy)piperidin-1-yl-methyl, 4-(hydroxymethyl)piperidin-1-yl-methyl, piperazin-1-yl-($C_1$-$C_2$ alkyl), 4-(methyl)piperazin-1-yl-methyl, 3,5-(dimethyl)piperazin-1-yl-methyl, or morpholin-4-yl-methyl;
$R^2$ is hydrogen;
$R^3$ is hydrogen, methyl, fluoro, or chloro, or $R^3$ is amino and together with $R^2$ forms a pyrrolyl ring fused to the pyridine;
$R^4$ is hydrogen, methyl, fluoro, or chloro;
$R^5$ is hydrogen or hydroxymethyl; and
$R^6$ is hydrogen or methyl; or
a pharmaceutically acceptable salt thereof.

The present invention provides a method of treating cancer selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers in a mammal comprising administering to a mammal in need of such treatment an effective amount of a compound of Formula I or a pharmaceutically acceptable salt thereof.

The present invention also provides a pharmaceutical composition comprising a compound of Formula I or a pharmaceutically acceptable salt thereof, in combination with a pharmaceutically acceptable excipient, carrier, or diluent.

This invention also provides a compound of Formula I or a pharmaceutically acceptable salt thereof for use as a medicament. Additionally, this invention provides use of a compound of Formula I or a pharmaceutically acceptable salt thereof in the manufacture of a medicament for treating cancer. In particular these cancers are selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers. Furthermore, this invention provides a pharmaceutical composition for treating cancer selected from the group consisting of non-small cell lung, oropharyngeal, esophageal, gastric, melanoma, epidermoid carcinoma of the skin, breast, ovarian, endometrial, colorectal, neuroglioma, glioblastoma, thyroid carcinoma, cervical, pancreatic, prostate, hepatoblastoma and non-Hodgkin lymphoma cancers comprising a compound of Formula I or a pharmaceutically acceptable salt thereof as an active ingredient.

The present invention also provides compounds of the Formula:

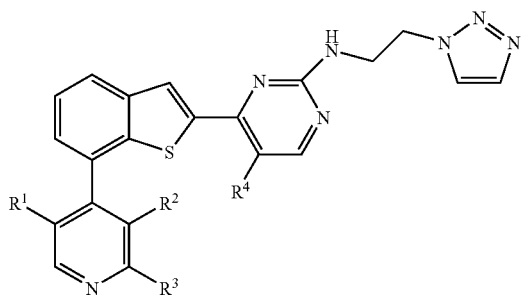

wherein:

R$^1$ is hydrogen, methyl, cyclopropyl, cyclopropylaminomethyl, halo, ethoxy, hydroxy, 1-(hydroxy)ethyl, 2-(hydroxy)ethoxy, amino, amino(C$_1$-C$_4$ alkyl), (C$_1$-C$_3$ alkyl)aminomethyl, N—(C$_1$-C$_3$ alkyl)-N-methyl-aminomethyl, aminocarbonylmethyl, pyrrolidin-1-yl-methyl, 3-(dimethylamino)pyrrolidin-1-yl-methyl, 3-(pyrid-3-yl)-pyrrolidin-1-yl-methyl, 3-(amino)pyrrolidin-1-yl-methyl, 2-(hydroxy)ethoxymethyl, (4,4-dimethyloxalidin-3-yl)methyl, [N-(2-hydroxy)ethyl-N-methyl]-aminomethyl, (azetidin-1-yl)methyl, 4-(methoxy)piperidin-1-yl-methyl, 4-(hydroxy)piperidin-1-yl-methyl, 4-(hydroxymethyl)piperidin-1-yl-methyl, piperazin-1-yl-methyl, 4-(methyl)piperazin-1-yl-methyl, 3,5-(dimethyl)piperazin-1-yl-methyl, or morpholin-4-yl-methyl;

R$^2$ is hydrogen;

R$^3$ is hydrogen or halo, or R$^3$ is amino and together with R$^2$ forms a pyrrolyl ring fused to the pyridine; and R$^4$ is hydrogen or halo; or a pharmaceutically acceptable salt thereof.

The general chemical terms used in the formulae above have their usual meanings. For example, the term "(C$_1$-C$_3$ alkyl)" means methyl, ethyl, propyl, and isopropyl. The term "(C$_1$-C$_2$ alkyl)" is included within the term "(C$_1$-C$_3$ alkyl)" and means methyl and ethyl. The term "(C$_2$-C$_3$ alkoxy)" means ethoxy, propoxy, and isopropoxy.

The term "halo" means fluoro, chloro, bromo, and iodo.

When a substituent is attached through an alkyl group such as ethyl, n-propyl, isopropyl, n-butyl, isobutyl, sec-butyl, or tert-butyl, for example, in the terms "amino(C$_1$-C$_4$ alkyl)" or "(C$_1$-C$_2$ alkyl)amino(C$_1$-C$_2$ alkyl)", the attachment to the substituent (for example, amino) may be through any carbon of the alkyl or alkoxy. For example, It will be understood by the skilled reader that most or all of the compounds of the present invention are capable of forming salts. The compounds of the present invention are amines, and accordingly react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol 66, No. 1, January 1977.

Preferred are compounds of Formula I wherein:
a) R$^1$ is amino(C$_1$-C$_2$ alkyl);
b) R$^1$ is 1-(amino)ethyl;
c) R$^1$ is (C$_1$-C$_3$ alkyl)amino(C$_1$-C$_2$ alkyl);
d) R$^1$ is 1-(methylamino)ethyl;
e) R$^1$ is amino(C$_1$-C$_2$ alkyl) or (C$_1$-C$_3$ alkyl)amino(C$_1$-C$_2$ alkyl);
f) R$^2$ is hydrogen;
g) R$^3$ is hydrogen;
h) R$^3$ is fluoro;
i) R$^3$ is hydrogen or fluoro;
j) R$^4$ is fluoro;
k) R$^4$ is hydrogen;
l) R$^4$ is hydrogen and fluoro;
m) R$^5$ is hydrogen;
n) R$^6$ is hydrogen;
o) R$^1$ is cyclopropylamino(C$_1$-C$_2$ alkyl), 1-(hydroxy)ethyl, 2-(hydroxy)ethoxymethyl, 1-(chloro)ethyl, 1-((2-fluoro)ethylamino)ethyl, (2-hydroxyethyl)amino, (2-hydroxyethyl)amino(C$_1$-C$_2$ alkyl), amino(C$_1$-C$_4$ alkyl), aminocarbonylmethyl, (1-methyl)-(1-aminocarbonyl)ethyl, (C$_1$-C$_3$ alkyl)ethyl, (C$_1$-C$_3$ alkyl)amino(C$_1$-C$_2$ alkyl), N—(C$_1$-C$_3$ alkyl)-N-methyl-amino(C$_1$-C$_2$ alkyl), pyrrolidin-1-yl-methyl, 3-(dimethylamino)pyrrolidin-1-yl-methyl, 3-(pyrid-3-yl)-pyrrolidin-1-yl-methyl, 3-(amino)pyrrolidin-1-yl-methyl, 3-(methylamino)pyrrolidin-1-yl-methyl, (4,4-dimethyloxalidin-3-yl)methyl, [N-(2-hydroxy)ethyl-N-methyl]-aminomethyl, (azetidin-1-yl)methyl, piperidin-1-yl-methyl, 4-(methoxy)piperidin-1-yl-methyl, 4-(hydroxy)piperidin-1-yl-methyl, 4-(hydroxymethyl)piperidin-1-yl-methyl, piperazin-1-yl-(C$_1$-C$_2$ alkyl), 4-(methyl)piperazin-1-yl-methyl, 3,5-(dimethyl)piperazin-1-yl-methyl, or morpholin-4-yl-methyl;

p) R$^1$ is amino(C$_1$-C$_4$ alkyl), (C$_1$-C$_3$ alkyl)amino(C$_1$-C$_2$ alkyl), N—(C$_1$-C$_3$ alkyl)-N-methyl-amino(C$_1$-C$_2$ alkyl), or morpholin-4-yl-methyl;

q)
R$^1$ is amino(C$_1$-C$_4$ alkyl), or (C$_1$-C$_3$ alkyl)amino(C$_1$-C$_2$ alkyl);
R$^3$ is hydrogen or fluoro;
R$^4$ is hydrogen or fluoro;
R$^5$ is hydrogen; and
R$^6$ is hydrogen;

r) R$^1$ is 1-(methylamino)ethyl, R$^3$ is fluoro and R$^4$ is hydrogen, R$^5$ is hydrogen, and R$^6$ is hydrogen;

s) R$^1$ is 1-aminoethyl, R$^3$ is fluoro and R$^4$ is fluoro, R$^5$ is hydrogen, and R$^6$ is hydrogen;

t) R$^1$ is 1-aminoethyl, R$^3$ is fluoro and R$^4$ is hydrogen, R$^5$ is hydrogen, and R$^6$ is hydrogen; and u) R$^1$ is 1-(methylamino)ethyl, R$^3$ is fluoro and R$^4$ is fluoro, R$^5$ is hydrogen, and R$^6$ is hydrogen.

The schemes together with the preparations and examples illustrate the synthesis of compounds of the present invention.

Compound 5 in Scheme I is prepared by a palladium (0) coupling reaction between either starting material 1 with 2, or starting material 3 with 4. A suitable palladium catalyst, such as tetrakis(triphenylphosphine)-palladium(0) or [1,1'-bis(diphenyl-phosphino)ferrocene]dichloropalladium(II) complex with DCM (1:1) [Pd(dppf)Cl$_2$]. Pd(dppf)Cl$_2$ is used in the presence of a base, such as sodium or potassium carbonate. The reactions are carried out in a solvent, such as tetrahydrofuran (THF), dioxane, and water, generally, at temperatures of from about 100° C. to 150° C. using an oil bath or a microwave reactor.

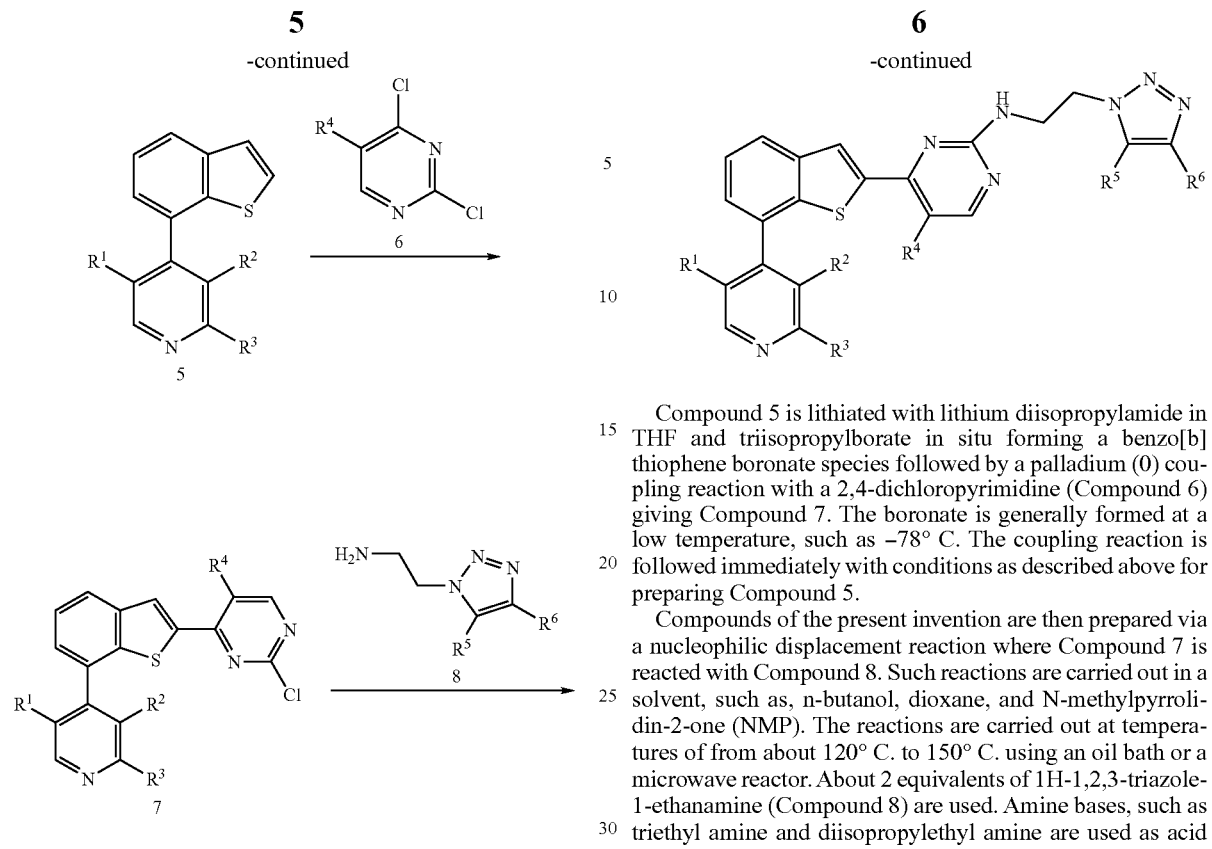

Compound 5 is lithiated with lithium diisopropylamide in THF and triisopropylborate in situ forming a benzo[b]thiophene boronate species followed by a palladium (0) coupling reaction with a 2,4-dichloropyrimidine (Compound 6) giving Compound 7. The boronate is generally formed at a low temperature, such as −78° C. The coupling reaction is followed immediately with conditions as described above for preparing Compound 5.

Compounds of the present invention are then prepared via a nucleophilic displacement reaction where Compound 7 is reacted with Compound 8. Such reactions are carried out in a solvent, such as, n-butanol, dioxane, and N-methylpyrrolidin-2-one (NMP). The reactions are carried out at temperatures of from about 120° C. to 150° C. using an oil bath or a microwave reactor. About 2 equivalents of 1H-1,2,3-triazole-1-ethanamine (Compound 8) are used. Amine bases, such as triethyl amine and diisopropylethyl amine are used as acid scavengers.

Scheme II

Alternately, compounds of the present invention can be prepared by the Suzuki reaction between starting materials 2 and 9 or 4 and 10 with conditions described above.

Since two coupling reactions are employed in the synthesis of compounds of the present invention, starting materials 9 and 10 of Scheme II represent a reverse coupling order by comparison with Scheme I.

The skilled artisan will appreciate that not all of the substituents in the compounds of the present invention will tolerate certain reaction conditions employed to synthesize the compounds. These moieties may be introduced at a convenient point in the synthesis, or may be protected and then deprotected as necessary or desired. The skilled artisan will appreciate that protecting groups may be introduced or removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3$^{rd}$ Ed., John Wiley and Sons, New York, Chapter 7 (1999). Some of the examples of the present invention are prepared from other examples of the present invention. Furthermore, the skilled artisan will appreciate that in many circumstances, the order in which the moieties are introduced is not critical. The particular order of steps required to produce the compounds of the present invention can be dependent upon the particular compound being synthesized, the starting compound, and the relative lability of the substituted moieties.

Some the compounds of the present invention contain asymmetric centers. In these instances, the enantiomers as well as the racemate are contemplated in the present invention. ChemDraw® version 10.0 was used in generating Example names.

PREPARATION 1

2-Benzo[b]thiophen-7-yl-4,4,5,5-tetramethyl-[1,3,2] dioxaborolane

Combine 7-bromo-benzo[b]thiophene (426 mg, 2 mmol), bis(pinacolato)diboron (756 mg, 3 mmol), Pd(dppf)Cl$_2$ (81 mg, 0.1 mmol), and potassium acetate (294 mg, 3 mmol) in dimethylsulfoxide (DMSO) (10 mL) in a flask. Bubble nitrogen through the mixture for 5 min. Seal the flask and put it into an oil bath and heat to 100° C. for 4 hours (h). Dilute the mixture with chloroform/isopropyl alcohol (IPA) (3/1). Wash the solution with saturated aqueous sodium chloride. Dry over sodium sulfate. Concentrate the solution in vacuo to a dark residue. Purify by column chromatography (hexane→20% ethyl acetate in hexane) to afford the title compound as a colorless solid (342 mg, 66%). MS (ES) m/z 261 [M+1]$^+$.

PREPARATION 2

Benzo[b]thiophene-7-boronic acid

Combine 7-bromobenzo[b]thiophene (300 g, 1.41 mmol) and tri-isopropylborate (403.6 g, 2.15 mmol) in anhydrous THF (4 L) in a 12-L Morton flask fitted with a mechanical stirrer and cool under nitrogen in a dry-ice/acetone bath to −70° C. Add n-butyl lithium (1.6 M in hexane, 714 g, 1.68 mmol) dropwise at such a rate as to keep the internal temperature less than −67.5° C. After the addition is complete allow the reaction mixture to stir at this temperature for 1 h. Remove the cooling bath and slowly add 4 L of water, which causes the temperature to rise to about −5° C. Next, add concentrated HCl (75 mL) until the pH of the solution is about pH=2. Allow the slurry to stir for 1 h. Add sufficient 5 N aqueous NaOH to adjust the pH of the mixture to about pH=12 and transfer to a 22-L bottom-drop funnel. Separate and save the lower aqueous layer. Dilute the upper organic layer with 4 L of methyl-tert-butyl ether and extract with 1 L of 5 N aqueous NaOH. Separate the aqueous layer, combine with the previous aqueous extract, and place back in the separatory funnel. Wash the aqueous layer with additional methyl-tert-butyl ether (4 L). Again, separate the aqueous layer and transfer to a 12-L, 3-neck round bottom flask fitted with a mechanical stirrer. Cool the solution to +5° C. with an ice-water bath. Add concentrated HCl slowly until the pH of the solution is about pH=2. Stir the mixture for 30 minutes (min) and then filter off the resulting solid. Rinse the solid on the funnel twice with 2 L of water and allow to air-dry for 30 min. Place the solid in a vacuum oven at 50° C. and dry under vacuum overnight. Slurry the dried solid with 2 L of n-heptane for 30 min to remove the yellow color. Again, filter the solid, air-dry for 30 min, and then vacuum-dry at 40° C. overnight to afford the title compound (188.8 g, 75%) as a white solid. $^1$H NMR (400 MHz, CD$_3$OD) δ 7.86 (d, J=8 Hz, 1H), 7.49-7.57 (m, 2H), 7.30-7.39 (m, 2H).

PREPARATION 3

5-Bromomethyl-2-fluoro-4-iodo-pyridine

In a flask, combine 2-fluoro-4-iodo-picoline (10.0 g, 42.2 mmol), N-bromosuccinimide (9.76 g, 54.8 mmol), 2,2'-azobisisobutyronitrile (3.46 g, 21.1 mmol) and dry CCl$_4$ (100 mL). Heat the mixture at 70° C. under nitrogen for 16 h. Cool to room temperature (RT). Dilute with dichloromethane (DCM) and wash with water and aqueous saturated sodium chloride. Separate the layers and dry the organic layer over magnesium sulfate. Concentrate in vacuo to give the crude product. Purify by column chromatography (1% to 15% ethyl acetate in hexane) to afford the title compound (8.27 g, 62%). MS (ES) m/z 315 [M+1]$^+$.

PREPARATION 4

(6-Fluoro-4-iodo-pyridin-3-yl)-acetonitrile

Combine trimethylsilyl cyanide (297 mg, 3.0 mmol) and tetrabutylammonium fluoride (785 mg, 3.0 mmol) in 20 mL of acetonitrile under nitrogen. Add 5-bromomethyl-2-fluoro-4-iodo-pyridine (0.63 g, 2.0 mmol) to the above solution. Stir the mixture for 2 h at RT. Dilute the mixture with chloroform/IPA (3/1). Wash the solution with water and subsequently with saturated aqueous sodium chloride. Dry it over sodium sulfate. Concentrate the solution in vacuo. Purify by column chromatography (5% methanol in DCM) to afford the title compound as a yellow, waxy solid (500 mg, 96%). MS (ES) m/z 263 [M+1]$^+$.

PREPARATION 5

2-(6-Fluoro-4-iodopyridin-3-yl)-2-methylpropanenitrile

Add sodium hydride (1.51 g, 62.9 mmol) to a solution of (6-fluoro-4-iodo-pyridin-3-yl)-acetonitrile (5.5 g, 20.9 mmol) in 10 mL of dimethyl formamide (DMF) at 0° C. Stir the mixture from 0° C. to RT for 30 min. Add methyl iodide (8.9 g, 63 mmol) and continue to stir the mixture at RT for another 30 min. Dilute the mixture with water and abstract into DCM. Dry the organic phase over sodium sulfate and concentrate in vacuo to give an oily residue. Purify the residue by flash column chromatography (FCC) (20% ethyl acetate in hexane) to give the title compound as a yellow solid (5 g, 82%). MS (ES) m/z 291 [M+1]⁺.

PREPARATION 6

2-(6-Fluoro-4-iodo-pyridin-3-yl)-acetamide

Combine (6-fluoro-4-iodo-pyridin-3-yl)-acetonitrile (360 mg, 1.37 mmol), hydrogen peroxide (10 g, 30%, 158 mmol), 18-crown ether (36 mg, 0.14 mmol), potassium carbonate (2 M, 10 mL, 20 mmol) and 10 mL of ethanol together to form a homogenous solution. Stir the mixture for 3 h. Dilute it with water. Extract the product into DCM. Purify the crude with FCC (10% methanol in DCM) to afford the title compound as a white solid (250 mg, 64%). MS (ES) m/z 281 [M+1]⁺.

Prepare the following intermediate using a procedure similar to the one for 2-(6-Fluoro-4-iodo-pyridin-3-yl)-acetamide:

| Prep | Compound Name | MS (ES) m/z [M + 1]⁺ |
|---|---|---|
| 7 | 2-(6-Fluoro-4-iodopyridin-3-yl)-2-methylpropanamide | 309 |

PREPARATION 8

1-(6-Fluoro-pyridin-3-yl)-ethanol

Add methylmagnesium bromide (3 M in ether, 12 mL, 36 mmol) at 0° C. under nitrogen to a solution of 6-fluoro-pyridine-3-carbaldehyde (3 g, 24 mmol) in THF (20 mL). Continue to stir the mixture overnight at RT. Quench the mixture with 1 N HCl, followed by basification with diluted ammonium hydroxide to ~pH 9. Extract the product with chloroform/IPA (3/1). Dry over sodium sulfate. Concentrate the solution in vacuo. Purify by column chromatography (10% methanol in DCM) to give the title compound as a colorless oil (2.3 g, 68%). MS (ES) m/z 142 [M+1]⁺.

PREPARATION 9

5-(1-Azido-ethyl)-2-fluoro-pyridine

To a 1-L flask kept cold in an ice bath, add triphenylphosphine (27.9 g, 106.3 mmol), 4,5-dichloro-3,6-dioxocyclohexa-1,4-diene-1,2-dicarbonitrile (24.12 g, 106.3 mmol). Add DCM slowly with stirring (150 mL). To the dark solution add tetra-N-butylammonium azide (30.23 g, 106.3 mmol) slowly, followed by 1-(6-fluoro-pyridin-3-yl)-ethanol (10 g, 70.85 mmol) dissolved in DCM (10 mL). Remove the flask from the ice bath and stir at RT for 1 h. Remove the solvent on a rotovap and purify by normal phase chromatography 5% to 20% ethyl acetate in hexanes to obtain the title compound as a colorless oil (7.75 g). GCMS m/z 166 [M]⁺.

PREPARATION 10

1-(6-Fluoro-pyridin-3-yl)-ethylamine

Hydrogenate 5-(1-azido-ethyl)-2-fluoro-pyridine (4.09 g, 24.59 mmol) under a 60 psi pressure in ethanol (200 mL) in the presence of PtO₂ (6% w/w). Filter the mixture after 4 h, remove the solvent on a rotovap, and dry the resulting oil under vacuum to obtain the title compound (3.15 g). GCMS m/z 140 [M]⁺.

PREPARATION 11

1-(6-Chloropyridin-3-yl)ethanol

Add sodium tetrahydroborate (1.01 g, 26.35 mmol) slowly to a solution of 1-(6-chloro-pyridin-3-yl)-ethanone (10 g, 64.27 mmol) in methanol (100 mL). Stir at RT for 15 min. Pour the reaction mixture into a beaker containing saturated NaHCO₃ (40 mL) and then extract between water (100 mL) and DCM (400 mL). Wash the organic layers with saturated aqueous sodium chloride, dry over sodium sulfate and concentrate. Purify by normal phase column chromatography (20% ethyl acetate in hexanes→70% ethyl acetate in hexanes) to afford the title compound (7 g, 69%). MS (ES) m/z 158 [M+1]⁺.

PREPARATION 12

2-Fluoro-5-(1-methoxymethoxy-ethyl)-pyridine

Add diisopropylethylamine and chloromethoxymethane to a solution of 1-(6-fluoro-pyridin-3-yl)-ethanol (3.0 g, 21.3 mmol) in DCM at 0° C. Continue to stir the mixture for 30 min at 0° C., then overnight at RT. Dilute the mixture with chloroform/IPA (3/1). Wash the solution with saturated aqueous sodium chloride. Dry it over sodium sulfate. Concentrate the solution in vacuo to a dark residue. Purify by column chromatography (hexane→20% ethyl acetate in hexane) to afford the title compound as a colorless solid (3 g, 66%). MS (ES) m/z 186 [M+1]⁺.

Prepare the following intermediate using a procedure similar to the one for 2-Fluoro-5-(1-methoxymethoxy-ethyl)-pyridine:

| Prep | Compound Name | MS (ES) m/z [M + 1]⁺ |
|---|---|---|
| 13 | 2-Chloro-5-(1-(methoxymethoxy)ethyl)pyridine | 202 |

PREPARATION 14

5-Cyclopropyl-2-fluoro-pyridine

Combine 2-fluoro-5-iodo-pyridine (1.12 g, 5 mmol), cyclopropylboronic acid (645 mg, 7.5 mmol), palladium acetate (56 mg, 0.25 mmol) and potassium phosphate (3.2 g, 15 mmol) in toluene/water (20:1, 21 mL). Heat the mixture at 100° C. for 4 h. Dilute the mixture with chloroform-IPA (3:1, 100 mL). Wash the organic phase with saturated aqueous sodium chloride and water. Dry the mixture over sodium sulfate. Concentrate the solution in vacuo to a brown oil. Purify by column chromatography (20% ethyl acetate in hexane) to afford the title compound as a pale yellow oil (430 mg, 63%).

PREPARATION 15

5-Cyclopropyl-2-fluoro-3-iodo-pyridine

Cool a solution of 5-cyclopropyl-2-fluoro-pyridine (1.3 g, 9.5 mmol) in THF (20 mL) to −75° C. in a dry ice-acetone bath under nitrogen. Add lithium diisopropylamide (2 M in THF, 6 mL, 12 mmol) during a period of 30 min. Stir the mixture for another 3 h before adding iodine (2.9 g, 11.4 mmol, dissolved in 50 mL of THF). Keep stirring for 2 more hours before adding water (100 mL) to the mixture. Then allow to warm to RT during 1 h under stirring. Treat the mixture with a saturated sodium thiosulfate solution (50 mL). Extract the solution with ether. Concentrate the solution in vacuo. Purify by column chromatography (hexane→20% ethyl acetate in hexane) to afford the title compound as a yellow oil (1.7 g, 68%). $^1$H NMR (400 MHz-CDCl$_3$) δ 7.99 (d, J=3 Hz, 1H), 7.39 (td, J=3, 5 Hz, 1H), 6.79 (dd, J=3, 8 Hz, 1H), 0.96-1.02 (m, 2H), 0.63-0.69 (m, 2H).

Prepare the following intermediates using a procedure similar to the one for 5-Cyclopropyl-2-fluoro-3-iodo-pyridine:

| Prep | Compound Name | MS (ES) m/z [M + 1]$^+$ |
|------|---------------|-------------------------|
| 16 | 2-Fluoro-3-iodo-5-(1-methoxymethoxy-ethyl)-pyridine | 312 |
| 17 | 2-Chloro-3-iodo-5-(1-(methoxymethoxy)ethyl)-pyridine | 328 |

PREPARATION 18

5-Cyclopropyl-2-fluoro-4-iodo-pyridine

Cool a solution of 5-cyclopropyl-2-fluoro-3-iodo-pyridine (1.7 g, 6.5 mmol) in THF (20 mL) to −75° C. in a dry ice-acetone bath under nitrogen. Add lithium diisopropylamide (2 M in THF, 3.9 mL, 7.8 mmol) during a period of 30 min. Stir the mixture for another 3 h before adding water (100 mL). Then allow the temperature to rise to RT during 1 h under stirring. Extract the solution with ether. Concentrate the solution in vacuo to a brown oil. Purify by column chromatography (hexane→15% ethyl acetate in hexane) to afford the title compound as a yellow oil (1.1 g, 65%). $^1$H NMR (400 MHz-CDCl$_3$) δ 8.03 (dd, J=3, 8 Hz, 1H), 7.99 (s, 1H), 0.91-1.00 (m, 2H), 0.71-0.78 (m, 2H).

Prepare the following intermediates using a procedure similar to the one for 5-Cyclopropyl-2-fluoro-4-iodo-pyridine:

| Prep | Compound Name | MS (ES) m/z [M + 1]$^+$ |
|------|---------------|-------------------------|
| 19 | 2-Fluoro-4-iodo-5-(1-methoxymethoxy-ethyl)-pyridine | 312 |
| 20 | 2-Chloro-4-iodo-5-(1-(methoxymethoxy)ethyl)-pyridine | 328 |

PREPARATION 21

1-(6-Fluoro-4-iodo-pyridin-3-yl)-ethanol

Add 1 N HCl (5 mL) to a solution of 2-fluoro-4-iodo-5-(1-methoxymethoxy-ethyl)-pyridine (1 g, 3.2 mmol) in methanol (10 mL). Stir the mixture overnight. Dilute the reaction mixture with sodium carbonate (2 N). Extract the product into chloroform. Dry the organic phase over sodium sulfate. Concentrate the solution in vacuo. Purify the crude by column chromatography (10% methanol in DCM) to afford the title compound as a white solid (0.75 g, 87%). MS (ES) m/z 268 [M+1]$^+$.

Prepare the following intermediate using a procedure similar to the one for 1-(6-Fluoro-4-iodo-pyridin-3-yl)-ethanol:

| Prep | Compound Name | MS (ES) m/z [M + 1]$^+$ |
|------|---------------|-------------------------|
| 22 | 1-(6-Chloro-4-iodopyridin-3-yl)ethanol | 284 |

PREPARATION 23

Methanesulfonic acid 1-(6-fluoro-4-iodo-pyridin-3-yl)-ethyl ester

Add methanesulfonyl chloride (1.93 g, 16.8 mmol) to a solution of 1-(6-fluoro-4-iodo-pyridin-3-yl)-ethanol (1.5 g, 5.6 mmol) and diisopropylethylamine (2.2 g, 16.8 mmol) in DCM (50 mL) at 0° C. Continue to stir the mixture at 0° C. to RT for 4 h. Dilute the reaction mixture with diluted sodium carbonate. Extract the product into chloroform. Dry the organic phase over sodium sulfate. Concentrate the solution in vacuo. Purify the crude by column chromatography (20% ethyl acetate in hexane) to afford the title compound as a white solid (1.24 g, 64%). MS (ES) m/z 346 [M+1]$^+$.

PREPARATION 24

5-(1-Azido-ethyl)-2-fluoro-4-iodo-pyridine

Add sodium azide (0.45 g, 7 mmol) and tetra-N-butylammonium bromide (0.12 g, 0.4 mmol) to a solution of methanesulfonic acid 1-(6-fluoro-4-iodo-pyridin-3-yl)-ethyl ester (1.2 g, 3.5 mmol) in DMF (20 mL) at 0° C. Stir the mixture at RT for 42 h. Dilute the reaction mixture with chloroform. Wash the organic phase with water and saturated aqueous sodium chloride. Dry the organic phase over sodium sulfate. Concentrate the solution in vacuo. Purify by column chromatography (20% ethyl acetate in hexane) to afford the title compound as a white solid (0.77 g, 76%). $^1$H NMR (400 MHz-CDCl$_3$) δ 1.56 (d, J=6.8 Hz, 1H), 4.90 (m, 1H), 7.45 (d, J=3.2 Hz, 1H), 8.17 (s, 3H).

PREPARATION 25 tert-Butyl 4-(1-(6-chloro-4-iodopyridin-3-yl)ethyl)piperazine-1-carboxylate

To an ice-cooled solution of 6-chloro-4-iodopyridin-3-yl)ethanol (300 mg, 1.06 mmol) and triethylamine (737 μL, 5.29 mmol) in acetonitrile (10 mL), add a solution of methanesulphonic anhydride (553 mg, 3.17 mmol) in CH$_3$CN (3 mL) dropwise. Stir for 40 min at the same temperature, and add a solution of N-tert-butoxycarbonylpiperazine (1.97 g, 10.6 mmol) in CH$_3$CN (5 mL). Heat the mixture to 60° C. overnight. Quench with saturated NaHCO$_3$ (10 mL) and extract with ethyl acetate (50 mL×3). Wash the organics with saturated aqueous sodium chloride, dry over Na$_2$SO$_4$, filter, and remove the solvent by rotary evaporation. Purify by normal phase column chromatography (10% ethyl acetate in hex-

PREPARATION 26

1-(6-Chloropyridin-3-yl)ethanone oxime

Combine 1-(6-chloropyridin-3-yl)ethanone (3.4 g, 22.8 mmol), hydroxylamine (50%) in water (5.77 g, 87.4 mmol) and 0.75 mL of acetic acid in 15 mL of dioxane in a pressure vessel. Seal the vessel and heat the mixture in an oil bath for 3 h at 150° C. Cool the mixture to RT. Dilute with chloroform/IPA (3/1), wash with water, and aqueous saturated sodium chloride. Separate the layers and dry the organic layer over sodium sulfate. Concentrate in vacuo to afford the title compound (3.52 g, 94%). MS (ES) m/z 171 [M+1]$^+$.

PREPARATION 27

1-(6-Chloropyridin-3-yl)ethanamine

Cool a solution of sodium borohydride (2.96 g, 82.65 mmol) and titanium tetrachloride (1 M in toluene, 41.33 mL, 41.33 mmol) in 50 mL of dry 1,2-dimethoxyethane to 0° C. under N$_2$. Add 1-(6-chloropyridin-3-yl)ethanone oxime (3.52 g, 20.66 mmol) to the solution dropwise. Stir the mixture overnight at RT. Quench the reaction with 200 mL of water. Basify the mixture with ammonium hydroxide. Subsequently, extract the crude product into toluene and ethyl acetate. Separate the layers and dry the organic layer over sodium sulfate. Concentrate in vacuo to give the crude product (1.24 g, 38%). $^1$H NMR (400 MHz, CDCl$_3$) δ 3.53 (s, 3H), 5.23 (s, 2H), 7.39 (d, J=4.0 Hz, 1H), 7.96 (d, J=1.6 Hz, 1H).

PREPARATION 28

1-(6-Methylpyridin-3-yl)ethanamine

Stir a mixture of 1-(6-methylpyridin-3-yl)-ethanone (10 g, 74 mmol) in titanium tetra(isopropoxide) (42.1 g, 148 mmol) and ammonia (370 mmol, 2 M in methanol) under N$_2$ for 6 h at RT. To this mixture add sodium tetrahydroborate (4.2 g, 111 mmol) and stir overnight. Quench the reaction mixture with ammonium hydroxide and filter the mixture. From the filtrate, remove the solvent and extract the residue with DCM, wash with saturated aqueous sodium chloride and dry over Na$_2$SO$_4$, filter, and remove the solvent to obtain the title compound as a dark yellow oil (8.16 g). MS (ES) m/z 137 [M+1]$^+$.

PREPARATION 29 tert-Butyl 1-(6-methylpyridin-3-yl)ethylcarbamate

Add diisopropylethylamine (11.6 g, 89.9 mmol) and di-ten-butyldicarbonate (15.7 g, 71.9 mmol) to a solution of 1-(6-methylpyridin-3-yl)-ethylamine (8.16 g, 59.9 mmol) in acetonitrile (50 mL) and stir the mixture overnight. Wash the mixture with saturated NaHCO$_3$ (200 mL) and extract into DCM, wash with saturated aqueous sodium chloride and dry over Na$_2$SO$_4$. Purify by column chromatography 5% to 50% ethyl acetate in hexanes to obtain the title compound as a pale yellow oil (7.3 g). MS (ES) m/z 237 [M+1]$^+$.

PREPARATION 30 tert-Butyl 1-(4-iodo-6-methylpyridin-3-yl)ethylcarbamate

Add a solution of tert-butyl 1-(6-methylpyridin-3-yl)ethylcarbamate (6.85 g, 29 mmol) to a solution of tert-butyllithium (51.1 mL, 87 mmol) in THF (70 mL) at −78° C. in THF (20 mL) under N$_2$ using a double-tipped needle. After 30 min, add iodine (11.0 g, 43.5 mmol) in THF (25 mL) over 30 min at −78° C. Stir for 1 h and then warm up to RT. Quench with water, extract in ethyl acetate, wash with saturated aqueous sodium chloride, and dry over Na$_2$SO$_4$. Purify on column chromatography 5% to 50% ethyl acetate in hexanes to obtain the title compound (620 mg). MS (ES) m/z 363 [M+1]$^+$.

PREPARATION 31

(6-Fluoro-4-iodo-pyridin-3-ylmethoxy)-ethanol

Add sodium hydride (54 mg, 2.25 mmol) to 2.5 mL ethylene glycol at 0° C. and stir for 30 min at RT. Add 5-bromomethyl-2-fluoro-4-iodo-pyridine (0.69 g, 2.14 mmol) and heat it to 120° C. for 30 min. Cool to RT, dilute with 70 mL of water, and extract with ether (3×50 mL). Combine organic layers, wash with saturated aqueous sodium chloride, thy over MgSO$_4$, and remove the solvent. Purify by chromatography with diethylether to obtain the title compound (240 mg, 38%). MS (ES) m/z 296 [M+1]$^+$.

PREPARATION 32

4-(6-Fluoro-4-iodo-pyridin-3-ylmethyl)-morpholine

In a flask, combine 5-bromomethyl-2-fluoro-4-iodo-pyridine (6.13 g, 19.4 mmol), morpholine (3.38 g, 38.8 mmol) and dry CH$_3$CN (100 mL) under nitrogen. Add N,N-diisopropylethylamine (6.76 mL, 38.80 mmol, 2 M THF solution). Heat at 81° C. for 2 h and cool to RT. Dilute with DCM and wash with water and aqueous saturated sodium chloride. Separate the organic layer from the aqueous layer and dry over magnesium sulfate. After filtration, concentrate in vacuo to give the title compound 6.23 g (100%). MS (ES) m/z 323 [M+1]$^+$.

Prepare the following intermediates using a procedure similar to the one for 4-(6-Fluoro-4-iodo-pyridin-3-ylmethyl)-morpholine:

| Prep | Compound Name | MS (ES) m/z [M + 1]$^+$ |
|---|---|---|
| 33 | N-(6-Fluoro-4-iodo-pyridin-3-ylmethyl)-dimethylamine | 280 |
| 34 | (6-Fluoro-4-iodo-pyridin-3-ylmethyl)-methyl-carbamic acid tert-butyl ester | 367 |
| 35 | 5-Azetidin-1-ylmethyl-2-fluoro-4-iodo-pyridine | 292 |
| 36 | Cyclopropyl-(6-fluoro-4-iodo-pyridin-3-ylmethyl)-amine | 292 |
| 37 | 2-Fluoro-4-iodo-5-pyrrolidin-1-ylmethyl-pyridine | 306 |
| 38 | Ethyl-(6-fluoro-4-iodo-pyridin-3-ylmethyl)-methylamine | 294 |
| 39 | (6-Fluoro-4-iodo-pyridin-3-ylmethyl)-methyl-propyl-amine | 308 |

-continued

| Prep | Compound Name | MS (ES) m/z [M + 1]+ |
|---|---|---|
| 40 | (6-Fluoro-4-iodo-pyridin-3-ylmethyl)-isopropyl-methyl-amine | 308 |
| 41 | (6-Fluoro-4-iodo-pyridin-3-ylmethyl)-propyl-amine | 294 |
| 42 | (6-Fluoro-4-iodo-pyridin-3-ylmethyl)-isopropyl-amine | 294 |
| 43 | Ethyl-(6-fluoro-4-iodo-pyridin-3-ylmethyl)-amine | 280 |
| 44 | 2-((6-Fluoro-4-iodopyridin-3-yl)methylamino)ethanol | m/z 296 [GCMS] |

PREPARATION 45

2-Fluoro-5-methoxymethoxy-pyridine

Add 6-fluoro-pyridin-3-ol (3.5 g, 30.95 mmol) to a suspension of sodium hydride (1.49 g, 37.1 mmol) in DMF (20 mL). Stir the mixture for 1 h. Add chloromethyl methyl ether (2 g, 25.0 mmol). Stir the mixture at RT overnight. Dilute the mixture with ethyl acetate and water. Wash the organic layer with water and aqueous saturated sodium chloride. Dry the mixture over sodium sulfate. Concentrate the solution in vacuo to a brown oil. Purify by column chromatography (10% ethyl acetate in hexane) to afford the title compound (4.30 g, 88%) as yellow oil. $^1$H NMR (400 MHz, CDCl$_3$) δ 3.48 (s, 3H), 5.15 (s, 2H), 6.85 (dd, J=3.6 Hz, J=8.8 Hz, 1H), 7.47 (m, 1H), 7.96 (m, 1H).

PREPARATION 46

2-Fluoro-4-iodo-5-methoxymethoxy-pyridine

Cool a solution of 2-fluoro-5-methoxymethoxy-pyridine (4.1 g, 26.1 mmol) in THF (60 mL) to −75° C. Add tert-butyllithium (1.7 M in pentane, 30.4 mL, 51.7 mmol) over a period of 30 min. Stir the mixture for an additional half an hour. Add iodine (9.8 g, 38.6 mmol, dissolved in 60 mL of THF). Stir for 1 h after the addition is complete. Allow the temperature to raise to RT over 1 h while stirring. Treat the mixture with water. Extract the solution with ethyl acetate three times. Wash the organic layer with aqueous saturated sodium chloride. Dry the mixture over sodium sulfate. Concentrate the solution in vacuo to a brown solid. Triturate the brown solid with hexane. Filter to afford the title compound (3.9 g, 53%) as a brown solid. $^1$H NMR (400 MHz, CDCl$_3$) δ 3.53 (s, 3H), 5.23 (s, 2H), 7.39 (d, J=4.0 Hz, 1H), 7.96 (d, J=1.6 Hz, 1H).

PREPARATION 47

6-Fluoro-4-iodo-pyridin-3-ol

Add HCl (3 M in water, 31 mL, 93.0 mmol) to a solution of 2-fluoro-4-iodo-5-methoxymethoxy-pyridine (3.9 g, 13.8 mmol) in THF (20 mL). Stir the mixture at 60° C. for 3 h and cool down the mixture. Adjust the pH to 7 with slow addition of a saturated aqueous sodium bicarbonate solution. Extract the solution with ethyl acetate three times. Wash the organic layer with aqueous saturated sodium chloride. Dry the mixture over sodium sulfate. Concentrate the solution in vacuo to afford the title compound (3.2 g, 97%) as a yellow solid. MS (ES) m/z 240 [M+1]+.

PREPARATION 48

2-[2-(6-Fluoro-4-iodo-pyridin-3-yloxy)-ethyl]-isoindole-1,3-dione

Cool a suspension of 6-fluoro-4-iodo-pyridin-3-ol (1.5 g, 6.28 mmol) and K$_2$CO$_3$ (4.38 g, 31.4 mmol) in DMF (10 mL) to 0° C. in an ice bath under nitrogen. Add 2-(2-bromo-ethyl)-isoindole-1,3-dione (3.19 g, 12.55 mmol). Stir the mixture at RT overnight. Add water. Extract with ethyl acetate. Wash the solution with aqueous saturated sodium chloride. Dry over sodium sulfate. Concentrate the solution in vacuo. Purify by column chromatography (hexane to 30% ethyl acetate in hexane) to afford the title compound as a yellow oil (1.51 g, 58%). MS (ES) m/z 413 [M+1]+.

PREPARATION 49

2-(6-Fluoro-4-iodo-pyridin-3-yloxy)-ethylamine

Add hydrazine (70 mg, 2.12 mmol) to a solution of 2-[2-(6-fluoro-4-iodo-pyridin-3-yloxy)-ethyl]-isoindole-1,3-dione (440 mg, 1.06 mmol) in ethanol (10 mL). Stir the solution at RT overnight. Filter to remove the solid and concentrate the filtrate to a light yellow solid. Purify by column chromatography (10% 2 M ammonia in methanol in methylene chloride) to afford the title compound as a light yellow oil (250 mg, 83.8%). $^1$H NMR (400 MHz, CD$_3$CN) δ 2.12 (s, 2H), 3.03 (t, J=5.2 Hz, 2H), 4.10 (t, J=5.2 Hz, 2H), 7.47 (d, J=4.0 Hz, 1H), 7.69 (d, J=2.0 Hz, 1H).

PREPARATION 50

1-(6-Fluoro-4-iodo-pyridin-3-yloxy)-propan-2-one

Cool a suspension of 6-fluoro-4-iodo-pyridin-3-ol (1.6 g, 6.69 mmol) and K$_2$CO$_3$ (2.8 g, 20.1 mmol) in DMF (10 mL) to 0° C. in an ice bath under nitrogen. Add chloroacetone (0.78 g, 8.03 mmol) during a period of 30 min. Stir the mixture at RT for 1.5 h. Add water and extract with ethyl acetate. Wash the solution with aqueous saturated sodium chloride. Dry over sodium sulfate. Concentrate the solution in vacuo. Purify by column chromatography (hexane to 10% ethyl acetate in hexane) to afford the title compound (1.5 g, 76%). MS (ES) m/z 296 [M+1]+.

PREPARATION 51

1-(6-Fluoro-4-iodo-pyridin-3-yloxy)-propan-2-ol

Add NaBH$_4$ (35 mg, 0.94 mmol) to a solution of 1-(6-fluoro-4-iodo-pyridin-3-yloxy) propan-2-one (240 mg, 0.81 mmol) in methanol (4 mL) slowly. Stir the mixture at RT for 3 h. Add 1 N HCl and water. Extract with methylene chloride. Wash the organic layer with aqueous saturated sodium chloride. Dry over sodium sulfate. Concentrate the solution in vacuo to a yellow solid. Purify by column chromatography (hexane to 10% ethyl acetate in hexane) to afford the title compound as a light yellow solid (240 mg, 99%). MS (ES) m/z 298 [M+1]+.

PREPARATION 52

2-[2-(6-Fluoro-4-iodo-pyridin-3-yloxy)-1-methyl-ethyl]-isoindole-1,3-dione

Heat a mixture of 6-fluoro-4-iodo-pyridin-3-ol (150 mg, 0.63 mmol), toluene-4-sulfonic acid 2-(1,3-dioxo-1,3-dihydro-isoindol-2-yl)-propyl ester (226 mg, 0.63 mmol), cesium carbonate (206 mg, 0.63 mmol) in DMF (2 mL) at 100° C. for 5 h. Cool the mixture and add water. Extract with ethyl acetate. Wash the organic layer with aqueous saturated sodium chloride. Dry over sodium sulfate. Concentrate the solution in vacuo to a light yellow solid. Purify by column chromatography (hexane to 10% ethyl acetate in hexane) to afford the title compound as a white solid (115 mg, 43%). MS (ES) m/z 427 [M+1]+.

Prepare the following intermediates using a procedure similar to the one for 2-[2-(6-Fluoro-4-iodo-pyridin-3-yloxy)-1-methyl-ethyl]-isoindole-1,3-dione:

| Prep | Compound Name | MS (ES) m/z [M + 1]+ |
|---|---|---|
| 53 | S-2-[2-(6-Fluoro-4-iodo-pyridin-3-yloxy)-1-methyl-ethyl]-isoindole-1,3-dione | 427 |
| 54 | R-2-[2-(6-Fluoro-4-iodo-pyridin-3-yloxy)-1-methyl-ethyl]-isoindole-1,3-dione | 427 |

PREPARATION 55

2-Fluoro-4-iodo-5-[2-(tetrahydro-pyran-2-yloxy)-ethoxy]-pyridine

Add 6-fluoro-4-iodo-pyridin-3-ol (0.5 g, 2.09 mmol) to a suspension of sodium hydride (60% dispersion in mineral oil, 0.1 g, 2.51 mmol) in DMF (6 mL). Stir the mixture for 1 h. Add 2-(2-bromo-ethoxy)-tetrahydropyran (0.51 g, 2.34 mmol). Stir the solution at RT overnight. Dilute the mixture with ethyl acetate and water. Wash the organic layer with aqueous saturated sodium chloride and water. Dry the mixture over sodium sulfate. Concentrate the solution in vacuo. Purify by column chromatography (10% ethyl acetate in hexane) to afford the title compound (0.58 g, 75.5%) as a light yellow oil. MS (ES) m/z 368 [M+1]+.

Prepare the following intermediate using a procedure similar to the one for 2-Fluoro-4-iodo-5-[2-(tetrahydro-pyran-2-yloxy)-ethoxy]-pyridine:

| Prep | Compound Name | MS (ES) m/z [M + 1]+ |
|---|---|---|
| 56 | 2-Chloro-4-iodo-5-(2-(tetrahydro-2H-pyran-2-yloxy)ethoxy)pyridine | 384 |

PREPARATION 57

3-Methoxymethoxy-pyridine

Dissolve 3-hydroxypyridine (7 g, 74 mmol) in THF (20.6 mL) and DMF (34.4 mL) and cool to −15° C. Add potassium tert-butoxide (8.3 g, 74 mmol) and stir at −15° C. for 30 min. Treat the mixture with chloromethylmethyl ether (5.81 mL, 77 mmol) dropwise over 40 min. After the addition is complete, stir the mixture at −15° C. for an additional 1 h. Remove the ice bath and allow the mixture to warm slowly to 15° C. Pour the mixture into saturated aqueous sodium chloride and stir vigorously for 10 min. Extract the resulting solution with three portions of ethyl acetate. Combine the organic extracts and wash with saturated aqueous sodium chloride, dry over sodium sulfate, filter, and concentrate in vacuo. 1H NMR (400 MHz, CDCl3) δ 8.42 (d, J=3 Hz, 1H), 828 (d, J=5 Hz, 1H), 7.37-7.42 (m, 1H), 7.21-7.27 (m, 1H), 5.20 (s, 2H), 3.49 (s, 3H).

PREPARATION 58

2-Chloro-5-methoxymethoxy-pyridine

Suspend sodium hydride (3.7 g, 93 mmol) in DMF (50 mL) and add a solution of 2-chloro-5-hydroxypyridine (10 g, 77 mmol) in DMF (20 mL) dropwise over 45 min. Stir the resulting solution at RT for 1.5 h. Add chloromethylmethyl ether (6.6 mL, 86 mmol) dropwise over 45 min. Stir the resulting mixture at RT for 12 h. Dilute the mixture with ethyl acetate, water, and saturated aqueous sodium chloride. Isolate the organic solution and wash with three portions of water, one portion of saturated aqueous sodium chloride, dry over sodium sulfate, filter, and concentrate in vacuo. Purify the crude product by column chromatography on 330 g of silica gel eluting with a gradient from hexane to 30% ethyl acetate in hexane over 20 min and then hold at 30% ethyl acetate in hexane for 30 min to give the title compound 10.8 g (81%) as a clear oil. MS (ES) m/z 174.0 [M+1]+.

PREPARATION 59

2-Chloro-4-iodo-5-methoxymethoxy-pyridine

Add tert-buty lithium (1.7 M in pentane, 72 mL, 123 mmol) to a solution of 2-chloro-5-methoxymethoxy-pyridine (10.8 g, 62 mmol) in THF (300 mL) at −70° C. dropwise over 10 min. Stir the resulting solution at −70° C. for 30 min. Add a solution of iodine (23 g, 92 mmol) in THF (150 mL) dropwise over 30 min. Stir the resulting solution at −70° C. for 1 h. Remove the ice bath and allow the reaction to warm to RT. Dilute the mixture with ethyl acetate and water and isolate the phases. Extract the aqueous phase with two portions of ethyl acetate. Combine the organic extracts and wash with two portions of aqueous sodium thiosulfate, one portion of water, and one portion of saturated aqueous sodium chloride. Dry over sodium sulfate, filter, and evaporate. Triturate the resulting solid with hexane. Collect the solid by vacuum filtration and wash the solid with hexane. Dry the solid under vacuum to give the title compound 10.8 g (58%) as a brown solid. 1H NMR (400 MHz, DMSO-d6) δ 8.08 (s, 1H), 7.98 (s, 1H), 5.43 (s, 2H), 3.40 (s, 3H).

Prepare the following intermediate with a procedure similar to the one for 2-Chloro-4-iodo-5-methoxymethoxy-pyridine:

| Prep | Compound Name | MS (ES) m/z [M + 1]+ |
|---|---|---|
| 60 | tert-Butyl 1-(6-chloro-4-iodopyridin-3-yl)ethylcarbamate | 383 |

PREPARATION 61

[2-(6-Fluoro-4-iodo-pyridin-3-yloxy)-ethyl]methyl-carbamic acid tert-butyl ester Add sodium hydride (620 mg, 26 mmol) to a solution of [2-(6-fluoro-4-iodo-pyridin-3-yloxy)-ethyl]-carbamic acid tert-butyl ester (0.33 g, 0.86 mmol) in 3 mL of DMF. Stir the mixture at RT for 1 h and add methyl iodide (0.37 g, 2.59 mmol). Stir the reaction mixture at RT overnight. Add water and extract with ethyl acetate. Wash the organic layer with saturated aqueous sodium chloride. Dry the mixture over sodium sulfate. Concentrate the solution in vacuo. Purify the residue by column chromatography (20% ethyl acetate in hexane) to afford the title compound as a light yellow solid (0.13 g, 38%). $^1$H NMR (400 MHz, CD$_3$CN) δ 1.45 (s, 9H), 3.08 (s, 3H), 3.59 (t, J=5.6 Hz, 2H), 4.20 (t, J=5.6 Hz, 2H), 5.07 (s, 1H), 7.38 (d, J=3.2 Hz, 1H), 7.61 (d, J=1.2 Hz, 1H).

PREPARATION 62

6-Chloro-4-iodo-pyridin-3-ol

Treat a solution of 2-chloro-4-iodo-5-methoxymethoxy-pyridine (8.1 g, 27 mmol) in THF (40 mL) with 3 N HCl (61 mL). Heat the resulting mixture to 60° C. for 3 h. Cool the mixture to RT and adjust the pH to 7 by the slow addition of saturated aqueous sodium bicarbonate solution. Extract the mixture with three portions of ethyl acetate. Combine the organic extracts and dry over sodium sulfate, filter, and concentrate in vacuo to give the title compound 6.8 g (98%) as a brown solid. $^1$H NMR (400 MHz, DMSO-d$_6$) δ 11.04 (s, 1H), 7.81-7.87 (m, 2H).

PREPARATION 63

2-Chloro-5-ethoxy-4-iodo-pyridine

Treat a solution of 6-chloro-4-iodo-pyridin-3-ol (4.9 g, 19 mmol) and potassium carbonate (8.0 g, 58 mmol) in DMF (50 mL) with ethyl iodide (4.7 mL, 58 mmol). Heat the mixture at 60° C. for 3 h. Cool the mixture to RT and filter through filter paper. Dilute the mixture with ethyl acetate and wash with a 10% aqueous citric acid solution. Combine the aqueous solutions and extract with two additional portions of ethyl acetate. Combine the organic extracts and wash with three portions of water, one portion of saturated aqueous sodium chloride, dry over sodium sulfate, filter, and concentrate in vacuo to give the title compound 5.1 g (93%) as a brown solid. $^1$H NMR (400 MHz, DMSO-d$_6$) δ 8.00 (s, 1H), 7.93 (s, 1H), 4.18 (q, J=7 Hz, 2H), 1.35 (t, J=7 Hz, 3H).

PREPARATION 64

2,2-Dimethyl-N-pyridin-3-yl-propionamide

Equip a 250-mL round bottom flask with an ice bath, a magnetic stirrer, and a N$_2$ atmosphere. Add 3-aminopyridine (15 g, 159 mmol), THF (60 mL), diethylether (60 mL), triethylamine (17.7 g, 24.4 mL, 175 mmol). Cool the mixture to 0° C. and add trimethylacetyl chloride (21.0 g, 14.9 mL, 175 mmol) slowly via syringe. Mix overnight while warming to RT. Add water (100 mL), transfer to a separatory funnel, and extract and discard the lower aqueous layer. Dry the organic layer over Na$_2$SO$_4$, filter, and concentrate via a rotovap to a colorless oil that solidifies on cooling. Dry under high vacuum for 2.5 h to give the title compound as a tan solid 21.56 g (76%). MS (ES) m/z 179 [M+1]$^+$.

PREPARATION 65

N-(4-Iodo-pyridin-3-yl)-2,2-dimethyl-propionamide

Equip a 250-mL round bottom flask with a magnetic a stirrer, a thermocouple, a dry ice/acetone bath, a N$_2$ atmosphere, and an addition funnel. Charge with 2,2-dimethyl-N-pyridin-3-yl-propionamide (3.0 g, 16.8 mmol), diethylether (67 mL), and tetramethylene diamine (4.68 g, 6.08 mL, 40.3 mmol). Cool the reaction to −78° C. Add slowly via glass syringe n-butyllithium (2.5 M solution in hexane, 16.2 mL, 40.3 mmol) over 10 min. Warm the reaction to −13° C. over 2 h. Cool the reaction to −78° C. Prepare an iodine solution (I$_2$ 8.5 g, 33.6 mmol in THF (20 mL)). Add the iodine solution to the reaction via the addition funnel and stir 2.5 h. at −68° C. Quench the reaction with the addition of a saturated NH$_4$Cl solution (40 mL) and transfer into a separatory funnel. Add ethyl acetate (100 mL). Extract and discard the lower aqueous phase. Wash the organic layer with a saturated sodium thiosulfate solution (100 mL) and extract. Wash the organic phase with saturated aqueous sodium chloride and extract. Dry the organic phase over Na$_2$SO$_4$ and filter. Concentrate the product via rotary evaporation. Chromatograph on silica (80 g) eluting with gradient of 100% DCM to 70% ethyl acetate/30% DCM to afford 1.19 g (23%) of the title compound. MS (ES) m/z 306 [M+1]$^+$.

PREPARATION 66

[2-(6-Fluoro-4-iodo-pyridin-3-yloxy)-ethyl]-carbamic acid tert-butyl ester

Add diisopropylethylamine (0.23 g, 1.77 mmol) to a solution of 2-(6-fluoro-4-iodo-pyridin-3-yloxy)-ethylamine (0.25 g, 0.89 mmol) and di-tert-butyldicarbonate (0.29 g, 1.33 mmol) in 5 mL of DCM. Stir the mixture overnight at RT. Dilute the mixture with DCM, wash the organic layer with saturated aqueous sodium chloride, dry over sodium sulfate, and concentrate in vacuo give a crude oil. Purify by column chromatography (30% ethyl acetate in hexane) to afford the title compound (0.33 g, 97%). $^1$H NMR (400 MHz, CDCl$_3$) δ 1.41 (s, 9H), 3.56 (t, J=5.2 Hz, 2H), 4.10 (t, J=5.2 Hz, 2H), 5.07 (s, 1H), 7.34 (d, J=3.6 Hz, 1H), 7.69 (d, J=1.6 Hz, 1H).

Prepare the following intermediates with a procedure similar to the one for [2-(6-Fluoro-4-iodo-pyridin-3-yloxy)-ethyl]-carbamic acid tert-butyl ester:

| Prep | Compound Name | MS (ES) m/z [M + 1]$^+$ |
|---|---|---|
| 67 | [1-(6-Fluoro-pyridin-3-yl)-ethyl]-carbamic acid tert-butyl ester | 241 |
| 68 | tert-Butyl 6-fluoropyridin-3-ylcarbamate | 213 |
| 69 | tert-Butyl 1-(6-chloropyridin-3-yl)ethylcarbamate | 257 |

PREPARATION 70 tert-Butyl 1-(6-chloro-4-iodopyridin-3-yl)ethylcarbamate

Dissolve tert-butyl 1-(6-chloropyridin-3-yl)ethylcarbamate (3.77 g, 14.7 mmol) in THF (60 mL). Add tert-butyllithium (1.7 M heptane solution, 25.9 mL, 44.0 mmol) at −78° C. under N$_2$. Stir the reaction solution for 0.5 h at −78° C. Add a solution of iodine (5.59 g, 22.0 mmol) in THF (44 mL) dropwise over 30 min under N$_2$ at −78° C. Stir the resulting solution at −78° C. for 1 h, then from −78° C. to RT for 1 h. Quench the reaction with water. Extract with ethyl acetate. Wash the organic layer with water and saturated aqueous sodium chloride. Dry over MgSO$_4$. After filtration, concentrate and purify the crude by FCC (0.1% to 1% 2 M NH₃ methanol solution/CH₂Cl₂) to afford the title compound (1.34 g, 24%) with 98% HPLC purity. MS (ES) m/z 383 [M+1]⁺

Prepare the following intermediates with a procedure similar to the one for tert-Butyl 1-(6-chloro-4-iodopyridin-3-yl)ethylcarbamate:

| Prep | Compound Name | MS (ES) m/z [M + 1]⁺ |
|---|---|---|
| 71 | [1-(6-Fluoro-4-iodo-pyridin-3-yl)-ethyl]-carbamic acid tert-butyl ester | 367 |
| 72 | tert-Butyl 6-fluoro-4-iodopyridin-3-ylcarbamate | 339 |

PREPARATION 73

6-Fluoro-4-iodopyridin-3-amine

Dissolve tert-butyl 6-fluoro-4-iodopyridin-3-ylcarbamate (1.47 g, 4.35 mmol) in DCM (20 mL). Add trifluoroacetic acid (TFA) (20 mL). Stir at RT under N₂ for 2 h. Remove the solvent under reduced pressure. Dry in vacuo to afford 6-fluoro-4-iodopyridin-3-amine in TFA salt (1.02 g, 99%) with 100% HPLC purity. MS (ES) m/z 239 [M+1]⁺.

PREPARATION 74

6-Fluoro-4-iodo-N-(2-(tetrahydro-2H-pyran-2-yloxy)ethyl)pyridin-3-amine

Mix 6-fluoro-4-iodopyridin-3-amine TFA salt (0.36 g, 1.50 mmol), 2-[(2-bromoethyl)oxy]tetrahydro-2H-pyran (1.38 g, 6.60 mmol), potassium hydroxide (0.19 g, 3.30 mmol), potassium fluoride (0.19 g, 3.30 mmol), and tetrabutylammonium iodide (0.11 g, 0.3 mmol) in 1,4-dioxane (1.5 mL) in a seal reactor. Heat the reaction mixture at 100° C. overnight. Cool the reaction mixture to RT. Quench with water. Extract with ethyl acetate, wash the organic layer with water and saturated aqueous sodium chloride. Dry over MgSO₄. After filtration, concentrate and purify by FCC (0.1% to 1% 2 M NH₃ methanol solution/CH₂Cl₂) to give the title compound (0.36 g, 66%) with 100% HPLC purity. MS (ES) m/z 367 [M+1]⁺.

PREPARATION 75

2-(6-Fluoro-4-iodopyridin-3-ylamino)ethanol

Dissolve 6-fluoro-4-iodo-N-(2-(tetrahydro-2H-pyran-2-yloxy)ethyl)pyridin-3-amine (0.20 g, 0.55 mmol) in ethanol (5.5 mL). Add pyridinium p-toluenesulfonate (0.014 g, 0.055 mmol). Heat the reaction mixture at 50° C. overnight. Remove the solvent under reduced pressure. Purify by FCC (0.1% to 1% 2 M NH₃ methanol solution/CH₂Cl₂) to give the title compound (44 mg, 28%) with 100% HPLC purity. MS (ES) m/z 283 [M+1]⁺.

PREPARATION 76

6-Fluoro-4-iodo-N-(2-methoxyethyl)pyridin-3-amine

Mix 6-fluoro-4-iodopyridin-3-amine in TFA salt (0.36 g, 1.50 mmol), 2-chloroethyl methyl ether (0.31 g, 3.30 mmol), potassium hydroxide (0.19 g, 3.30 mmol), potassium fluoride (0.19 g, 3.30 mmol), and tetrabutylammonium iodide (0.11 g, 0.30 mmol) in 1,4-dioxane (1.5 mL) in a seal reactor. Heat the reaction mixture at 100° C. overnight. Cool the reaction mixture to RT. Quench with water. Extract with ethyl acetate, wash the organic layer with water and saturated aqueous sodium chloride. Dry over MgSO₄. After the filtration, remove the reaction solvent under reduced pressure. Purify by FCC (0.1% to 1% 2 M NH₃ methanol solution/CH₂Cl₂) to give the title compound (0.09 g, 20%) with 80% HPLC purity. MS (ES) m/z 279 [M+1]⁺.

PREPARATION 77

[2-(6-Fluoro-4-iodo-pyridin-3-yloxy)-ethyl]methyl-carbamic acid tert-butyl ester Add sodium hydride (620 mg, 26 mmol) to a solution of [2-(6-fluoro-4-iodo-pyridin-3-yloxy)-ethyl]-carbamic acid tert-butyl ester (0.33 g, 0.86 mmol) in 3 mL of DMF. Stir the mixture at RT for 1 h and add methyl iodide (0.37 g, 2.59 mmol). Stir the reaction mixture at RT overnight. Add water and extract with ethyl acetate. Wash the organic layer with saturated aqueous sodium chloride. Dry the mixture over sodium sulfate. Concentrate the solution in vacuo. Purify the residue by column chromatography (20% ethyl acetate in hexane) to afford the title compound as a light yellow solid (0.13 g, 38%). ¹H NMR (400 MHz, CD₃CN) δ 1.45 (s, 9H), 3.08 (s, 3H), 3.59 (t, J=5.6 Hz, 2H), 4.20 (t, J=5.6 Hz, 2H), 5.07 (s, 1H), 7.38 (d, J=3.2 Hz, 1H), 7.61 (d, J=1.2 Hz, 1H).

Prepare the following intermediates with a procedure similar to the one for [2-(6-Fluoro-4-iodo-pyridin-3-yloxy)-ethyl]methyl-carbamic acid tert-butyl ester:

| Prep | Compound Name | MS (ES) m/z [M + 1]⁺ | Comments |
|---|---|---|---|
| 78 | tert-Butyl 1-(6-fluoro-4-iodopyridin-3-yl)ethyl(methyl)carbamate | 381 | Use iodomethane |
| 79 | Ethyl-[1-(6-fluoro-4-iodo-pyridin-3-yl)-ethyl]-carbamic acid tert-butyl ester | 395 | Use iodoethane |

PREPARATION 80

(S)-tert-Butyl 1-(6-fluoro-4-iodopyridin-3-yl)ethyl(methyl)carbamate

Separate tert-butyl 1-(6-fluoro-4-iodopyridin-3-yl)ethyl(methyl)carbamate (3.11 g, 8.48 mmol) by chiral HPLC (4.6× 150 mm Chiralpak® AD-H, 5:95 3A/C7, 0.6 mL/min 270 nm) to give the first fraction as (R)-tert-butyl 1-(6-fluoro-4-iodopyridin-3-yl)ethyl(methyl)carbamate (1.09 g, 35%, >99% ee) and the second fraction as (S)-butyl 1-(6-fluoro-4-iodopyridin-3-yl)ethyl(methyl)carbamate (1.13 g, 36%, >99% ee). MS (ES) m/z 383 [M+1]⁺. Assign the absolute configuration of both enantiomers by a Vibration Circular Dichroic (VCD) spectroscopy study.

Separate the following intermediates with a procedure similar to the one for (S)-tert-Butyl 1-(6-fluoro-4-iodopyridin-3-yl)ethyl(methyl)carbamate:

| Prep | Compound Name | MS (ES) m/z [M + 1]+ |
|---|---|---|
| 81 | (R)-tert-Butyl 1-(6-chloro-4-iodopyridin-3-yl)ethylcarbamate | 383 |
| 82 | (R)-5-(1-Azidoethyl)-2-fluoro-4-iodopyridine | 293 |

PREPARATION 83

4-Benzo[b]thiophen-7-yl-2-chloro-pyridine

In a flask, combine 7-bromo-benzo[b]thiophene (1.7 g, 12 mmol), 2-chloro-4-(4,4,5,5-tetramethyl-[1,3,2]dioxaborolan-2-yl)-pyridine (1.6 g, 7 mmol), Pd(dppf)Cl$_2$ (285 mg, 0.3 mmol), 2-(di-tert-butylphosphino)biphenyl (63 mg, 0.2 mmol), sodium carbonate (2 M, 8 mL, 16 mmol) and THF (20 mL). Heat the mixture at 100° C. for 3 h. Dilute the mixture with chloroform/IPA (3/1). Wash the solution with aqueous saturated sodium chloride. Dry over sodium sulfate. Concentrate the solution in vacuo to a dark residue. Purify by column chromatography (DCM to 20% THF in DCM) to afford the title compound (1.14 g, 66%) as a yellow solid. MS (ES) m/z 246 [M+1]+.

PREPARATION 84

4-Benzo[b]thiophen-7-yl-2-fluoro-5-methyl-pyridine

In a flask, combine 2-fluoro-4-iodo-5-methyl-pyridine (355 mg, 1.5 mmol), 2-benzo[b]thiophen-7-yl-4,4,5,5-tetramethyl-[1,3,2]dioxaborolane (282 mg, 1.8 mmol), Pd(dppf)Cl$_2$ (61 mg, 0.07 mmol), 2-(di-tert-butylphos-phino)biphenyl (13 mg, 0.04 mmol), sodium carbonate (2 M, 1.5 mL, 3 mmol) and THF (10 mL). Heat the mixture at 100° C. for 3 h in an oil bath. Dilute the mixture with chloroform/IPA (3/1). Wash the solution with aqueous saturated sodium chloride. Dry over sodium sulfate. Concentrate in vacuo to a dark residue. Purify by column chromatography (20% ethyl acetate in hexane) to afford the title compound (300 mg, 82%) as a yellow oil. MS (ES) m/z 244 [M+1]+.

Prepare the following intermediates with a procedure similar to the one for 4-Benzo[b]thiophen-7-yl-2-fluoro-5-methyl-pyridine:

| Prep | Compound Name | MS (ES) m/z [M + 1]+ | Comments |
|---|---|---|---|
| 85 | 4-(Benzo[b]thiophen-7-yl)nicotinaldehyde | 240 | |
| 86 | 2-(4-(Benzo[b]thiophen-7-yl)-6-fluoropyridin-3-yl)-2-methylpropanenitrile | 297 | |
| 87 | 4-Benzo[b]thiophen-7-yl-5-cyclopropyl-2-fluoro-pyridine | 270 | dioxane, oil bath |
| 88 | 4-(4-Benzo[b]thiophen-7-yl-6-fluoro-pyridin-3-ylmethyl)-morpholine | 329 | |
| 89 | (4-Benzo[b]thiophen-7-yl-6-fluoro-pyridin-3-ylmethyl)-dimethyl-amine | 287 | |
| 90 | N-(4-Benzo[b]thiophen-7-yl-6-fluoro-pyridin-3-ylmethyl)-methyl-carbamic acid tert-butyl ester | 372 | |
| 91 | N-(4-Benzo[b]thiophen-7-yl-pyridin-3-yl)-2,2-dimethyl-propionamide | 311 | |
| 92 | 4-Benzo[b]thiophen-7-yl-2-chloro-5-methoxymethoxy-pyridine | 306 | |
| 93 | 4-Benzo[b]thiophen-7-yl-2-chloro-5-ethoxy-pyridine | 290 | |
| 94 | 4-Benzo[b]thiophen-7-yl-pyridine | 212 | Heat at 100° C. |

PREPARATION 95

1-(4-(Benzo[b]thiophen-7-yl) pyridin-3-yl)ethanol

Cool a solution of 4-benzo[b]thiophen-7-yl-pyridine-3-carbaldehyde (1.5 g, 6.27 mmol in THF (50 mL) in a 250-mL round bottom flask to 0° C. and add gradually methylmagnesium bromide (2.38 g, 6.90 mmol, 2.30 mL) to the solution. Stir the mixture from 0° C. to RT for 2 h. Hydrolyze the mixture by mixing with 1 N HCl (200 mL). Adjust the pH to 11 with ammonium hydroxide. Extract into chloroform/IPA (3/1, 200 mL). Wash the organic phase with water and saturated aqueous sodium chloride. Dry over sodium sulfate and concentrate in vacuo. Purify by FCC (hexane to 10% ethyl acetate in hexane, then 20% THF in DCM) to give the title compound as a yellow oil (1.00 g, 62%). MS (ES) m/z 256 [M+1]+.

PREPARATION 96

3-(1-Azidoethyl)-4-(benzo[b]thiophen-7-yl) pyridine

Using a procedure similar to the one used for 5-(1-azido-ethyl)-2-fluoro-pyridine above, prepare the title intermediate from 1-(4-(benzo[b]thiophen-7-yl)pyridin-3-yl)ethanol as a brown oil (0.66 g, 93%). MS (ES) m/z 280 [M+1]+.

PREPARATION 97

2-(4-(Benzo[b]thiophen-7-yl)-6-fluoropyridin-3-yl)-2-methylpropan-1-amine

Dissolve sodium tetrahydroborate (296 mg, 7.83 mmol) and zirconium tetrachloride (684 mg, 2.9 mmol) in THF (1 mL) to form a milky solution. Add the solution of 2-(4-benzo[b]thiophen-7-yl-6-fluoro-pyridin-3-yl)-2-methyl-propionitrile (580 mg, 1.96 mmol) in THF (20 mL) under N$_2$ at RT. Stir the mixture at RT overnight. Quench the reaction by pouring the mixture into an ice-water solution. Extract the mixture with chloroform/IPA (3/1). Basify the aqueous phase by adding diluted ammonium hydroxide and filter. Extract the filtrate with chloroform, dry the combined organic phase, and concentrate to give a pale yellow solid (500 mg, 84%). MS (ES) m/z 301 [M+1]+.

PREPARATION 98

1-(4-(Benzo[b]thiophen-7-yl)pyridin-3-yl)ethanamine

Add Raney Nickel (1.38 g, 2.35 mmol) into a solution of 3-(1-azido-ethyl)-4-benzo[b]thiophen-7-yl-pyridine (0.66 g, 2.35 mmol) in ethanol (10 mL), formic acid (1.08 g, 23.54 mmol), and hydrazine (754.4 mg, 23.54 mmol) in a 50-mL round bottom flask in an ice bath. Stir the mixture at RT for 1 h and filter the Raney Nickel. Dilute the filtrate with ammonium hydroxide. Extract the product into chloroform. Wash the organic phase with water, dry over sodium sulfate, and concentrate to give the title compound as a brown oil (0.6 g, 100%). MS (ES) m/z 255 [M+1]$^+$.

Prepare the following intermediates with procedures similar to those described for 1-(4-(Benzo[b]thiophen-7-yl)pyridin-3-yl)ethanamine:

| Prep | Compound Name | MS (ES) m/z [M + 1]$^+$ |
|---|---|---|
| 99 | 1-(6-Fluoro-4-iodopyridin-3-yl)ethanamine | 267 |
| 100 | (R)-1-(4-(Benzo[b]thiophen-7-yl)-6-fluoropyridin-3-yl)ethanamine | 273 |

PREPARATION 101 tert-Butyl 1-(4-(benzo[b]thiophen-7-yl)pyridin-3-yl)ethylcarbamate

Add triethylamine (477.4 mg, 4.72 mmol) to a solution of 1-(4-benzo[b]thiophen-7-yl-pyridin-3-yl)-ethylamine (0.6 g, 2.36 mmol) and di-tert-butyldicarbonate (1.03 g, 4.72 mmol) in 1,4-dioxane (10 mL) and water (5 mL). Stir the mixture at RT for 1 h. Dilute the mixture with chloroform (100 mL), wash with saturated aqueous sodium chloride, dry over sodium sulfate, and concentrate. Purify the residue by FCC (20% ethyl acetate in hexane to 10% methanol in DCM) to give the title compound as a yellow solid (0.84 g, 67%). MS (ES) m/z 355 [M+1]$^+$.

Prepare the following intermediates with procedures similar to those described for tert-Butyl 1-(4-(benzo[b]thiophen-7-yl)pyridin-3-yl)ethylcarbamate:

| Prep | Compound Name | MS (ES) m/z [M + 1]$^+$ |
|---|---|---|
| 102 | tert-Butyl 1-(6-fluoro-4-iodopyridin-3-yl)ethylcarbamate | 367 |
| 103 | tert-Butyl 2-(4-(benzo[b]thiophen-7-yl)-6-fluoropyridin-3-yl)-2-methylpropylcarbamate | 401 |
| 104 | (R)-tert-Butyl 1-(4-(benzo[b]thiophen-7-yl)-6-fluoropyridin-3-yl)ethylcarbamate | 373 |

PREPARATION 105 tert-Butyl 1-(6-fluoro-4-iodopyridin-3-yl)ethyl(2-fluoroethyl)carbamate

Add sodium hydride (58.9 mg, 2.46 mmol) to a solution of [1-(6-fluoro-4-iodo-pyridin-3-yl)-ethyl]-carbamic acid tert-butyl ester (300 mg, 819 μmol) at 0° C. Stir the mixture at 0° C. to RT for 1 h. Add 1-fluoro-2-iodo-ethane (570 mg, 3.28 mmol). Stir the mixture at RT for 4 h and then at 50° C. overnight. Dilute the mixture with chloroform/IPA (3/1, 100 mL) and wash with water/aqueous saturated sodium chloride. Dry the organic phase over sodium sulfate and concentrate in vacuo to give the crude product. Purify the crude product by FCC (20% ethyl acetate in hexane) to give 140 mg of the title compound (41%). MS (ES) m/z 413 [M+1]$^+$.

PREPARATION 106

4-Benzo[b]thiophen-7-yl-3-methoxymethoxy-pyridine

Solution A: Treat a solution of 3-methoxymethoxy-pyridine (2.5 g, 18 mmol) in diethyl ether (90 mL) at −70° C. with tert-butyl lithium (1.7 M in pentane, 10 mL, 18 mmol) dropwise over 10 min. Stir the mixture at −70° C. for 40 min and add a solution of triisopropyl borate (5 mL, 22 mmol) in THF (10 mL) dropwise over 5 min. Stir the mixture at −70° C. for 1 h and then remove the ice bath and allow the mixture to slowly warm to RT.

Solution B: Treat a solution of 7-bromo-benzo[b]thiophene (3.8 g, 18 mmol), 2-(di-tert-butylphosphino)biphenyl (268 mg, 0.90 mmol), Pd(dppf)Cl$_2$ (732 mg, 0.90 mmol) in 1,4-dioxane (30 mL) with 2 M aqueous sodium carbonate (72 mL, 36 mmol). Heat the solution to 80° C. once solution A reaches RT.

Treat solution B with solution A dropwise over 10 min. Heat the combined solution to 85° C. for 5 h. Cool the mixture to RT and dilute with ethyl acetate and water. Wash the organic phase with water and aqueous saturated sodium chloride, dry over sodium sulfate, filter, and concentrate in vacuo. Purify the residue by column chromatography on 120 g silica gel eluting with a gradient of DCM to ethyl acetate to give the title compound (3.8 g) containing some starting 3-methoxymethoxy-pyridine. $^1$H NMR (400 MHz, CDCl$_3$) δ 8.68 (s, 1H), 8.42 (d, J=4 Hz, 1H), 7.88 (d, J=8 Hz, 1H), 7.33-7.50 (m, 5H), 5.12 (s, 2H), 3.36 (s, 3H).

PREPARATION 107

2-Chloro-4-[7-(2-chloro-pyridin-4-yl)-benzo[b]thiophen-2-yl]-pyrimidine

In a 500 mL round bottom flask, cool a solution of 4-benzo[b]thiophen-7-yl-2-chloro-pyridine (13 g, 53.1 mmol) and triisopropylborate (20 g, 106 mmol) in THF (150 mL) to −70° C. under nitrogen. To the cooled solution, add lithium diisopropylamide (2 M in THF, 53 mL, 106 mmol) gradually over a period of 30 min. Stir the mixture continually for an additional hour in the cooling bath. Gradually transfer the mixture into a refluxing solution of 2,4-dichloro-pyrimidine (12 g, 106 mmol), Pd(dppf)Cl$_2$ (2.2 g, 53 mmol) and sodium carbonate (35 mL, 3 M, 106 mmol) in THF (150 mL) over a period of 30 min. Reflux for an additional 1 h. Cool the mixture to RT and dilute with 500 mL of chloroform/IPA (3/1) and 200 mL of water. Collect the resulting solid by filtration and reserve the chloroform/IPA/water mixture. Wash the solid with DCM and dry it under vacuum. Separate the layers of the chloroform/IPA/water mixture. Wash the organic phase with water and aqueous saturated sodium chloride, dry over sodium sulfate and concentrate in vacuo to give a brown residue. Purify the residue by FCC (10% methanol in DCM) to afford additional product. Combine the two portions to give the title compound (13 g, 68%). MS (ES) m/z 358 [M+1]$^+$.

Prepare the following intermediates essentially according to the preparation of 2-Chloro-4-[7-(2-chloro-pyridin-4-yl)-benzo[b]thiophen-2-yl]-pyrimidine using the appropriate starting material:

| Prep | Compound Name | MS (ES) m/z [M + 1]$^+$ | Comments |
|---|---|---|---|
| 108 | 2-Chloro-5-fluoro-4-[7-(2-fluoro-5-methyl-pyridin-4-yl)-benzo[b]thiophen-2-yl]-pyrimidine | 374 | |

-continued

| Prep | Compound Name | MS (ES) m/z [M + 1]+ | Comments |
|---|---|---|---|
| 109 | 2-Chloro-4-[7-(2-fluoro-5-methyl-pyridin-4-yl)-benzo[b]thiophen-2-yl]-pyrimidine | 356 | Use 3 mole % of 2-(di-tert-butyl phosphino) biphenyl |
| 110 | 2-Chloro-4-[7-(5-cyclopropyl-2-fluoro-pyridin-4-yl)-benzo[b]thiophen-2-yl]-5-fluoro-pyrimidine | 400 | |
| 111 | 4-{4-[2-(2-Chloro-5-fluoro-pyrimidin-4-yl)-benzo[b]thiophen-7-yl]-6-fluoro-pyridin-3-ylmethyl}-morpholine | 459 | |
| 112 | {4-[2-(2-Chloro-5-fluoro-pyrimidin-4-yl)-benzo[b]thiophen-7-yl]-6-fluoro-pyridin-3-ylmethyl}-dimethyl-amine | 417 | |
| 113 | (4-[2-(2-Chloro-5-fluoro-pyrimidin-4-yl)-benzo[b]thiophen-7-yl]-6-fluoro-pyridin-3-ylmethyl}-methyl-carbamic acid tert-butyl ester | 502 | |
| 114 | N-{4-[2-(2-Chloro-5-fluoro-pyrimidin-4-yl)-benzo[b]thiophen-7-yl]-pyridin-3-yl}-2,2-dimethyl-propionamide | 441 | |
| 115 | 2-Chloro-5-fluoro-4-[7-(3-methoxymethoxy-pyridin-4-yl)-benzo[b]thiophen-2-yl]-pyrimidine | 420 | |
| 116 | 2-Chloro-4-[7-(2-chloro-5-ethoxy-pyridin-4-yl)-benzo[b]thiophen-2-yl]-5-fluoro-pyrimidine | 402 | |
| 117 | 2-Chloro-4-[7-(2-chloro-5-methoxymethoxy-pyridin-4-yl)-benzo[b]thiophen-2-yl]-5-fluoro-pyrimidine | 436 | |
| 118 | 2-Chloro-5-fluoro-4-(7-pyridin-4-yl-benzo[b]thiophen-2-yl)-pyrimidine | 342 | |
| 119 | 4-(7-Bromo-benzo[b]thiophen-2-yl)-2-chloro-5-fluoro-pyrimidine | 476 | |
| 120 | 4-(7-Bromobenzo[b]thiophen-2-yl)-2,5-dichloropyrimidine | 359 | |
| 121 | 4-(7-Bromobenzo[b]thiophen-2-yl)-2-chloro-5-methylpyrimidine | 339 | |
| 122 | 4-(7-Bromobenzo[b]thiophen-2-yl)-2-chloropyrimidine | 325 | |
| 123 | tert-Butyl 1-(4-(2-(2-chloro-5-fluoropyrimidin-4-yl)benzo[b]thiophen-7-yl)pyridin-3-yl)ethylcarbamate | 485 | |
| 124 | tert-Butyl 2-(4-(2-(2-chloro-5-fluoropyrimidin-4-yl)benzo[b]thiophen-7-yl)-6-fluoropyridin-3-yl)-2-methylpropylcarbamate | 531 | |
| 125 | (R)-tert-Butyl 1-(4-(2-(2-chloro-5-fluoropyrimidin-4-yl)benzo[b]thiophen-7-yl)-6-fluoropyridin-3-yl)ethylcarbamate | 503 | |

PREPARATION 126

4-[2-(2-Chloro-5-fluoro-pyrimidin-4-yl)-benzo[b]thiophen-7-yl]-pyridin-3-ol

Treat a solution of 2-chloro-5-fluoro-4-[7-(3-methoxymethoxy-pyridin-4-yl)-benzo[b]thiophen-2-yl]-pyrimidine (4 g, 10 mmol) in THF (10 mL) with 5 N HCl (3 mL). Stir the mixture at RT for 6 h. Concentrate the reaction in vacuo and dilute with saturated aqueous sodium bicarbonate and DCM. Separate the phases and filter each phase. Wash the solid from the organic phase with DCM to give the title compound (300 mg) as a tan solid. Wash the solid from the aqueous layer with water and dry to give the title compound (300 mg) as a tan solid. Combine the solids to give the title compound (600 mg; 17%) as a tan solid. MS (ES) m/z 358 [M+1]+.

Prepare the following intermediate with a procedure similar to the one for 4-[2-(2-Chloro-5-fluoro-pyrimidin-4-yl)-benzo[b]thiophen-7-yl]-pyridin-3-ol using the appropriate starting material:

| Prep | Compound Name | MS (ES) m/z [M + 1]+ |
|---|---|---|
| 127 | 6-Chloro-4-[2-(2-chloro-5-fluoro-pyrimidin-4-yl)-benzo[b]thiophen-7-yl]-pyridin-3-ol | 392 |

PREPARATION 128

2-(2-(5-(Hydroxymethyl)-1H-1,2,3-triazol-1-yl)ethyl)isoindoline-1,3-dione

Heat a mixture of 2-(2-azidoethyl)isoindoline-1,3-dione (12 g, 55.5 mmol) and 2-propyn-1-ol (3.88 mL, 66.6 mmol) in toluene (50 mL) in a sealed reactor at 90° C. for 3 days. Cool to RT and collect the solid. Purify by column chromatography (DCM to 2% methanol in DCM) to afford the title compound (first fraction) as a white solid (4.7 g, 31%). MS (EI) m/z 273 [M+1]+.

PREPARATION 129

2-(2-(4-(Iodomethyl)-1H-1,2,3-triazol-1-yl)ethyl) isoindoline-1,3-dione

Stir a mixture of triphenylphosphine (0.29 g, 1.10 mmol) and iodine (0.28 g, 1.10 mmol) in DCM (4 mL) for 10 min. Add 1H-imidazole (0.12 g, 1.84 mmol) and stir for 10 min. Add 2-(2-(4-(hydroxymethyl)-1H-1,2,3-triazol-1-yl) ethyl) isoindoline-1,3-dione (0.2 g, 0.73 mmol) and stir overnight at RT. Dilute with DCM and wash with water and saturated aqueous sodium chloride. Dry over sodium sulfate. Concentrate the solution in vacuo. Purify by column chromatography (DCM to 20% ethyl acetate in DCM) to afford the title compound as a yellow solid (0.22 g, 78%). MS (EI) m/z 383 [M+1]$^+$.

PREPARATION 130

2-(2-(4-Methyl-1H-1,2,3-triazol-1-yl)ethyl) isoindoline-1,3-dione

Stir a mixture of 2-(2-(4-(iodomethyl)-1H-1,2,3-triazol-1-yl)ethyl) isoindoline-1,3-dione (1 g, 2.62 mmol) and 0.2 g of 10% palladium on carbon in ethanol (10 mL) under a hydrogen balloon overnight. Filter to remove the solid and concentrate. Purify by column chromatography (DCM to 20% ethyl acetate in DCM) to afford the title compound as a yellow solid (0.5 g, 74%). MS (EI) m/z 257 [M+1]$^+$.

PREPARATION 131

2-(2-[1,2,3]Triazol-1-yl-ethyl)-isoindole-1,3-dione

Add 1H-1,2,3-triazole (250 g, 3.51 mol), N-(2-bromoethyl) phthalimide (942 g, 3.52 mol) and 1500 mL of DMF to a 5-L round bottom flask fitted with a mechanical stirrer, a nitrogen inlet and temperature probe; cool the mixture to 15° C. Stir the mixture until all the solids are nearly dissolved and then cool in an ice-water bath. Add cesium carbonate (1145 g, 3.51 mol) in portions over 10 min. The reaction mixture exotherms to 21° C. Allow the mixture to stir and come to RT overnight. Pour the reaction mixture into a 12-L flask containing 8 L of ice-water. Stir the suspension for 30 min and then filter and rinse the solid with 3 L of water. Air-dry for 2 h. Recrystallize the mixture of regioisomers from 7 L of absolute ethanol. Isolate the solid by filtration and air-dry. Recrystallize again from 16 L of absolute ethanol. Again isolate the solid by filtration and rinse with fresh ethanol (1000 mL). Vacuum-dry the solid at 40° C. to give the title compound as a white solid, 292.7 g (34%). MS (EI) m/z 243 [M+1]$^+$.

PREPARATION 132

2-[1,2,3]Triazol-1-yl-ethylamine

Dissolve 2-(2-[1,2,3]triazol-1-yl-ethyl)-isoindole-1,3-dione (106 g, 437.59 mmol) in a 5-L roundbottom flask containing 2 L of absolute ethanol. Heat the stirred mixture to 70° C. under nitrogen; at this temperature add dropwise hydrazine monohydrate (23 mL, 463.76 mmol) over 10 min. The mixture becomes homogeneous and yellow in color. After about 30 min at this temperature a solid begins to form in the reaction and the color gradually becomes much less yellow over time. After 7 h remove the heat and warm to RT over 1 h. Filter over diatomaceous earth and rinse with 1000 mL of ethanol. Evaporate to a semi-solid. Dissolve in 2 L of $CH_2Cl_2$, filter over diatomaceous earth and evaporate again. Dilute the residue with toluene (1500 mL) and filter over diatomaceous earth to remove the insoluble tan solid. Evaporate and place under vacuum overnight. Dissolve the oil in 100 mL of $CH_2Cl_2$ and filter again through a pad of diatomaceous earth. Evaporate to give 43.9 g (90%) of the title compound as a cloudy oil. MS (ES) m/z 112 [M+1]$^+$.

Prepare the following intermediates with procedures similar to those described for 2-[1,2,3]Triazol-1-yl-ethylamine:

| Prep | Compound Name | MS (ES) m/z [M + 1]$^+$ |
|---|---|---|
| 133 | (1-(2-Aminoethyl)-1H-1,2,3-triazol-5-yl)methanol | 143 |
| 134 | 2-(4-Methyl-1H-1,2,3-triazol-1-yl)ethanamine | 127 |

Prepare the following intermediates with procedures similar to the one for {5-Fluoro-4-[7-(2-fluoro-5-methyl-pyridin-4-yl)-benzo[b]thiophen-2-yl]-pyrimidin-2-yl}-(2-[1,2,3] triazol-1-yl-ethyl)-amine below:

| Prep | Compound Name | MS (ES) m/z [M + 1]$^+$ | Comments |
|---|---|---|---|
| 135 | (6-Fluoro-4-{2-[5-fluoro-2-(2-[1,2,3]triazol-1-yl-ethylamino)-pyrimidin-4-yl]-benzo[b]thiophen-7-yl}-pyridin-3-ylmethyl)-methyl-carbamic acid tert-butyl ester | 578 | |
| 136 | [4-(7-Bromo-benzo[b]thiophen-2-yl)-5-fluoro-pyrimidin-2-yl]-(2-[1,2,3]triazol-1-yl-ethyl)-amine | 419, 421 | |
| 137 | N-(2-(1H-1,2,3-Triazol-1-yl)ethyl)-4-(7-bromobenzo[b]thiophen-2-yl)pyrimidin-2-amine | 401, 403 | |
| 138 | N-(2-(1H-1,2,3-Triazol-1-yl)ethyl)-4-(7-bromobenzo[b]thiophen-2-yl)-5-chloropyrimidin-2-amine | 435, 437 | |
| 139 | N-(2-(1H-1,2,3-Triazol-1-yl)ethyl)-4-(7-bromobenzo[b]thiophen-2-yl)-5-methylpyrimidin-2-amine | 415, 417 | |
| 140 | N-(2-(1H-1,2,3-Triazol-1-yl)ethyl)-4-(7-(3-(1-aminoethyl)pyridin-4-yl)benzo[b]thiophen-2-yl)-5-fluoropyrimidin-2-amine | 461 | In situ TFA removal of Boc (t-butyl-carbamate protection) group |

-continued

| Prep | Compound Name | MS (ES) m/z [M + 1]+ | Comments |
|---|---|---|---|
| 141 | (R)-tert-Butyl 1-(6-fluoro-4-(2-(5-fluoro-2-(2-(5-(hydroxymethyl)-1H-1,2,3-triazol-1-yl)ethylamino)pyrimidin-4-yl)benzo[b]thiophen-7-yl)pyridin-3-yl)ethylcarbamate | 609 | From chiral intermediate |
| 142 | (R)-tert-Butyl 1-(6-fluoro-4-(2-(5-fluoro-2-(2-(4-methyl-1H-1,2,3-triazol-1-yl)ethylamino)pyrimidin-4-yl)benzo[b]thiophen-7-yl)pyridin-3-yl)ethylcarbamate | 593 | From chiral intermediate |

PREPARATION 143

{5-Fluoro-4-[7-(4,4,5,5-tetramethyl-[1,3,2]dioxaborolan-2-yl)-benzo[b]thiophen-2-yl]-pyrimidin-2-yl}-(2-[1,2,3]triazol-1-yl-ethyl)-amine Combine [4-(7-bromo-benzo[b]thiophen-2-yl)-5-fluoro-pyrimidin-2-yl]-(2-[1,2,3]triazol-1-yl-ethyl)-amine (1.5 g, 3.45 mmol), bis(pinacolato)diboron (1.05 g, 4.14 mmol), potassium acetate (1.02 g, 10.36 mmol), and Pd(dppf)Cl$_2$ (280 mg, 0.35 mmol) in DMSO (30 mL). Degas the resulting mixture three times and heat it to 80° C. overnight. Cool the mixture to RT and pour it into water. Filter to get a wet solid, dissolve in chloroform/IPA (3:1, v/v), wash with saturated aqueous sodium chloride and then dry over sodium sulfate. Concentrate the solution in vacuo. Purify by chromatography (hexane to ethyl acetate) to afford the title compound (1.3 g, 81%).

Prepare the following intermediates by using procedures essentially similar to those used for the intermediate above:

| Prep | Compound Name | MS (ES) m/z [M + 1]+ |
|---|---|---|
| 144 | N-(2-(1H-1,2,3-Triazol-1-yl)ethyl)-5-chloro-4-(7-(4,4,5,5-tetramethyl-1,3,2-dioxaborolan-2-yl)benzo[b]thiophen-2-yl)pyrimidin-2-amine | 483 |
| 145 | N-(2-(1H-1,2,3-Triazol-1-yl)ethyl)-5-methyl-4-(7-(4,4,5,5-tetramethyl-1,3,2-dioxaborolan-2-yl)benzo[b]thiophen-2-yl)pyrimidin-2-amine | 463 |
| 146 | N-(2-(1H-1,2,3-Triazol-1-yl)ethyl)-4-(7-(4,4,5,5-tetramethyl-1,3,2-dioxaborolan-2-yl)benzo[b]thiophen-2-yl)pyrimidin-2-amine | 449 |

Prepare the following intermediates with procedures similar to the one for N-(2-(1H-1,2,3-Triazol-1-yl)ethyl)-4-(7-(1H-pyrrolo[2,3-b]pyridin-4-yl)benzo[b]thiophen-2-yl)-5-fluoropyrimidin-2-amine below:

| Prep | Compound Name | MS (ES) m/z [M + 1]+ | Comments |
|---|---|---|---|
| 147 | (4-{7-[5-(1-Azido-ethyl)-2-fluoro-pyridin-4-yl]-benzo[b]thiophen-2-yl}-5-fluoro-pyrimidin-2-yl)-(2-[1,2,3]triazol-1-yl-ethyl)-amine | 505 | |
| 148 | (5-Fluoro-4-{7-[2-fluoro-5-(1-methoxymethoxy-ethyl)-pyridin-4-yl]-benzo[b]thiophen-2-yl}-pyrimidin-2-yl)-(2-[1,2,3]triazol-1-yl-ethyl)-amine | 524 | |
| 149 | [5-Fluoro-4-(7-{2-fluoro-5-[2-(tetrahydro-pyran-2-yloxy)-ethoxy]-pyridin-4-yl}-benzo[b]thiophen-2-yl)-pyrimidin-2-yl]-(2-[1,2,3]triazol-1-yl-ethyl)-amine | 580 | |
| 150 | (R)-N-(2-(1H-1,2,3-Triazol-1-yl)ethyl)-4-(7-(5-(1-azidoethyl)-2-fluoropyridin-4-yl)benzo[b]thiophen-2-yl)pyrimidin-2-amine | 487 | |
| 151 | 2-[2-(6-Fluoro-4-{2-[5-fluoro-2-(2-[1,2,3]triazol-1-yl-ethylamino)-pyrimidin-4-yl]-benzo[b]thiophen-7-yl}-pyridin-3-yloxy)-ethyl]-isoindole-1,3-dione | 625 | |
| 152 | [2-(6-Fluoro-4-{2-[5-fluoro-2-(2-[1,2,3]triazol-1-yl-ethylamino)-pyrimidin-4-yl]-benzo[b]thiophen-7-yl}-pyridin-3-yloxy)-ethyl]-methyl-carbamic acid tert-butyl ester | 609 | |
| 153 | (R)-2-(1-(4-(2-(2-(1H-1,2,3-Triazol-1-yl)ethylamino)-5-fluoropyrimidin-4-yl)benzo[b]thiophen-7-yl)-6-fluoropyridin-3-yloxy)propan-2-yl)isoindoline-1,3-dione | 639 | |
| 154 | (S)-2-(1-(4-(2-(2-(1H-1,2,3-Triazol-1-yl)ethylamino)-5-fluoropyrimidin-4-yl)benzo[b]thiophen-7-yl)-6-fluoropyridin-3-yloxy)propan-2-yl)isoindoline-1,3-dione | 639 | |

-continued

| Prep | Compound Name | MS (ES) m/z [M + 1]+ | Comments |
|---|---|---|---|
| 155 | tert-Butyl 1-(4-(2-(2-(2-(1H-1,2,3-triazol-1-yl)ethylamino)-5-methylpyrimidin-4-yl)benzo[b]thiophen-7-yl)-6-chloropyridin-3-yl)ethylcarbamate | 592 | |
| 156 | tert-Butyl 1-(4-(2-(2-(2-(1H-1,2,3-triazol-1-yl)ethylamino)pyrimidin-4-yl)benzo[b]thiophen-7-yl)-6-chloropyridin-3-yl)ethyl(methyl)carbamate | 592 | |
| 157 | tert-Butyl 1-(4-(2-(2-(2-(1H-1,2,3-triazol-1-yl)ethylamino)-5-fluoropyrimidin-4-yl)benzo[b]thiophen-7-yl)-6-fluoropyridin-3-yl)ethylcarbamate | 579 | |
| 158 | N-(2-(1H-1,2,3-Triazol-1-yl)ethyl)-4-(7-(2-chloro-5-(2-(tetrahydro-2H-pyran-2-yloxy)ethoxy)pyridin-4-yl)benzo[b]thiophen-2-yl)-5-fluoropyrimidin-2-amine | 596 | Conditions similar to example 17 |
| 159 | tert-Butyl 4-(1-(4-(2-(2-(1H-1,2,3-triazol-1-yl)ethylamino)-5-fluoropyrimidin-4-yl)benzo[b]thiophen-7-yl)-6-chloropyridin-3-yl)ethyl)piperazine-1-carboxylate | 664 | Conditions similar to example 17 |
| 160 | tert-Butyl 1-(4-(2-(2-(2-(1H-1,2,3-triazol-1-yl)ethylamino)-5-fluoropyrimidin-4-yl)benzo[b]thiophen-7-yl)-6-methylpyridin-3-yl)ethylcarbamate | 575 | Conditions similar to example 17 |

EXAMPLE 1

N-(2-(1H-1,2,3-Triazol-1-yl)ethyl)-5-fluoro-4-(7-(2-fluoro-5-methylpyridin-4-yl)benzo[b]thiophen-2-yl)pyrimidin-2-amine

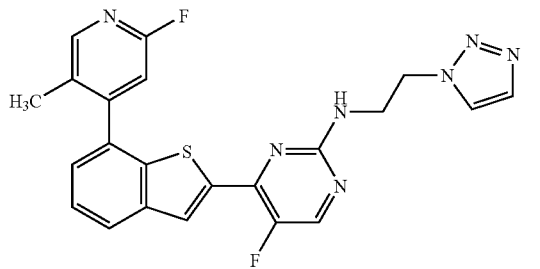

Combine 2-chloro-5-fluoro-4-[7-(2-fluoro-5-methyl-pyridin-4-yl)-benzo[b]thiophen-2-yl]-pyrimidine (200 mg, 0.54 mmol) and 2-[1,2,3]triazol-1-yl-ethylamine (120 mg, 21.1 mmol) in n-butanol (2 mL), alternative dioxane, dioxane-NMP (N-methylpyrrolidinone), NMP alone as solvent] in a pressure vessel. Heat the mixture in an oil bath at 120-150° C. overnight (or in microwave reactor for 10-60 min). Dilute the mixture with chloroform/IPA (3/1). Wash the solution with saturated aqueous sodium chloride, dry over sodium sulfate, and concentrate the solution in vacuo to a dark residue. Purify by column chromatography (DCM→10% methanol in DCM) to afford the title compound as a yellow solid (140 mg, 59%). MS (ES) m/z 450 [M+1]+.

Prepare the following examples with procedures similar to the one for the example above:

| Ex | Compound structure | Compound Name | MS (ES) m/z [M + 1]+ | Comments |
|---|---|---|---|---|
| 2 | 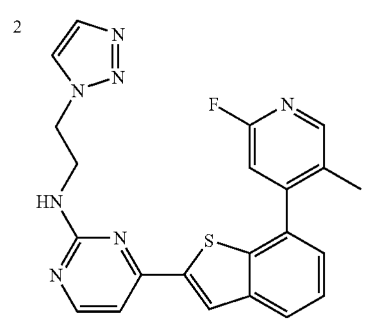 | N-(2-(1H-1,2,3-Triazol-1-yl)ethyl)-4-(7-(2-fluoro-5-methylpyridin-4-yl)benzo[b]thiophen-2-yl)pyrimidin-2-amine | 432 | 3 equivalents triethyl amine used |

| Ex | Compound structure | Compound Name | MS (ES) m/z [M + 1]⁺ | Comments |
|---|---|---|---|---|
| 3 | 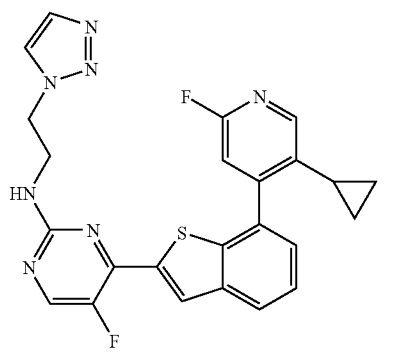 | N-(2-(1H-1,2,3-Triazol-1-yl)ethyl)-4-(7-(5-cyclopropyl-2-fluoropyridin-4-yl)benzo[b]thiophen-2-yl)-5-fluoropyrimidin-2-amine | 476 | |
| 4 | 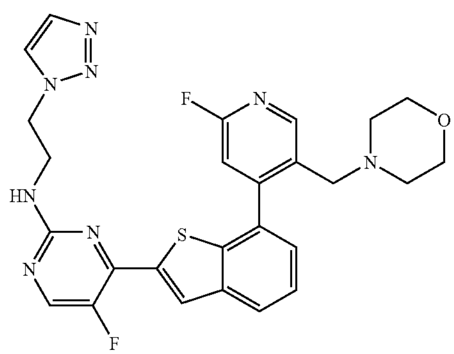 | N-(2-(1H-1,2,3-Triazol-1-yl)ethyl)-5-fluoro-4-(7-(2-fluoro-5-(morpholinomethyl)pyridin-4-yl)benzo[b]thiophen-2-yl)pyrimidin-2-amine | 534 | |
| 5 | 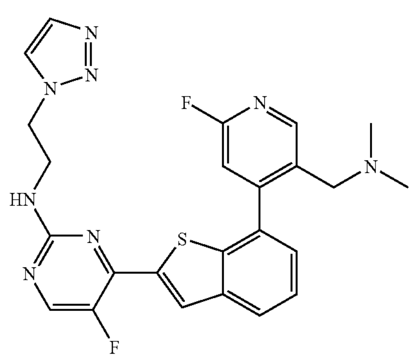 | N-(2-(1H-1,2,3-Triazol-1-yl)ethyl)-4-(7-(5-((dimethylamino)methyl)-2-fluoropyridin-4-yl)benzo[b]thiophen-2-yl)-5-fluoropyrimidin-2-amine | 492 | |
| 6 | 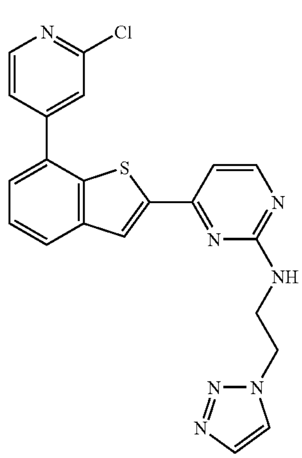 | N-(2-(1H-1,2,3-Triazol-1-yl)ethyl)-4-(7-(2-chloropyridin-4-yl)benzo[b]thiophen-2-yl)pyrimidin-2-amine | 434 | |

| Compound Ex structure | Compound Name | MS (ES) m/z [M + 1]+ | Comments |
|---|---|---|---|
| 7 | N-(2-(1H-1,2,3-Triazol-1-yl)ethyl)-4-(7-(3-aminopyridin-4-yl)benzo[b]thiophen-2-yl)-5-fluoropyrimidin-2-amine | 433 | |
| 8 | 4-(2-(2-(2-(1H-1,2,3-Triazol-1-yl)ethylamino)-5-fluoropyrimidin-4-yl)benzo[b]thiophen-7-yl)pyridin-3-ol | 434 | |
| 9 | 4-(2-(2-(2-(1H-1,2,3-Triazol-1-yl)ethylamino)-5-fluoropyrimidin-4-yl)benzo[b]thiophen-7-yl)-6-chloropyridin-3-ol | 468 | |

| Ex | Compound structure | Compound Name | MS (ES) m/z [M + 1]+ | Comments |
|---|---|---|---|---|
| 10 | 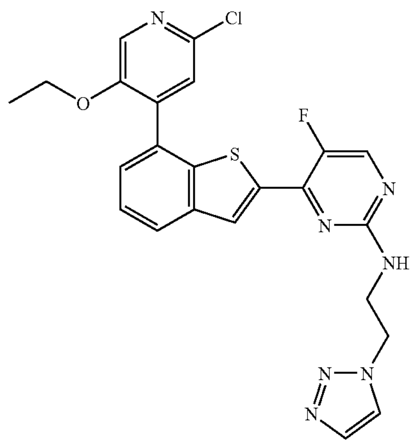 | N-(2-(1H-1,2,3-Triazol-1-yl)ethyl)-4-(7-(2-chloro-5-ethoxypyridin-4-yl)benzo[b]thiophen-2-yl)-5-fluoropyrimidin-2-amine | 496 | |
| 11 | 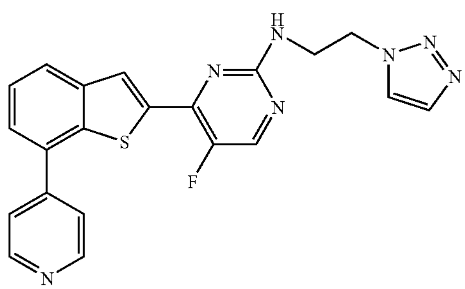 | N-(2-(1H-1,2,3-Triazol-1-yl)ethyl)-5-fluoro-4-(7-(pyridin-4-yl)benzo[b]thiophen-2-yl)pyrimidin-2-amine | 418 | |
| 12 | 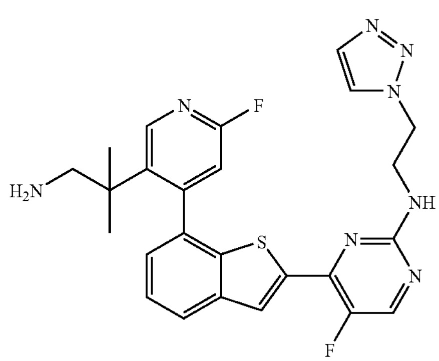 | N-(2-(1H-1,2,3-Triazol-1-yl)ethyl)-4-(7-(5-(1-amino-2-methylpropan-2-yl)-2-fluoropyridin-4-yl)benzo[b]thiophen-2-yl)-5-fluoropyrimidin-2-amine | 507 | In situ TFA removal of Boc group |

EXAMPLE 13

N-(2-(1H-1,2,3-Triazol-1-yl)ethyl)-5-fluoro-4-(7-(2-fluoro-5-((methylamino)methyl)pyridin-4-yl)benzo[b]thiophen-2-yl)pyrimidin-2-amine

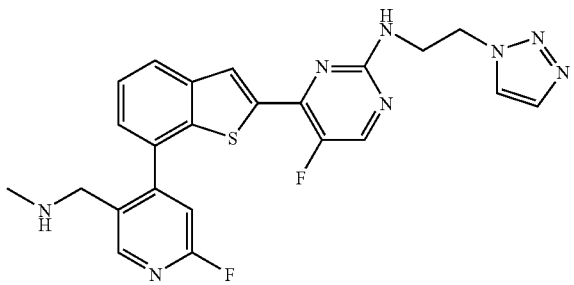

Combine (6-fluoro-4-{2-[5-fluoro-2-(2-[1,2,3]triazol-1-yl-ethylamino)-pyrimidin-4-yl]-benzo[b]thiophen-7-yl}-pyridin-3-ylmethyl)-methyl-carbamic acid tert-butyl ester (0.30 g, 0.51 mmol) and dry TFA (2.0 mL) and dry DCM (2.2 mL). Stir at RT for 1 h. Evaporate off the solvents. Dilute the resulting residue with DCM and wash with saturated sodium bicarbonate solution, water, and saturated aqueous sodium chloride. Separate the organic layer and dry over magnesium sulfate. Filter and concentrate in vacuo to give the crude product. Purify by column chromatography [0.1% to 2% 2 M ammonia in methanol/DCM] to afford the title compound (0.20 g, 83%). MS (ES) m/z 479 [M+1]$^+$.

EXAMPLE 14

N-(2-(1H-1,2,3-Triazol-1-yl)ethyl)-5-fluoro-4-(7-(5-fluoro-1H-pyrrolo[2,3-b]pyridin-4-yl)benzo[b]thiophen-2-yl)pyrimidin-2-amine

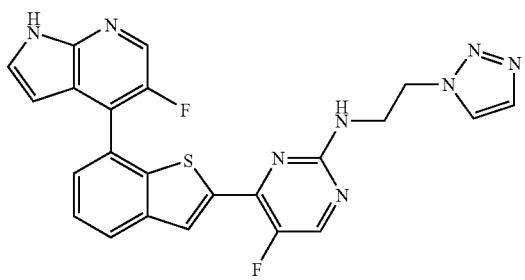

Combine {5-fluoro-4-[7-(4,4,5,5-tetramethyl-[1,3,2]dioxaborolan-2-yl)-benzo[b]thiophen-2-yl]-pyrimidin-2-yl}-(2-[1,2,3]triazol-1-yl-ethyl)-amine (0.105 g, 0.23 mmol), 3-fluoro-4-bromo-1H-pyrrolo[2,3-b]pyridine (51 mg, 0.30 mmol), barium hydroxide octahydrate (0.21 g, 0.68 mmol, alternatively sodium carbonate, potassium carbonate, sodium bicarbonate), Pd(dppf)Cl$_2$ (20 mg, 0.025 mmol) in 2 mL of mixed solvent of DMF (alternatively dioxane, THF, DMSO, and CH$_3$CN) and water (4/1, v/v). Heat the reaction mixture to 80° C. for 2.5 h. (or microwave heating for 10-60 min). Cool to RT. Dilute it with chloroform/IPA (3:1, v/v) 50 mL. Wash it with water and saturated aqueous sodium chloride and dry over magnesium sulfate. Remove the organic solvent to give the crude product. Purify by column chromatography (hexane to ethyl acetate) to afford the title compound (0.05 g, 47%). MS (ES) m/z 475 [M+1]$^+$.

EXAMPLE 15

N-(2-(1H-1,2,3-Triazol-1-yl)ethyl)-4-(7-(1H-pyrrolo[2,3-b]pyridin-4-yl)benzo[b]thiophen-2-yl)-5-fluoro-pyrimidin-2-amine

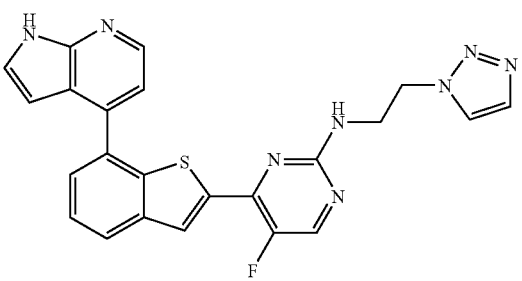

Combine N-(2-(1H-1,2,3-triazol-1-yl)ethyl)-5-fluoro-4-(7-(4,4,5,5-tetramethyl-1,3,2-dioxaborolan-2-yl)benzo[b]thiophen-2-yl)pyrimidin-2-amine (0.28 g, 0.6 mmol), 4-bromo-1H-pyrrolo[2,3-b]pyridine (100 mg, 0.51 mmol), barium hydroxide octahydrate (0.48 g, 1.52 mmol), Pd(dppf)Cl$_2$ (40 mg, 0.05 mmol) in 4 mL of mixed solvent of DMF and water (4/1, v/v). Heat the reaction mixture to 80° C. for 45 min. Cool to RT. Dilute with chloroform/IPA (3:1, v/v) 50 mL. Wash with water and saturated aqueous sodium chloride and dry over magnesium sulfate. Remove the organic solvent to give the crude product. Purify by column chromatography (hexane to ethyl acetate) to afford the title compound (0.17 g, 75%). MS (ES) m/z 457 [M+1]$^+$.

Prepare the following examples with procedures similar to the one for the example above:

| Ex | Compound structure | Compound Name | MS (ES) m/z [M + 1]$^+$ | Comments |
|---|---|---|---|---|
| 16 | 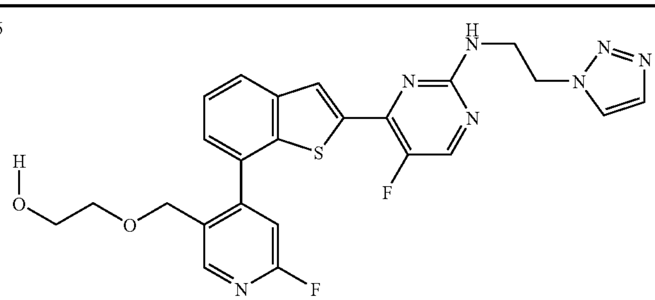 | 2-((4-(2-(2-(2-(1H-1,2,3-Triazol-1-yl)ethylamino)-5-fluoropyrimidin-4-yl)benzo[b]thiophen-7-yl)-6-fluoropyridin-3-yl)methoxy)ethanol | 510 | |

| Ex | Compound structure | Compound Name | MS (ES) m/z [M + 1]+ | Comments |
|---|---|---|---|---|
| 17 | 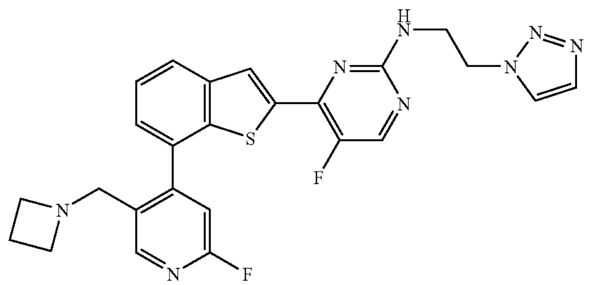 | N-(2-(1H-1,2,3-Triazol-1-yl)ethyl)-4-(7-(5-(azetidin-1-ylmethyl)-2-fluoropyridin-4-yl)benzo[b]thiophen-2-yl)-5-fluoropyrimidin-2-amine | 505 | At 100° C. and 10 min. Pd(dppf)Cl$_2$ and 2-(di-tert-butylphosphino)biphenyl used as catalyst and ligand. Normal phase followed by reverse phase for purification. |
| 18 | 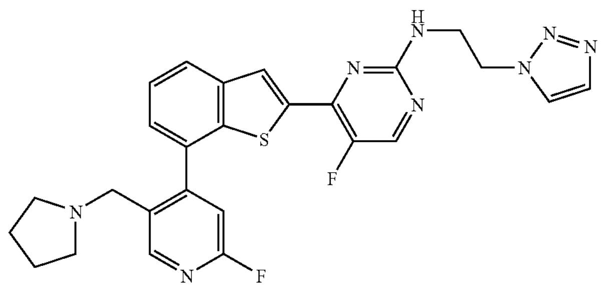 | N-(2-(1H-1,2,3-Triazol-1-yl)ethyl)-5-fluoro-4-(7-(2-fluoro-5-(pyrrolidin-1-ylmethyl)pyridin-4-yl)benzo[b]thiophen-2-yl)pyrimidin-2-amine | 519 | Conditions similar to Example 17 |
| 19 | 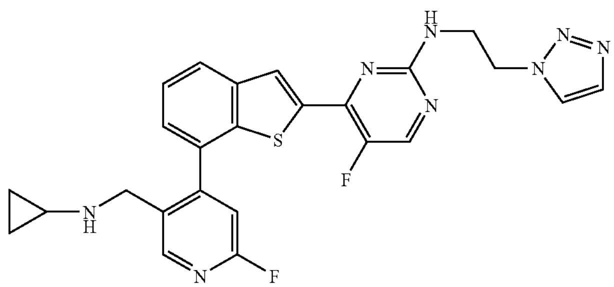 | N-(2-(1H-1,2,3-Triazol-1-yl)ethyl)-4-(7-(5-((cyclopropylamino)methyl)-2-fluoropyridin-4-yl)benzo[b]thiophen-2-yl)-5-fluoropyrimidin-2-amine | 505 | Conditions similar to Example 17 |
| 20 | 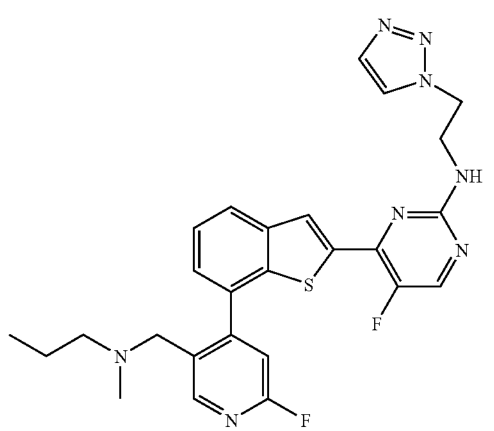 | N-(2-(1H-1,2,3-Triazol-1-yl)ethyl)-5-fluoro-4-(7-(2-fluoro-5-((methyl(propyl)amino)methyl)pyridin-4-yl)benzo[b]thiophen-2-yl)pyrimidin-2-amine | 521 | |
| 21 | 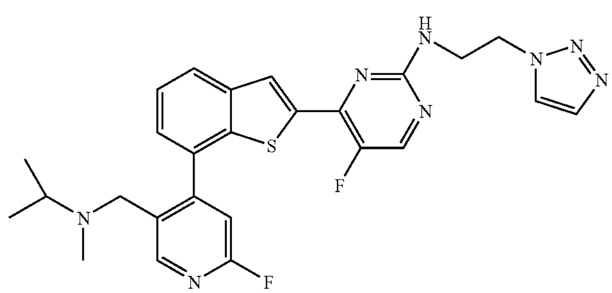 | N-(2-(1H-1,2,3-Triazol-1-yl)ethyl)-5-fluoro-4-(7-(2-fluoro-5-((isopropyl(methyl)amino)methyl)pyridin-4-yl)benzo[b]thiophen-2-yl)pyrimidin-2-amine | 521 | |

| Ex | Compound structure | Compound Name | MS (ES) m/z [M + 1]+ | Comments |
|---|---|---|---|---|
| 22 | 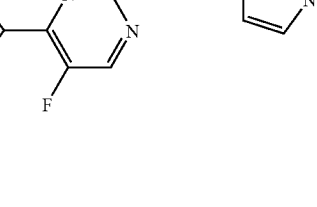 | N-(2-(1H-1,2,3-Triazol-1-yl)ethyl)-5-fluoro-4-(7-(2-fluoro-5-((propylamino)-methyl)-pyridin-4-yl)benzo[b]thiophen-2-yl)pyrimidin-2-amine | 507 | |
| 23 | 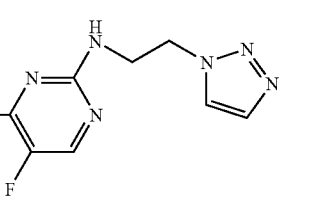 | N-(2-(1H-1,2,3-Triazol-1-yl)ethyl)-5-fluoro-4-(7-(2-fluoro-5-((isopropylamino)-methyl)pyridin-4-yl)benzo[b]thiophen-2-yl)pyrimidin-2-amine | 507 | |
| 24 | 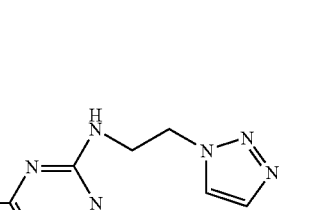 | N-(2-(1H-1,2,3-triazol-1-yl)ethyl)-4-(7-(5-((ethylamino)methyl)-2-fluoropyridin-4-yl)benzo[b]thiophen-2-yl)-5-fluoropyrimidin-2-amine | 491 | |
| 25 | 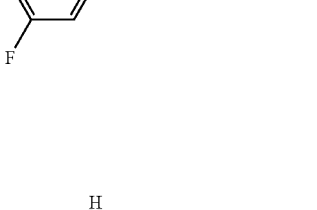 | N-(2-(1H-1,2,3-Triazol-1-yl)ethyl)-4-(7-(5-((ethyl(methyl)amino)methyl)-2-fluoropyridin-4-yl)benzo[b]thiophen-2-yl)-5-fluoropyrimidin-2-amine | 507 | |
| 26 | 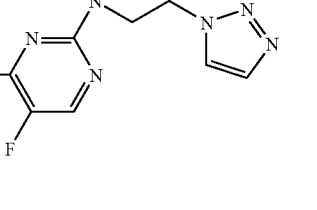 | N-(2-(1H-1,2,3-Triazol-1-yl)ethyl)-4-(7-(5-((4,4-dimethyloxazolidin-3-yl)methyl)-2-fluoropyridin-4-yl)benzo[b]thiophen-2-yl)-5-fluoropyrimidin-2-amine | 549 | |

-continued

| Ex | Compound structure | Compound Name | MS (ES) m/z [M + 1]+ | Comments |
|---|---|---|---|---|
| 27 | 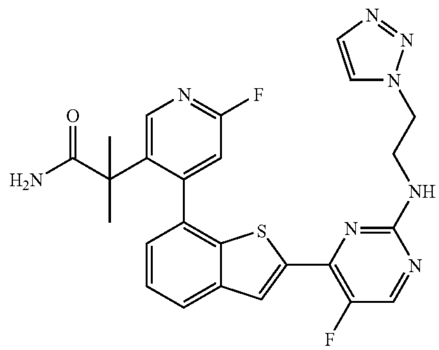 | 2-(4-(2-(2-(2-(1H-1,2,3-Triazol-1-yl)ethylamino)-5-fluoropyrimidin-4-yl)benzo[b]thiophen-7-yl)-6-fluoropyridin-3-yl)-2-methylpropanamide | 521 | |
| 28 | 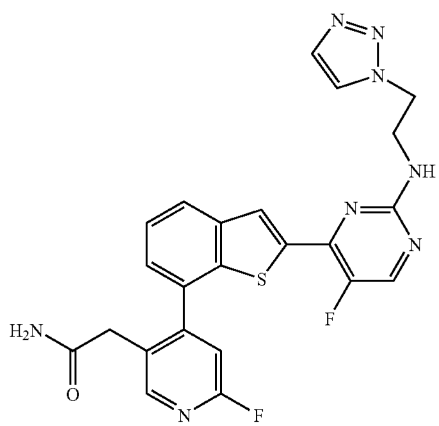 | 2-(4-(2-(2-(2-(1H-1,2,3-Triazol-1-yl)ethylamino)-5-fluoropyrimidin-4-yl)benzo[b]thiophen-7-yl)-6-fluoropyridin-3-yl)acetamide | 493 | |
| 29 | 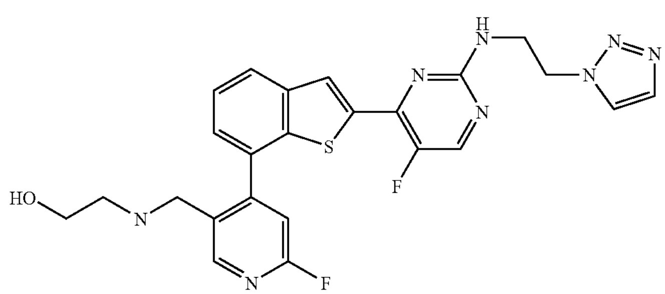 | 2-((4-(2-(2-(2-(1H-1,2,3-Triazol-1-yl)ethylamino)-5-fluoropyrimidin-4-yl)benzo[b]thiophen-7-yl)-6-fluoropyridin-3-yl)methylamino)ethanol | 509 | Conditions similar to Example 17 |
| 30 | 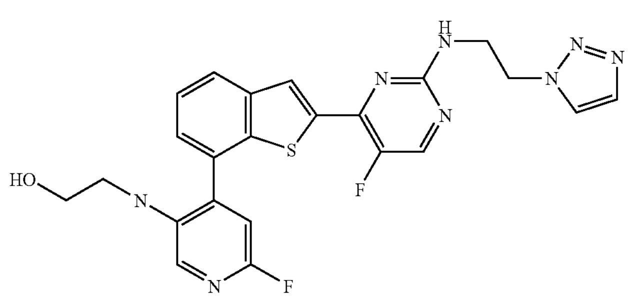 | 2-(4-(2-(2-(2-(1H-1,2,3-Triazol-1-yl)ethylamino)-5-fluoropyrimidin-4-yl)benzo[b]thiophen-7-yl)-6-fluoropyridin-3-ylamino)ethanol | 495 | |

| Ex | Compound structure | Compound Name | MS (ES) m/z [M + 1]+ | Comments |
|---|---|---|---|---|
| 31 | 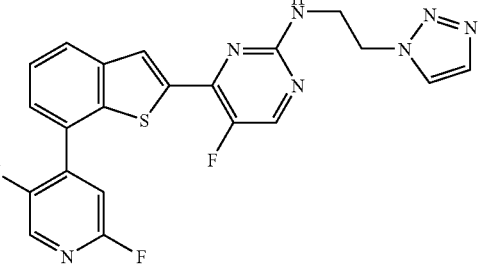 | N-(2-(1H-1,2,3-Triazol-1-yl)ethyl)-5-fluoro-4-(7-(2-fluoro-5-(2-methoxyethyl-amino) pyridin-4-yl)benzo[b]thiophen-2-yl)pyrimidin-2-amine | 509 | |
| 32 | 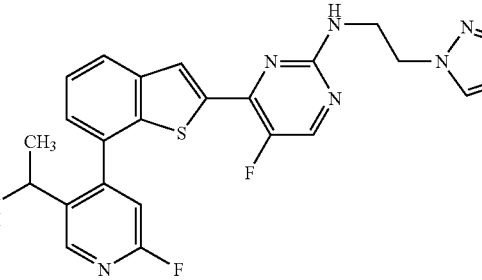 | N-(2-(1H-1,2,3-Triazol-1-yl)ethyl)-5-fluoro-4-(7-(2-fluoro-5-(1-(2-fluoroethyl-amino)ethyl)pyridin-4-yl)benzo[b]thiophen-2-yl)pyrimidin-2-amine | 525 | |
| 33 | 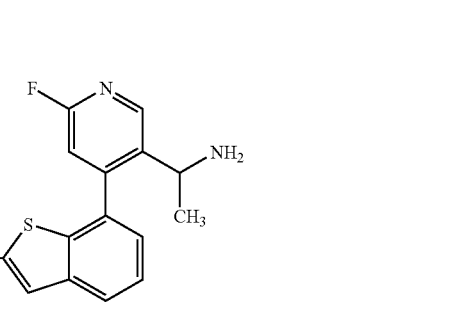 | N-(2-(1H-1,2,3-Triazol-1-yl)ethyl)-4-(7-(5-(1-aminoethyl)-2-fluoropyridin-4-yl)benzo[b]thiophen-2-yl)-5-methylpyrimidin-2-amine | 475 | |
| 34 | 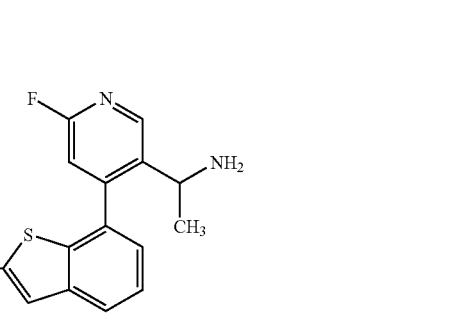 | N-(2-(1H-1,2,3-Triazol-1-yl)ethyl)-4-(7-(5-(1-aminoethyl)-2-fluoropyridin-4-yl)benzo[b]thiophen-2-yl)-5-chloropyrimidin-2-amine | 495 | |
| 35 | 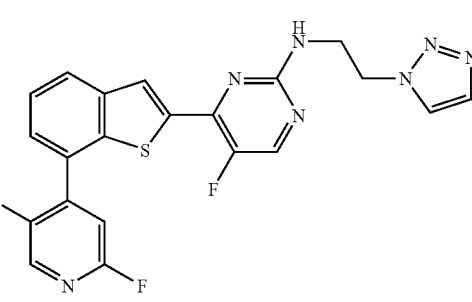 | 2-((4-(2-(2-(1H-1,2,3-Triazol-1-yl)ethylamino)-5-fluoropyrimidin-4-yl)benzo[b]thiophen-7-yl)-6-fluoropyridin-3-yl)oxy)-propan-2-ol | 510 | |

EXAMPLE 36

N-(2-(1H-1,2,3-Triazol-1-yl)ethyl)-4-(7-(2-chloro-5-(1-(methylamino)ethyl)pyridin-4-yl)benzo[b]thiophen-2-yl)pyrimidin-2-amine

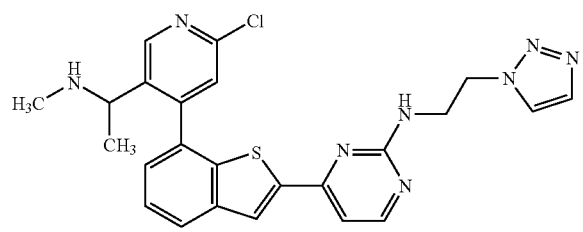

Combine tert-butyl 1-(4-(2-(2-(2-(1H-1,2,3-triazol-1-yl)ethylamino)pyrimidin-4-yl)benzo[b]thiophen-7-yl)-6-chloropyridin-3-yl)ethyl(methyl)carbamate (300 mg, 0.5 mmol) and dry TFA (2.0 mL) in dry DCM (6 mL). Stir the solution at RT for 1 h. Dilute the resulting residue with DCM and wash with saturated sodium bicarbonate solution, water, and saturated aqueous sodium chloride. Separate the organic layer and dry over magnesium sulfate. Filter and concentrate in vacuo to give a residue. Purify the residue by column chromatography [0.1% to 2% 2 M ammonia in methanol/DCM] to afford the title compound (175 mg, 70%). MS (ES) m/z 491 [M+1]$^+$.

Prepare the following examples with procedures similar to those described for N-(2-(1H-1,2,3-Triazol-1-yl)ethyl)-4-(7-(2-chloro-5-(1-(methylamino)ethyl)pyridin-4-yl)benzo[b]thiophen-2-yl)pyrimidin-2-amine:

| Ex | Structure | Compound Name | MS (ES) m/z [M + 1]$^+$ |
|---|---|---|---|
| 37 |  | N-(2-(1H-1,2,3-Triazol-1-yl)ethyl)-4-(7-(5-(1-aminoethyl)-2-chloropyridin-4-yl)benzo[b]thiophen-2-yl)-5-methylpyrimidin-2-amine | 492 |
| 38 |  | N-(2-(1H-1,2,3-Triazol-1-yl)ethyl)-4-(7-(2-chloro-5-(1-(piperazin-1-yl)ethyl)pyridin-4-yl)benzo[b]thiophen-2-yl)-5-fluoropyrimidin-2-amine | 564 |
| 39 |  | N-(2-(1H-1,2,3-Triazol-1-yl)ethyl)-4-(7-(5-(1-aminoethyl)-2-methylpyridin-4-yl)benzo[b]thiophen-2-yl)-5-fluoropyrimidin-2-amine | 475 |

EXAMPLE 40

1-(4-(2-(2-(2-(1H-1,2,3-Triazol-1-yl)ethylamino)-5-fluoropyrimidin-4-yl)benzo[b]thiophen-7-yl)-6-fluoropyridin-3-yl)ethanol

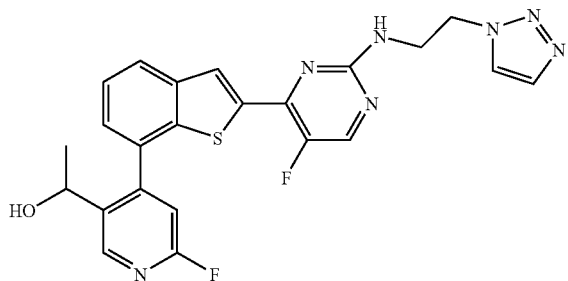

Add 5 mL of 1 N HCl to a solution of 5-fluoro-4-{7-[2-fluoro-5-(1-methoxymethoxy-ethyl)-pyridin-4-yl]-benzo[b]thiophen-2-yl}-pyrimidin-2-yl)-(2-[1,2,3]triazol-1-yl-ethyl (350 mg, 0.67 mmol) in methanol (10 mL). Stir the mixture overnight. Dilute the reaction mixture with sodium carbonate (2 N). Extract the product into chloroform. Dry the organic phase over sodium sulfate. Concentrate the solution in vacuo to a give the crude. Purify the crude by column chromatography (10% methanol in DCM) to afford the title compound as a yellow solid (150 mg, 47%). MS (ES) m/z 480 [M+1]$^+$, 502 [M+Na]$^+$.

EXAMPLE 41

N-(2-(1H-1,2,3-Triazol-1-yl)ethyl)-4-(7-(5-(1-aminoethyl)-2-fluoropyridin-4-yl)benzo[b]thiophen-2-yl)-5-fluoropyrimidin-2-amine

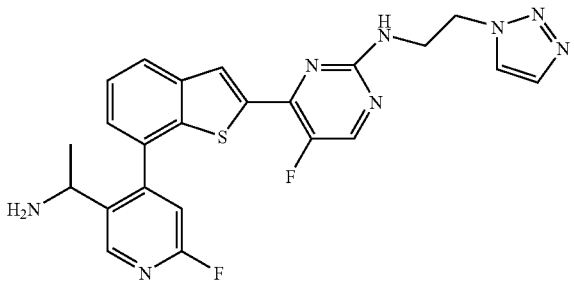

Combine tellurium (1.27 g, 10 mmol) and sodium tetrahydroborate (0.9 g, 2.4 mmol) in ethanol (20 mL) under nitrogen. Heat the mixture to refluxing until it becomes a clear red solution. Add 5 mL of the solution to a solution of (4-{7-[5-(1-azido-ethyl)-2-fluoro-pyridin-4-yl]-benzo[b]thiophen-2-yl}-5-fluoro-pyrimidin-2-yl)-(2-[1,2,3]-triazol-1-yl-ethyl)-amine (400 mg, 0.8 mmol) in ethanol (10 mL). Stir the mixture for 20 min at RT. Filter off the black solid. Wash the solid with methanol and DCM. Evaporate the combined mother liquor to give the crude product. Purify the crude product by FCC (chloroform/methanol/ammonium hydroxide, 7/3/0.05) to give the title compound as a yellow solid (200 mg, 52%). MS (ES) m/z 479 [M+1]$^+$.

EXAMPLE 42

2-(4-(2-(2-(2-(1H-1,2,3-Triazol-1-yl)ethylamino)-5-fluoropyrimidin-4-yl)benzo[b]thiophen-7-yl)-6-fluoropyridin-3-yloxy)ethanol

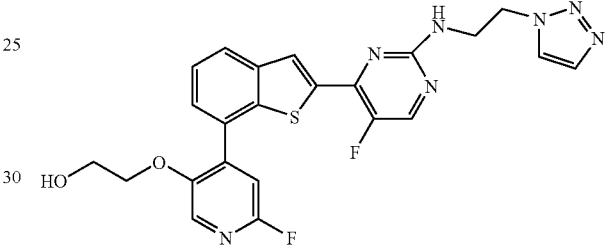

Add pyridinium p-toluenesulfonate (8.23 mg, 0.03 mmol) to a solution of [5-fluoro-4-(7-{2-fluoro-5-[2-(tetrahydro-pyran-2-yloxy)-ethoxy]-pyridin-4-yl}-benzo[b]thiophen-2-yl)-pyrimidin-2-yl]-(2-[1,2,3]triazol-1-yl-ethyl)-amine (190 mg, 0.32 mmol) in ethanol (4 mL). Stir the mixture at 55° C. overnight. Cool the solution. Concentrate the solution in vacuo to a yellow oil. Purify by column chromatography (methylene chloride to 10% methanol in methylene chloride) to afford the title compound (0.14 g, 88%) as a light yellow solid. MS (ES) m/z 496 [M+1]$^+$.

Prepare the following example from (5-Fluoro-4-{7-[2-fluoro-5-(1-methoxymethoxy-ethyl)-pyridin-4-yl]-benzo[b]thiophen-2-yl}-pyrimidin-2-yl)-(2-[1,2,3]triazol-1-yl-ethyl)-amine with procedures similar to the one described for the example above:

| Ex | Compound structure | Compound Name | MS (ES) m/z [M + 1]$^+$ |
|---|---|---|---|
| 43 | 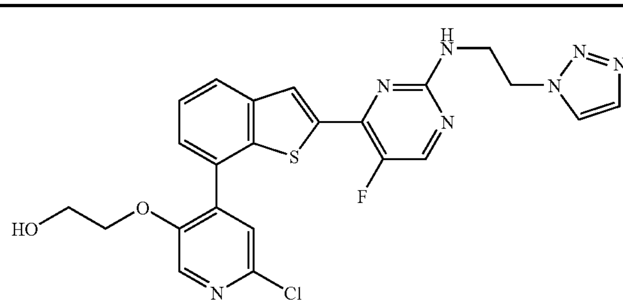 | 2-(4-(2-(2-(2-(1H-1,2,3-Triazol-1-yl)ethylamino)-5-fluoropyrimidin-4-yl)benzo[b]thiophen-7-yl)-6-chloropyridin-3-yloxy)ethanol | 512 |

EXAMPLE 44

N-(2-(1H-1,2,3-Triazol-1-yl)ethyl)-4-(7-(3-(aminomethyl)pyridin-4-yl)benzo[b]thiophen-2-yl)-5-fluoropyrimidin-2-amine

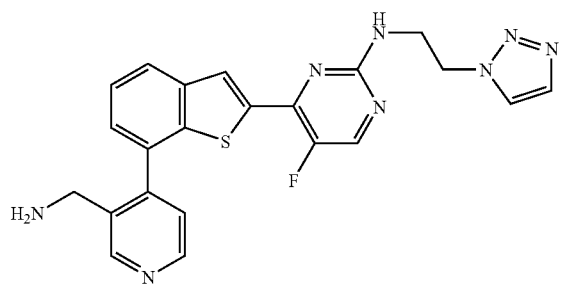

Combine 3-(Boc-aminomethyl)-pyridine-4-boronic acid (100 mg, 0.4 mmol), [4-(7-bromo-benzo[b]thiophen-2-yl)-5-fluoro-pyrimidin-2-yl]-(2-[1,2,3]triazol-1-yl-ethyl)-amine (100 mg, 0.24 mmol), Pd(dppf)Cl$_2$ (9 mg, 0.01 mmol), 2-di-tert-butylphosphino)biphenyl (3 mg, 0.01 mmol), and sodium carbonate (2 M, 0.3 mL, 0.6 mmol) in 10 ml, dioxane. Heat the mixture at 100° C. for 31 h in an oil bath. Dilute the mixture with chloroform/IPA (3/1). Wash the solution with saturated aqueous sodium chloride. Dry over sodium sulfate. Concentrate the solution in vacuo to a dark residue. Purify by column chromatography (20% ethyl acetate in hexane) to afford the Boc protected product as a yellow solid. Dissolve in TFA (30% in DCM) and stir it for 30 min. Evaporate off the TFA. Dissolve the TFA salt in 5 mL of ammonia in methanol (7 N). Purify the final product by FCC (DCM→chloroform/methanol/30% ammonium hydroxide, 7/3/0.05) to afford the title compound as a yellow solid (40 mg, 39%). MS (ES) m/z 467 [M+1]$^+$.

Prepare the following example with procedures similar to the ones for the example above:

| Ex | Compound structure | Compound Name | MS (ES) m/z [M + 1]$^+$ |
|---|---|---|---|
| 45 | 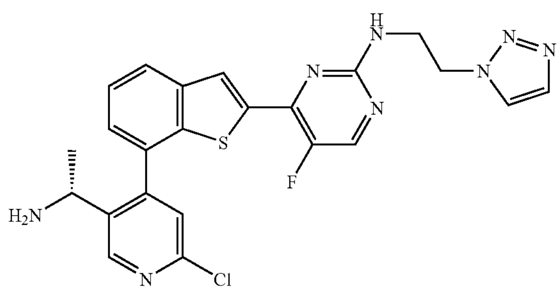 | (R)-N-(2-(1H-1,2,3-Triazol-1-yl)ethyl)-4-(7-(5-(1-aminoethyl)-2-chloropyridin-4-yl)benzo[b]thiophen-2-yl)-5-fluoropyrimidin-2-amine | 495 |
| 46 | 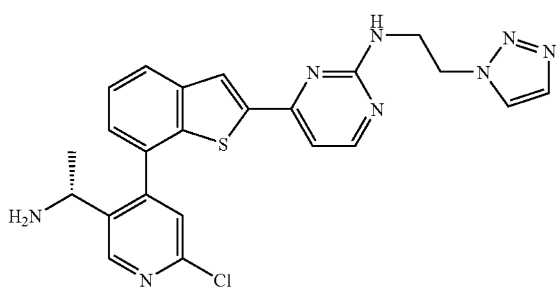 | (R)-N-(2-(1H-1,2,3-Triazol-1-yl)ethyl)-4-(7-(5-(1-aminoethyl)-2-chloropyridin-4-yl)benzo[b]thiophen-2-yl)pyrimidin-2-amine | 477 |
| 47 | 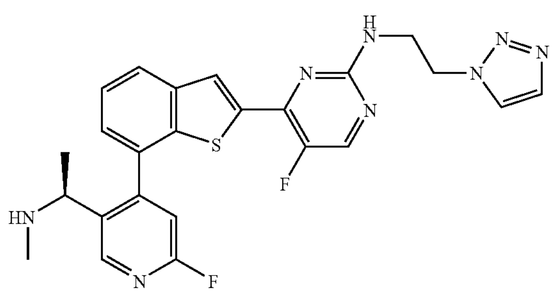 | (S)-N-(2-(1H-1,2,3-Triazol-1-yl)ethyl)-5-fluoro-4-(7-(2-fluoro-5-(1-(methylamino)ethyl)pyridin-4-yl)benzo[b]thiophen-2-yl)pyrimidin-2-amine | 493 |

| Ex | Compound structure | Compound Name | MS (ES) m/z [M + 1]+ |
|---|---|---|---|
| 48 | 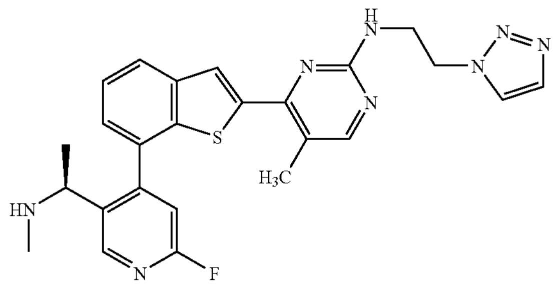 | (S)-N-(2-(1H-1,2,3-Triazol-1-yl)ethyl)-4-(7-(2-fluoro-5-(1-(methylamino)ethyl)-pyridin-4-yl)benzo[b]thiophen-2-yl)-5-methyl-pyrimidin-2-amine | 489 |
| 49 | 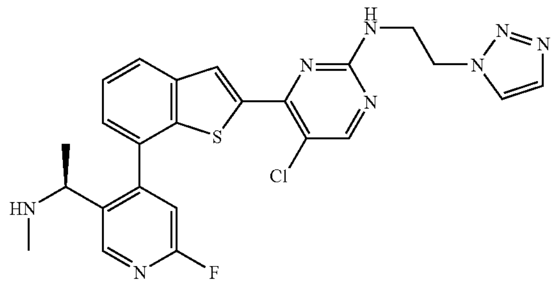 | (S)-N-(2-(1H-1,2,3-Triazol-1-yl)ethyl)-5-(chloro-4-(7-(2-fluoro-5-(1-(methylamino)ethyl)pyridin-4-yl)benzo[b]thiophen-2-yl)pyrimidin-2-amine | 509 |
| 50 | 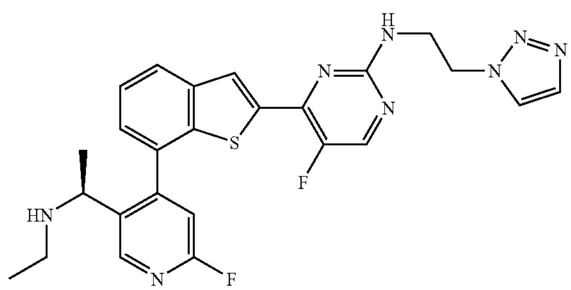 | N-(2-(1H-1,2,3-Triazol-1-yl)ethyl)-4-(7-(5-(1-(ethylamino)ethyl)-2-fluoropyridin-4-yl)benzo[b]thiophen-2-yl)-5-fluoropyrimidin-2-amine | 507 |

EXAMPLE 51

(S)—N-(2-(1H-1,2,3-Triazol-1-yl)ethyl)-4-(7-(2-fluoro-5-(1-(methylamino)ethyl)pyridin-4-yl)benzo[b]thiophen-2-yl)pyrimidin-2-amine

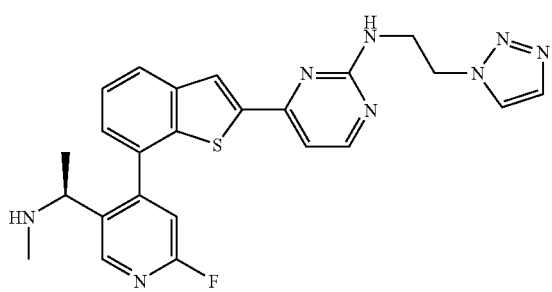

Combine {5-fluoro-4-[7-(4,4,5,5-tetramethyl-[1,3,2]dioxaborolan-2-yl)-benzo[b]thiophen-2-yl]-pyrimidin-2-yl}-(2-[1,2,3]triazol-1-yl-ethyl)-amine (0.32 g, 0.71 mmol) and (S)-tert-butyl 1-(6-fluoro-4-iodopyridin-3-yl)ethyl(methyl)carbamate (0.25 g, 0.65 mmol) in acetonitrile (3 mL) and water (1.5 mL). Purge with nitrogen bubbling for 10 min and add Pd(dppf)Cl₂ (0.039 g, 0.047 mmol). Heat the mixture in a microwave reactor for 10 min at 120° C., cool to RT and remove solvent under a nitrogen stream. Chromatograph the residue on silica gel with a gradient 1% THF/ethylacetate to 10% THF/ethylacetate; then with another gradient 1% (10% methanol containing 0.5 M ammonia in DCM)/DCM to 20% (10% methanol containing 0.5M ammonia in DCM)/DCM to give the Boc protected intermediate (0.14 g, 37%). Treat the Boc protected intermediate in DCM (2 mL) with TFA (2 mL) at RT for 2 h. Evaporate the TFA under vacuum and partition the residue between DCM and saturated sodium bicarbonate aqueous. Wash the organic phase with water, saturated brine, dry over magnesium sulfate, filter and evaporate the solvent under vacuum. Purify with reverse phase chromatography to give the title compound (0.1 g) MS (ES) m/z 475 [M+1]+.

EXAMPLE 52

1-((4-(2-(2-(2-(1H-1,2,3-Triazol-1-yl)ethylamino)-5-fluoropyrimidin-4-yl)benzo[b]thiophen-7-yl)-6-fluoropyridin-3-yl)methyl)piperidin-4-ol

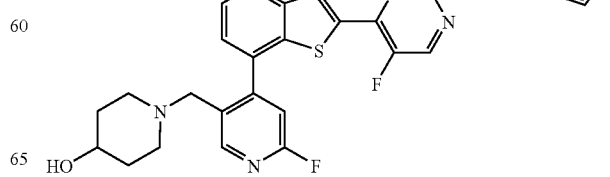

Combine 5-(bromomethyl)-2-fluoro-4-iodopyridine (0.2 g, 0.63 mmol), piperidin-4-ol (0.192 mg, 1.9 mmol), and diisopropylethylamine (0.22 mL, 1.27 mmol) in acetonitrile (3.0 mL). Heat the reaction mixture at 80° C. for 2 h and cool to RT. Remove the organic solvent to give crude 1-((6-fluoro-4-iodopyridin-3-yl)methyl)piperidin-4-ol. Combine crude 1-((6-fluoro-4-iodopyridin-3-yl)methyl)piperidin-4-ol (0.63 mmol), N-(2-(1H-1,2,3-triazol-1-yl)ethyl)-5-fluoro-4-(7-(4,4,5,5-tetramethyl-1,3,2-dioxaborolan-2-yl)benzo[b]thiophen-2-yl)pyrimidin-2-amine (0.15 g, 0.32 mmol, sodium carbonate (0.102 g, 0.96 mmol), 2-(di-tert-butylphospho)biphenyl (0.006 g, 0.06 mmol) and Pd(dppf)Cl$_2$ (0.026 g, 0.1 mmol) in THF (3 mL) and water (1 mL). Heat the mixture at 120° C. for 10 min in a microwave reactor. Pour the crude reaction mixture onto a strong cation exchange (SCX) (10 g) column. Elute the desired product with 2 N methanolic ammonia (40 mL) and concentrate. Purify by reverse phase chromatography (28% isocratic at 85 mL/min for 8 min on a 30×75 mm, 5 mm, C$_{18}$ ODB MS XBridge™ column, Solvent A: water with 0.01 M ammonium bicarbonate, Solvent B: acetonitrile) to afford the title compound (91 mg, 52%). MS (ES) m/z 549 [M+1]$^+$.

Prepare the following examples with procedures similar to the ones for 1-((4-(2-(2-(2-(1H-1,2,3-Triazol-1-yl)ethylamino)-5-fluoropyrimidin-4-yl)benzo[b]thiophen-7-yl)-6-fluoropyridin-3-yl)methyl)piperidin-4-ol:

| Ex | Structure | Compound Name | Physical Data MS (ES) m/z [M + 1]$^+$ |
|---|---|---|---|
| 53 | 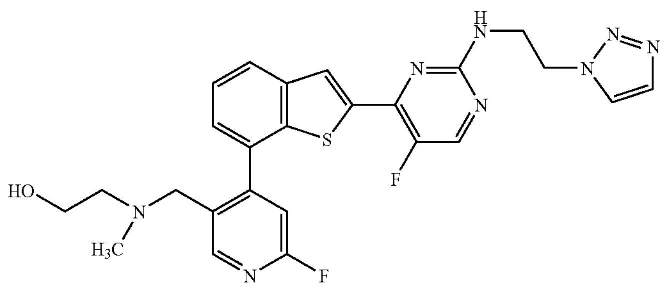 | 2-(((4-(2-(2-(2-(1H-1,2,3-Triazol-1-yl)ethylamino)-5-fluoropyrimidin-4-yl)benzo[b]thiophen-7-yl)-6 fluoropyridin-3-yl)methyl)(methyl)amino)-ethanol | 523 |
| 54 | 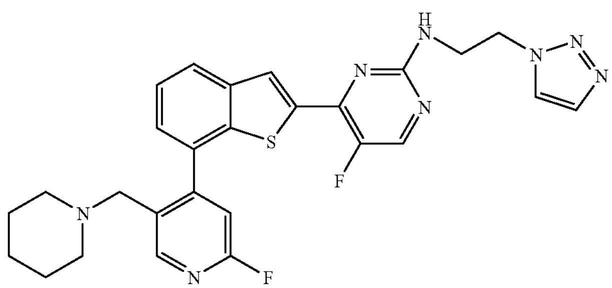 | N-(2-(1H-1,2,3-Triazol-1-yl)ethyl)-5-fluoro-4-(7-(2-fluoro-5-(piperidin-1-ylmethyl)pyridin-4-yl)benzo[b]thiophen-2-yl)pyrimidin-2-amine | 533 |
| 55 | 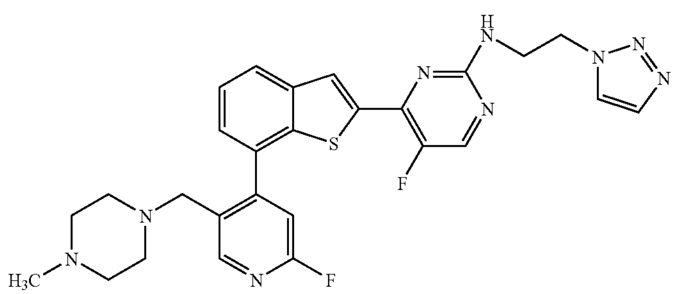 | N-(2-(1H-1,2,3-Triazol-1-yl)ethyl)-5-fluoro-4-(7-(2-fluoro-5-((4-methylpiperazin-1-yl)methyl)pyridin-4-yl)benzo[b]thiophen-2-yl)pyrimidin-2-amine | 548 |
| 56 | 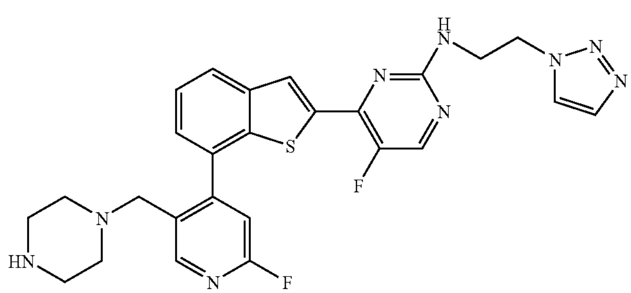 | N-(2-(1H-1,2,3-Triazol-1-yl)ethyl)-5-fluoro-4-(7-(2-fluoro-5-(piperazin-1-yl-methyl)pyridin-4-yl)benzo[b]thiophen-2-yl)pyrimidin-2-amine | 534 |

US 8,114,872 B2

-continued

| Ex | Structure | Compound Name | Physical Data MS (ES) m/z [M + 1]+ |
|---|---|---|---|
| 57 | 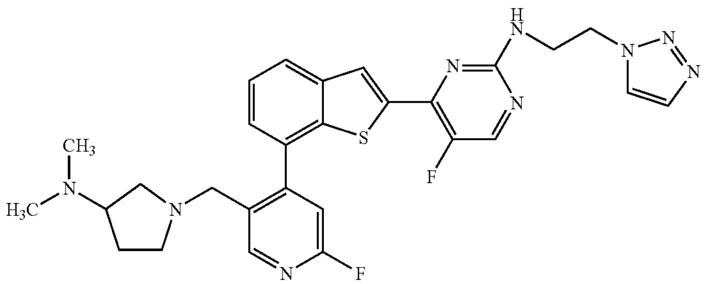 | N-(2-(1H-1,2,3-Triazol-1-yl)ethyl)-4-(7-(5-((3-(dimethylamino)pyrrolidin-1-yl)methyl)-2-fluoropyridin-4-yl)benzo[b]thiophen-2-yl)-5 fluoropyrimidin-2-amine | 562 |
| 58 | 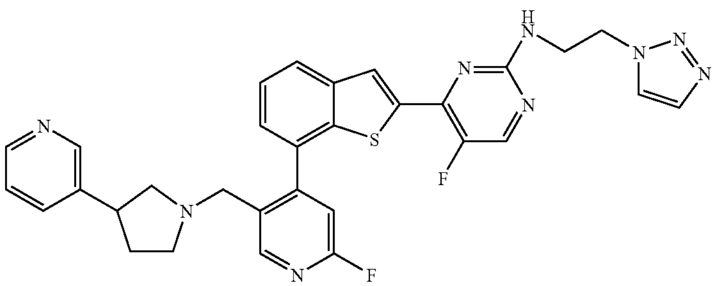 | N-(2-(1H-1,2,3-Triazol-1-yl)ethyl)-5-fluoro-4-(7-(2-fluoro-5-((3-(pyridin-3-yl)pyrrolidin-1-yl)methyl)pyridin-4-yl)benzo[b]thiophen-2-yl)pyrimidin-2-amine | 596 |
| 59 | 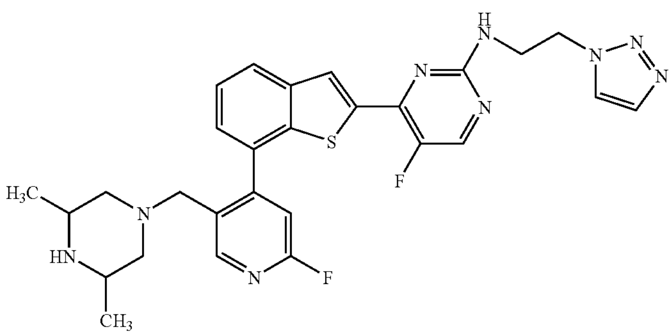 | N-(2-(1H-1,2,3-Triazol-1-yl)ethyl)-4-(7-(5-((3,5-dimethylpiperazin-1-yl)methyl)-2-fluoropyridin-4-yl)benzo[b]thiophen-2-yl) 5-fluoropyrimidin-2-amine | 562 |
| 60 | 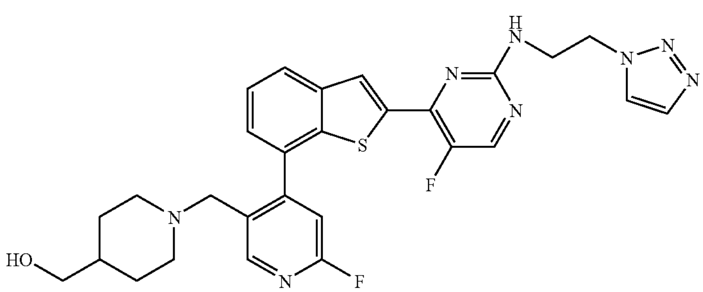 | (1-((4-(2-(2-(1H-1,2,3-Triazol-1-yl)ethylamino)-5-fluoropyrimidin-4-yl)benzo[b]thiophen-7-yl)-6 fluoropyridin-3-yl)methyl)piperidin-4-yl)methanol | 563 |
| 61 | 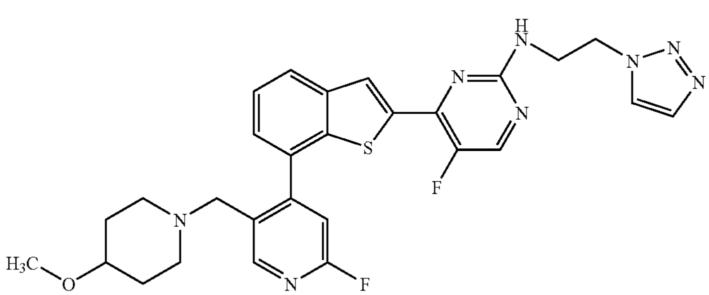 | N-(2-(1H-1,2,3-Triazol-1-yl)ethyl-5-fluoro-4-(7-(2-fluoro-5-((4-methoxypiperidin-1-yl)methyl)pyridin-4-yl)benzo[b]thiophen-2-yl)pyrimidin-2-amine | 563 |

| Ex | Structure | Compound Name | Physical Data MS (ES) m/z [M + 1]+ |
|---|---|---|---|
| 62 | 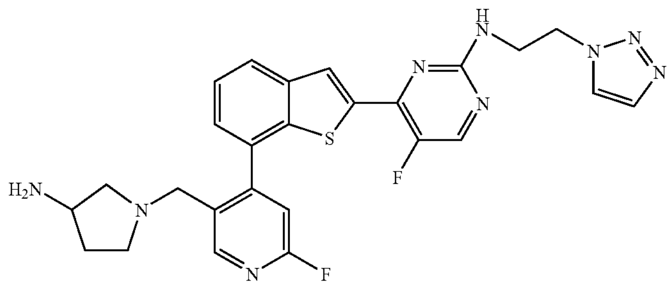 | N-(2-(1H-1,2,3-Triazol-1-yl)ethyl)-4-(7-(5-((3-aminopyrrolidin-1-yl)methyl)-2-fluoropyridin-4-yl)benzo[b]thiophen-2-yl)-5-fluoropyrimidin-2-amine | 534 |

EXAMPLE 63

N-(2-(1H-1,2,3-Triazol-1-yl)ethyl)-5-fluoro-4-(7-(2-fluoro-5-((3-(methylamino)pyrrolidin-1-yl)methyl)pyridin-4-yl)benzo[b]thiophen-2-yl)pyrimidin-2-amine

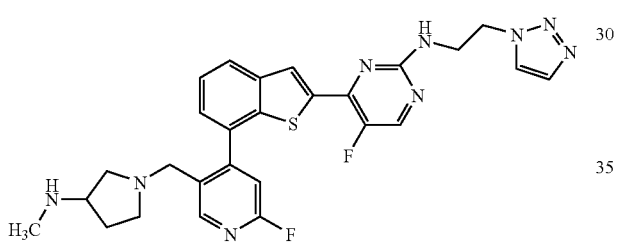

Combine 5-(bromomethyl)-2-fluoro-4-iodopyridine (0.2 g, 0.63 mmol), 3-(N-tert-butoxycarbonyl-N-methylamine)pyrrolidine (0.381 mg, 1.9 mmol), and diisopropyl-ethylamine (0.22 mL, 1.27 mmol) in acetonitrile (3.0 mL). Heat the reaction mixture at 80° C. for 2 h and cool to RT. Remove the organic solvent to give crude tert-butyl 1-((6-fluoro-4-iodopyridin-3-yl)methyl)pyrrolidin-3-yl(methyl)carbamate. Combine crude tert-butyl 1-((6-fluoro-4-iodopyridin-3-yl)methyl)pyrrolidin-3-yl(methyl)carbamate (0.63 mmol), N-(2-(1H-1,2,3-triazol-1-yl)ethyl)-5-fluoro-4-(7-(4,4,5,5-tetramethyl-1,3,2-dioxaborolan-2-yl)benzo[b]thiophen-2-yl)pyrimidin-2-amine (0.15 g, 0.32 mmol), sodium carbonate (0.102 g, 0.96 mmol), 2-(di-tert-butylphospho)biphenyl (0.006 g, 0.06 mmol) and Pd(dppf)Cl$_2$ (0.026 g, 0.1 mmol) in THF (3 mL) and water (1 mL). Heat the mixture at 120° C. for 10 min in a microwave reactor. Pour the crude reaction mixture onto a strong cation exchange (SCX) (10 g) column. Elute the desired product with 2 N methanolic ammonia (40 mL) and concentrate. Purify by reverse phase chromatography (56% isocratic at 85 mL/min for 8 min on a 30×75 mm, 5 mm, C$_{18}$ ODB MS XBridge™ column, Solvent A: water with 0.01 M ammonium bicarbonate, Solvent B: acetonitrile) to afford the Boc protected product.

Dilute tert-butyl 1-((4-(2-(2-(2-(1H-1,2,3-triazol-1-yl)ethylamino)-5-fluoropyrimidin-4-yl)benzo[b]thiophen-7-yl)-6-fluoropyridin-3-yl)methyl)pyrrolidin-3-yl(methyl)carbamate (118 mg, 0.18 mmol) in DCM (3 mL) and treat with 4 M hydrochloric acid in dioxane (0.45 mL, 1.8 mmol). Heat the mixture at 35° C. for 2 h. Remove the organic solvent to give the crude deprotected product. Dilute in DCM (3 mL) and methanol. Pour the mixture onto a strong cation exchange (SCX) (10 g) column. Elute the desired product with 2 N methanolic ammonia (40 mL) and concentrate. Dry the concentrated material from 1:1 acetonitrile/water by lyophilizing to afford the title compound (88 mg, 46%). MS (ES) m/z 548 [M+1]+.

EXAMPLE 64

N-(2-(1H-1,2,3-Triazol-1-yl)ethyl)-4-(7-(5-(1-(cyclopropylamino)ethyl)-2-fluoropyridin-4-yl)benzo[b]thiophen-2-yl)-5-fluoropyrimidin-2-amine

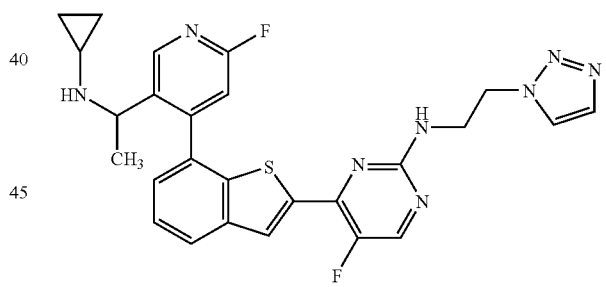

Slowly add methanesulfonyl chloride (0.04 mL, 0.55 mmol) to a solution of newly synthesized 1-(4-(2-(2-(2-(1H-1,2,3-triazol-1-yl)ethylamino)-5-fluoropyrimidin-4-yl)benzo[b]thiophen-7-yl)-6-fluoropyridin-3-yl)ethanol (240 mg, 0.50 mmol) and triethylamine (0.14 mL, 1.0 mmol) in methylene chloride (5 mL) at −78° C. After stirring the mixture at the same temperature for another 60 min, add cyclopropylamine (0.040 mL, 0.55 mmol) and leave it overnight at RT. Heat it to 45° C. for 5 h, cool to RT, and remove the solvent. Purify by column chromatography (10% methanol in DCM) to afford the title compound (42 mg 17%). MS (ES) m/z 519 [M+1]+.

Prepare the following examples with procedures similar to those for N-(2-(1H-1,2,3-Triazol-1-yl)ethyl)-4-(7-(5-(1-(cyclopropylamino)ethyl)-2-fluoropyridin-4-yl)benzo[b]thiophen-2-yl)-5-fluoropyrimidin-2-amine but using the appropriate starting materials:

| Ex | Structure | Compound Name | MS (ES) m/z [M + 1]+ |
|---|---|---|---|
| 65 | 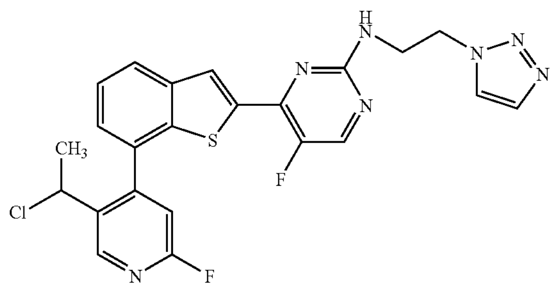 | N-(2-(1H-1,2,3-Triazol-1-yl)ethyl)-4-(7-(5-(1-chloroethyl)-2-fluoropyridin-4-yl)benzo[b]thiophen-2-yl)-5-fluoropyrimidin-2-amine | 494 |
| 66 | 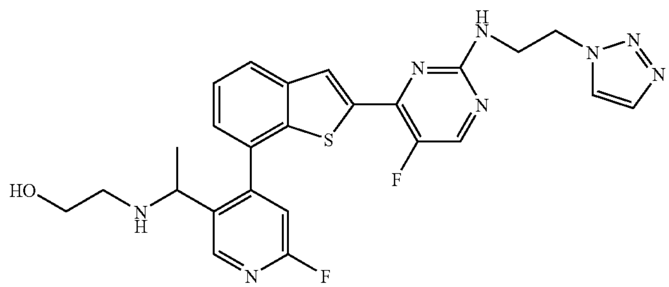 | (R)-2-(1-(4-(2-(2-(1H-1,2,3-Triazol-1-yl)ethylamino)-5-fluoropyrimidin-4-yl)benzo[b]thiophen-7-yl)-6-fluoropyridin-3-yl)ethylamino)ethanol | 523 |

Prepare the following examples with procedures similar to those described for N-(2-(1H-1,2,3-Triazol-1-yl)ethyl)-4-(7-(2-chloro-5-(1-(methylamino)ethyl)pyridin-4-yl)benzo[b]thiophen-2-yl)pyrimidin-2-amine above:

| Ex | Compound structure | Compound Name | MS (ES) [M + 1]+ |
|---|---|---|---|
| 67 | 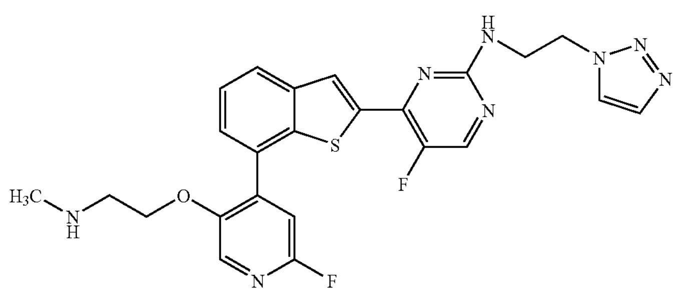 | N-(2-(1H-1,2,3-Triazol-1-yl)ethyl)-5-fluoro-4-(7-(2-fluoro-5-(2-(methylamino)ethoxy)pyridin-4-yl)benzo[b]thiophen-2-yl)pyrimidin-2-amine | 509 |
| 68 | 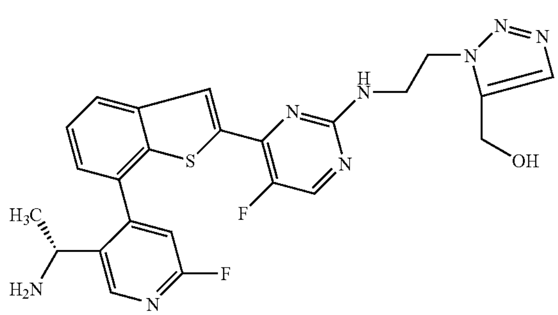 | (R)-(1-(2-(4-(7-(5-(1-Aminoethyl)-2-fluoropyridin-4-yl)benzo[b]thiophen-2-yl)-5-fluoropyrimidin-2-ylamino)ethyl)-1H-1,2,3-triazol-5-yl)methanol | 509 |

| Ex | Compound structure | Compound Name | MS (ES) [M + 1]+ |
|---|---|---|---|
| 69 | 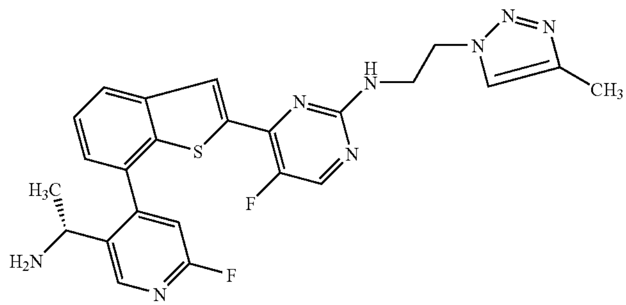 | (R)-4-(7-(5-(1-Aminoethyl)-2-fluoropyridin-4-yl)benzo[b]thiophen-2-yl)-5-fluoro-N-(2-(4-methyl-1H-1,2,3-triazol-1-yl)ethyl)pyrimidiin-2-amine | 493 |

EXAMPLE 70

(R)-1-(4-(2-(2-(2-(1H-1,2,3-Triazol-1-yl)ethy-lamino)-5-fluoropyrimidin-4-yl)benzo[b]thiophen-7-yl)-6-fluoropyridin-3-yl)ethanol

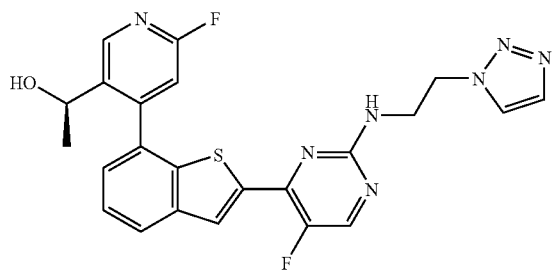

Separate 180 mg of racemic 1-(4-(2-(2-(2-(1H-1,2,3-triazol-1-yl)ethylamino)-5-fluoropyrimidin-4-yl)benzo[b]thiophen-7-yl)-6-fluoropyridin-3-yl)ethanol by chiral chromatography to give the title compound 44 mg (24%). MS (ES) m/z 480 [M+1]+. Chiral OJ-H Column: 20% methanol, 0.2% isopropyl amine in $CO_2$, flow rate: 5 mL/min, detection at 225 nm; or Column Chiralpak® AS-H: 100% MeOH/ 0.02% DMEA (dimethyl-ethyl amine)\$CO_2$, 5 mL/min, 225 nm; or Column Chiralpak® AD-H: 15:85 3A/C7 w/0.2% DMEA, 0.6 mL/min 225 nm.

EXAMPLE 71

(R)—N-(2-(1H-1,2,3-Triazol-1-yl)ethyl)-4-(7-(5-(1-aminoethyl)-2-fluoropyridin-4-yl)benzo[b]thiophen-2-yl)-5-fluoropyrimidin-2-amine

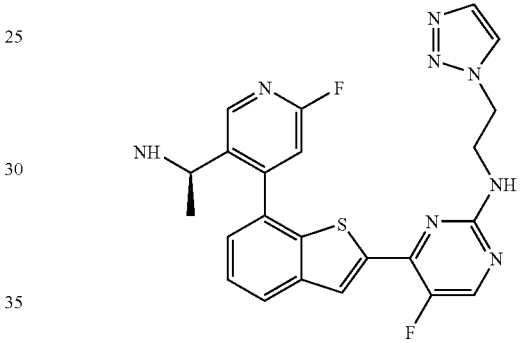

Separate 190 mg of racemic N-(2-(1H-1,2,3-triazol-1-yl)ethyl)-4-(7-(5-(1-aminoethyl)-2-fluoropyridin-4-yl)benzo[b]thiophen-2-yl)-5-fluoropyrimidin-2-amine with Column Chiralpak® AD-H using 0.2% DMEA in methanol at 1 ml/min. The (R) enantiomer elutes at 5.22 min? to give the title compound (0.4 mg, 21%). MS (ES) m/z 479 [M+1]+.

Separate the following examples from their racemates by utilizing a chromatographic method similar to that used for (R)-1-(4-(2-(2-(2-(1H-1,2,3-Triazol-1-yl)ethylamino)-5-fluoropyrimidin-4-yl)benzo[b]thiophen-7-yl)-6-fluoropyridin-3-yl)ethanol or (R)—N-(2-(1H-1,2,3-Triazol-1-yl)ethyl)-4-(7-(5-(1-aminoethyl)-2-fluoropyridin-4-yl)benzo[b]thiophen-2-yl)-5-fluoropyrimidin-2-amine:

| Ex | Compound structure | Compound Name | MS (ES) [M + 1]+ | Comments* |
|---|---|---|---|---|
| 72 | 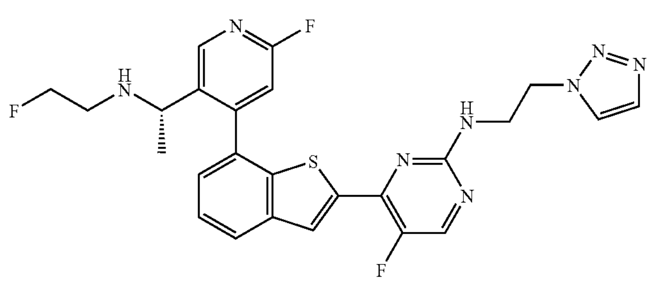 | (S)-N-(2-(1H-1,2,3-Triazol-1-yl)ethyl)-5-fluoro-4-(7-(2-fluoro-5-(1-(2-fluoroethyl-amino)ethyl)pyridin-4-yl)benzo[b]thiophen-2-yl)pyrimidin-2-amine | 525 | Chiralpak ® AD-H column |

-continued

| Ex | Compound structure | Compound Name | MS (ES) [M + 1]+ | Comments* |
|---|---|---|---|---|
| 73 | 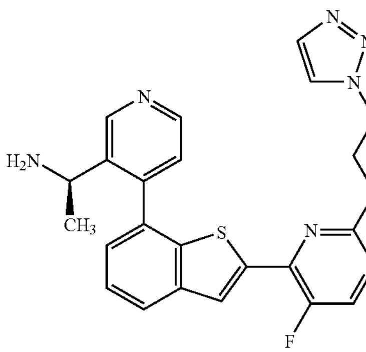 | (R)-N-(2-(1H-1,2,3-Triazol-1-yl)ethyl)-4-(7-(3-(1-aminoethyl)pyridin-4-yl)benzo[b]thiophen-2-yl)-5-fluoropyrimidin-2-amine | 461 | Chiralpak® AD-H |
| 74 | 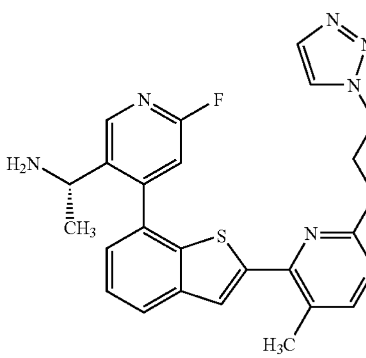 | (S)-N-(2-(1H-1,2,3-Triazol-1-yl)ethyl)-4-(7-(5-(1-aminoethyl)-2-fluoropyridin-4-yl)benzo[b]thiophen-2-yl)-5-methylpyrimidin-2-amine | 475 | Chiral OJ-H |
| 75 | 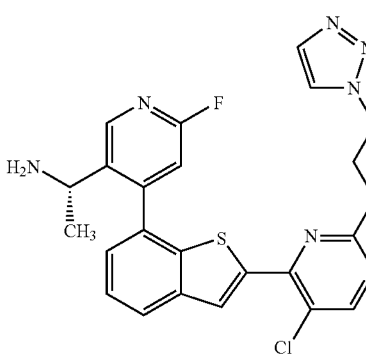 | (S)-N-(2-(1H-1,2,3-Triazol-1-yl)ethyl)-4-(7-(5-(1-aminoethyl)-2-fluoropyridin-4-yl)benzo[b]thiophen-2-yl)-5-chloropyrimidin-2-amine | 495 | Chiralpak® AS-H |
| 76 | 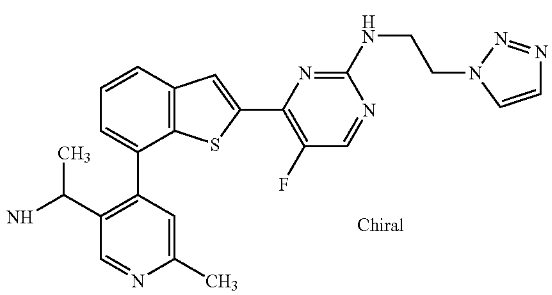 | N-(2-(1H-1,2,3-Triazol-1-yl)ethyl)-4-(7-(5-(1-aminoethyl)-2-methylpyridin-4-yl)benzo[b]thiophen-2-yl)-5 fluoropyrimidin-2-amine | 475 | Chiralpak® AS-H second fraction |

-continued

| Ex | Compound structure | Compound Name | MS (ES) [M + 1]+ | Comments* |
|---|---|---|---|---|
| 77 | 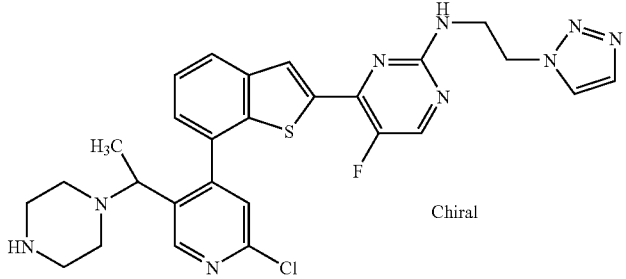 | N-(2-(1H-1,2,3-Triazol-1-yl)ethyl)-4-(7-(2-chloro-5-(1-(piperazin-1-yl)ethyl)pyridin-4-yl)benzo[b]thiophen-2-yl)-5-fluoropyrimidin-2-amine | 564 | Chiralpak ® AS-H, first fraction |
| 78 | 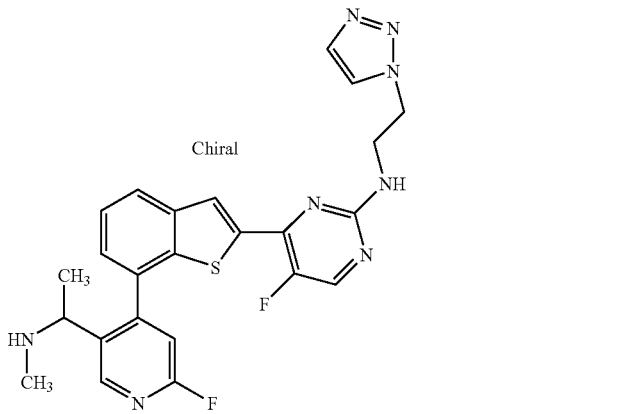 | (S)-N-(2-(1H-1,2,3-triazol-1-yl)ethyl)-5-fluoro-4-(7-(2-fluoro-5-(1-(methyl-amino)ethyl)pyridin-4-yl)benzo[b]thiophen-2-yl)pyrimidin-2-amine | 507 | Chiral OJ-H |
| 79 | 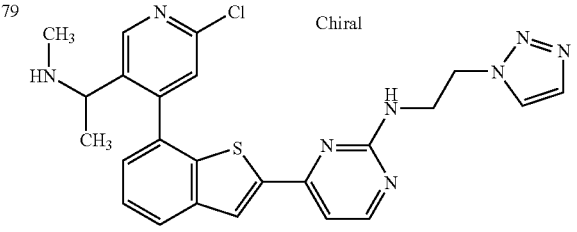 | N-(2-(1H-1,2,3-Triazol-1-yl)ethyl)-4-(7-(2-chloro-5-(1-(methylamino)-ethyl)pyridin-4-yl)benzo[b]thiophen-2-yl)pyrimidin-2-amine | 491 | Chiral OJ-H, first fraction |
| 80 | 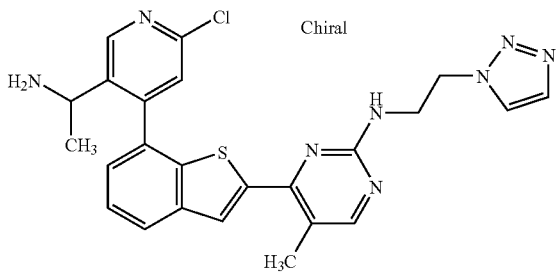 | N-(2-(1H-1,2,3-Triazol-1-yl)ethyl)-4-(7-(5-(1-aminoethyl)-2-chloropyridin-4-yl)benzo[b]thiophen-2-yl)-5-methylpyrimidin-2-amine | 492 | Chiral OJ-H, first fraction |

*The absolute configuration of some enantiomers in the table above are not determined. For instance, enantiomer Examples 76, 77, 79, and 80 are specified by retention time, e.g., first or second fraction off column.

EXAMPLE 81

(R)—N-(2-(1H-1,2,3-Triazol-1-yl)ethyl)-4-(7-(5-(1-aminoethyl)-2-fluoropyridin-4-yl)benzo[b]thiophen-2-yl)pyrimidin-2-amine

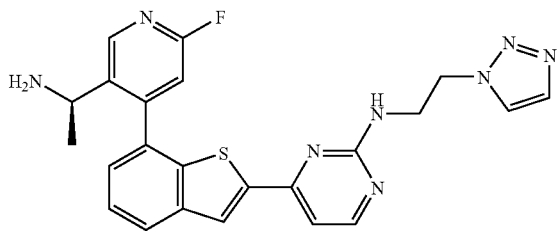

Add NH$_2$NH$_2$—HCOOH (Pre-prepared, 1 mL) to a solution of (R)—N-(2-(1H-1,2,3-triazol-1-yl)ethyl)-4-(7-(5-(1-azidoethyl)-2-fluoropyridin-4-yl)benzo[b]thiophen-2-yl)pyrimidin-2-amine (250 mg, 513.84 μmol) in ethanol (10 mL). Cool the mixture to 0° C. and add Raney Nickel (0.5 g, 8.52 mmol, wet with water as it packed). Stir the solution at RT for another 1.5 h, filter Raney Nickel out, and wash with methanol. Dilute filtrate with chloroform/IPA (3/1) and wash with saturated sodium carbonate. Dry the organic phase over sodium sulfate and concentrate in vacuo to give a brown tar. Purify the solid by passing through a FCC (10% methanol in DCM) to give the title compound as a pale brown solid (200 mg, 85%). MS (ES) m/z 461 [M+1]$^+$.

EXAMPLE 82

(R)—N-(2-(1H-1,2,3-Triazol-1-yl)ethyl)-4-(7-(5-(1-(dimethylamino)ethyl)-2-fluoropyridin-4-yl)benzo[b]thiophen-2-yl)-5-fluoropyrimidin-2-amine

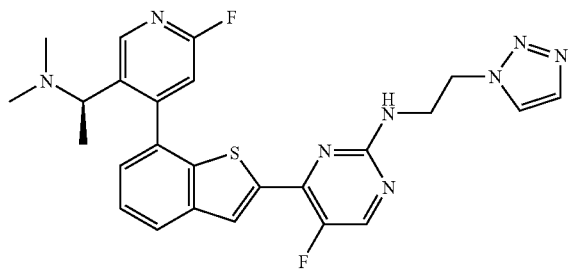

Charge (R)—N-(2-(1H-1,2,3-triazol-1-yl)ethyl)-4-(7-(5-(1-aminoethyl)-2-fluoropyridin-4-yl)benzo[b]thiophen-2-yl)-5-fluoropyrimidin-2-amine (120 mg, 251 μmol), paraformaldehyde (1.45 g, 4.11 mmol), and acetic acid (15 mg, 251 μmol) into 1,4-dioxane (5 mL) in a 50 mL round bottom flask. Stir the mixture at RT for 10 min and add sodium tetrahydroborate (37.95 mg, 1 mmol). Stir the resulting mixture at RT for 3 h, dilute with chloroform, wash with diluted ammonium hydroxide, and concentrate in vacuo. Purify the crude by FCC (10% methanol in DCM) to give the title compound as a yellow solid (34 mg, 27%). (ES) m/z 507 [M+1]$^+$.

EXAMPLE 83

N-(2-(1H-1,2,3-Triazol-1-yl)ethyl)-4-(7-(5-(2-aminoethoxy)-2-fluoropyridin-4-yl)benzo[b]thiophen-2-yl)-5-fluoropyrimidin-2-amine

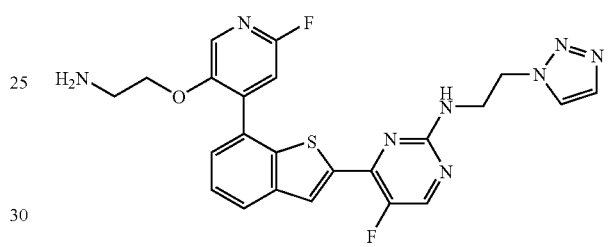

Add hydrazine (0.03 mL, 0.8 mmol) to a solution of 2-(2-(4-(2-(2-(2-(1H-1,2,3-triazol-1-yl)ethylamino)-5-fluoropyrimidin-4-yl)benzo[b]thiophen-7-yl)-6-fluoropyridin-3-yloxy)ethyl)isoindoline-1,3-dione (0.25 g, 0.4 mmol) in ethanol (5 mL). Stir the mixture at 40° C. overnight. Remove the solvent and purify the residue by column chromatography (10% methanol in DCM) to afford the title compound (70 mg, 35%). MS (ES) m/z 495 [M+1]$^+$.

Prepare the following examples with procedures similar to those described for N-(2-(1H-1,2,3-Triazol-1-yl)ethyl)-4-(7-(5-(2-aminoethoxy)-2-fluoropyridin-4-yl)benzo[b]thiophen-2-yl)-5-fluoropyrimidin-2-amine:

| Ex | Compound structure | Compound Name | MS (ES) [M + 1]$^+$ |
|---|---|---|---|
| 84 | 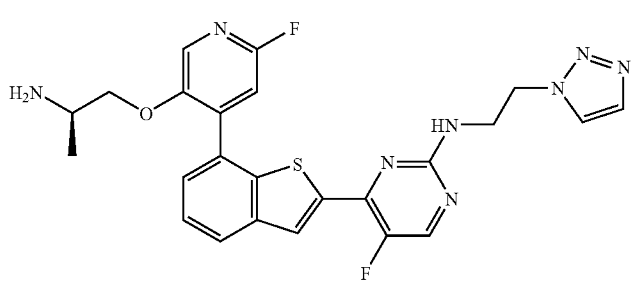 | (R)-N-(2-(1H-1,2,3-Triazol-1-yl)ethyl)-4-(7-(5-(2-aminopropoxy)-2-fluoropyridin-4-yl)benzo[b]thiophen-2-yl)-5-fluoropyrimidin-2-amine | 509 |

| Ex | Compound structure | Compound Name | MS (ES) [M + 1]+ |
|---|---|---|---|
| 85 | 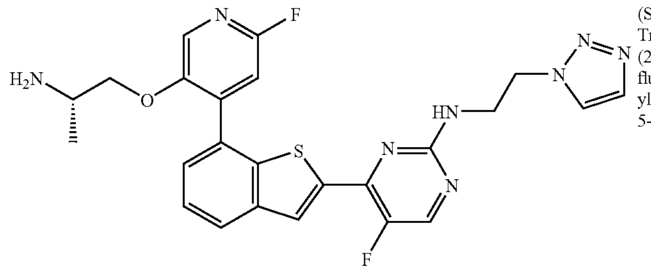 | (S)-N-(2-(1H-1,2,3-Triazol-1-yl)ethyl)-4-(7-(5-(2-aminopropoxy)-2-fluoropyridin-4-yl)benzo[b]thiophen-2-yl)-5-fluoropyrimidin-2-amine | 509 |

Plk1 has been shown to be over expressed in many human tumors, such as non-small cell lung, oropharyngeal, esophageal, gastric, melanoma, breast, ovarian, endometrial, colorectal, glioblastoma, papillary, pancreatic, prostate, hepatoblastoma and non-Hodgkin lymphoma cancers. Furthermore, Plk1 expression has prognostic significance in non-small cell lung, oropharyngeal, esophageal, melanoma, colorectal, hepatoblastoma and non-Hodgkin lymphoma cancers [Strebhardt, K. and A. Ullrich. *Nature Reviews Cancer* 6(4): 321-30 (2006)]. Plk1 phosphorylated substrates regulate progression of mitosis by coordinating centrosome maturation, entry into mitosis, sister chromatid separation and cytokinesis [Eckerdt F. Strebhardt K. Cancer Research. 66(14):6895-8, 2006; Strebhardt and Ullrich 2006; van de Weerdt, B. C. and R. H. Medema. *Cell Cycle* 5(8): 853-64 (2006)]. Inhibiting Plk1 function using antibody injection, expression of a dominant negative Plk1, and antisense mRNA reduction produces monopole spindles and anaphase arrest leading to mitotic cell death in tumor cell lines but reversible G2 arrest in normal non-transformed primary cell lines.

Additionally, it has been reported that Plk may be useful in the treatment of rhabdoid tumors, (Morozov A., et al., Clinical Cancer Research 13(16):4721-30, (Aug. 15, 2007).

BI-2536 has demonstrated activity in preclinical models using HCT116, A549 and NCIH460 murine xenografts (Baum, A., P. Garin-Chesa, et al. (2006). #C191 *In vivo activity of BI 2536, a potent and selective inhibitor of the mitotic kinase PLK1, in a range of cancer xenografts.* AACR-NCI-EORTC International Conference on "Molecular Targets and Cancer Therapeutics", Philadelphia, Pa.).

The results of the following assays demonstrate evidence that the compounds of the present invention are useful as anticancer agents. Certain of the example compounds described herein are racemic mixtures. These compounds are tested as racemic mixtures and/or as individual enantiomers. At least one enantiomer or the racemate met the assay criterion below.

Expression and Purification of Plk1

Human Plk1 cDNA may be directly linked at one of its termini with a polynucleotide sequence expressing a His$_6$ tag, such as the C-terminal FLAG-His$_6$ tag, and inserted into an appropriate expression vector, such as a pFastBac™ vector (Invitrogen) and transfected into an appropriate system, such as baculovirus similar to what has been reported by Yue-Wei Qian, et al., Science, 282, 1701 (1998) for xPlk1. If a viral expression system is used, then the virus (e.g., baculovirus bearing a Plk1-Flag-His$_6$ tag polynucleotide construct) is infected into a culture of a suitable host cell, such as Sf9 cells. When sufficient amounts of the Plk1-Flag-His$_6$ tag fusion protein have been expressed, for example, at about 46 hours after infection, the culture should be treated with okadaic acid (0.1 µM) for a sufficient period of time (e.g., 3 hours). The Plk1-Flag-His$_6$ tag fusion is purified from cell pellets using a metal affinity resin, such as TALON™ using methods well known in the art. Purified Plk1-Flag-His$_6$ tag fusion is stored in a suitable medium, such as 10 mM HEPES, 150 mM NaCl, 0.01% TRITON® X-100, 1 mM dithiothreitol (DTT), 10% glycerol, pH 7.5, at −80° C. in small aliquots until use. The identity of the purified Plk1-Flag-His$_6$ tag fusion protein is confirmed by MALDI (Matrix-Assisted Laser Desorption/Ionization).

Expression and Purification of GST-Cdc25C(1-206)

Human Cdc25C cDNA, which may be obtained from any appropriate source, may be expressed in any convenient expression system, after which purification is effected by well known methods similar to that described by Bin Ouyang et al, Oncogene, 18, 6029-6036 (1999). One convenient system involves overnight growth at 18° C. of *E. coli* BL21 transformed with the pGEX-2T vector (Amersham) into which the cDNA for human Cds25C has been engineered for induced expression using 1 mM isopropyl-beta-D-thiogalactopyranoside. The expressed GST-Cdc25C(1-206), the substrate for Plk1, may be purified (for example, by GLUTATHIONE SEPHAROSE® 4B) and stored in an appropriate solution, such as 10 mM HEPES, 100 mM NaCl, pH 7.5 in small aliquots at −80° C.

Plk1 Inhibition Assay

Plk1 kinase reactions contain Plk1-Flag-His$_6$ tag fusion enzyme (0.2 ng/µL) in a buffer containing 50 mM HEPES, pH 7.3, 1.0 mM dithiothreitol, 5.0 µM ATP, 10 mM MgCl$_2$, 0.01% TRITON® X-100, 0.4 µCi $^{33}$P-ATP, and 0.06 µg/µL GST-Cdc25c (1-206) peptide. Compounds are provided as 10 mM stocks in DMSO. Compounds are serially diluted 1:3 in 20% DMSO to create a 10-point concentration-response curve and subsequently are diluted 1:5 (20 µM to 0.001 µM final in 4% final DMSO concentration) in the reaction mixture to determine compound activity. The reaction is carried out at RT for 60 min and then quenched by adding 60 µL of 10.0% H$_3$PO$_4$. The reaction mixture (85 µL) is transferred to a 96 well phosphocellulose filter plate pre-wetted with 30 µL of 10.0% H$_3$PO$_4$, incubated at RT for 20-30 min and then washed 3× with 0.5% H$_3$PO$_4$. Wells are dried before addition of 40 µL of MicroScintTM20 (Packard) and then counted on a Wallac MICROBETA® Jet. The percentage inhibition values from the 10-point concentration response data are subsequently analyzed, for example, using ACTIVITY BASE™ software (IDBS), using a 4-parameter logistic equation. Absolute IC$_{50}$ values are calculated from the resulting curve fit. All exemplified compounds have an IC$_{50}$ less than 100 nM with a Minimum Significant Ratio (MSR) for the IC$_{50}$ of 3.6, with the caveat that either the racemic mixture and/or at least one enantiomer had an IC$_{50}$ less than 100 nM. For example, Example 41 racemate has an $IC_{50}$ of 12 nM. This demonstrates that the compounds of the present invention are potent inhibitors of Plk1.

pHH3(S10), Mitotic Cells, and DNA Content Assays

HeLa Cells are plated at 200 cells/well in 96 well Beckman Dickinson BIOCOAT™ plates, and are incubated in MEM (Minimum Essential Medium) with 10% FBS (Fetal Bovine Serum) in 37° C., 5% $CO_2$ for 24 hours. Cells are treated by adding compound (in 0.25% DMSO) to the medium, dosing at 10 points across the range 0.5 µM to 0.0098 µM. After 23 hours exposure to the compounds, cells are fixed, for example with the PREFER™ fixative for 30 min then are permeabilized with 0.1% TRITON® X100 in phosphate buffered saline (PBS) solution for 15 min. Cells are washed 3 times with PBS then digested with 50 µg/mL RNAse. Primary antibody, phosphohistone H3, is added at 1:500 in PBS with 1% bovine serum albumin (BSA) to the cells over night at 4° C. After 3 PBS washes, cells are incubated with Alexa488 labeled secondary antibody for 1 hour at RT. Again they are washed 3 times with PBS, and then 15 µM propidium iodide is added for 30 min to stain nuclei. Fluorescence Plates are scanned with ACUMEN EXPLORER™ [Laser-scanning fluorescence microplate cytometer (comprising of 488 nm argon ion laser excitation and multiple photomultiplier tube detection), manufactured by TTP LABTECH LTD] to measure anti-phosphohistone H3 Serine 10, DNA content and mitotic cells as measured by DNA condensation. Image analysis are based on cellular fluorescent signals for identifying cells in different subpopulations. pHH3(S10) positive cells are identified by mean intensity at 500-530 nm above the threshold. Total intensity at 655-705 nm from propidium iodide/DNA is used to identify individual cells (cells with DNA content from 2N to 4N) and subpopulations in cell cycle (2N cells, 4N cells). Peak intensity at 575-640 nm is used to identify DNA condensation that is used as the marker to identify mitotic cells among 4N cells. Assay outputs are percentage of each identified subpopulations, % pHH3, % 2N, % 4N, % mitotic and total cell number. The $EC_{50}$ is determined by curve fitting to a four parameter logistic for each output using ACTIVITY BASE™. The resulting $EC_{50s}$ for pHH3 (s10), DNA content, and mitotic have an MSR of 2.6, 2.4 and 2.5, respectively. For example, Example 41 racemate has an pHH3(s10) $EC_{50}=25$ nM, DNA content $EC_{50}=30$ nM and mitotic $EC_{50}=23$ nM.

Antiproliferative Assay

The effects of compounds on cell proliferation can be determined using cells and cell proliferation methods well-known in the art (Robert C. Squatrito et al., Gynecological Oncology, 58, 101-105, (1995)). For example, HCT116 cells, which may be obtained from the American Type Culture Collection, may be seeded at ~2000 cells/well in 96-well plates and allowed to attach overnight in a humidified $CO_2$ incubator at 37° C. Following the 20-24 hour incubation, half-log serially diluted compounds are added and the plates are returned to the incubator. After an appropriate length of exposure (e.g., 72 hours), cell proliferation is estimated using well-known methods. In one method, 10 µL of a tetrazolium salt, such as Alamar Blue™ is added to the cell plates. After an appropriate exposure to the dye, fluorescence (530 nm excitation, 580 nm emission) is determined. The resulting $IC_{50}$ has an MSR of 3.1. For example, Example 41 racemate has an average $IC_{50}=31$ nM (n=2). This demonstrates that the compounds of the present invention are useful in treating proliferative disorders, including types of cancer.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (A. Gennaro, et al., eds., $19^{th}$ ed., Mack Publishing Co., 1995).

The compounds of Formula I are generally effective over a wide dosage range. For example, dosages per day normally fall within the range of about 1 to about 10 mg/kg of body weight, preferably 2 to 6.5 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:
1. A compound of the formula:

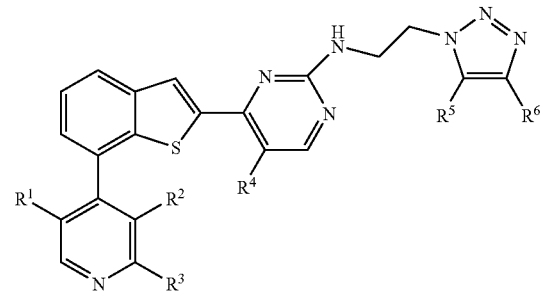

wherein:
R¹ is hydrogen, methyl, cyclopropyl, cyclopropylamino ($C_1$-$C_2$ alkyl), fluoro, ethoxy, hydroxy, 1-(hydroxy)ethyl, 2-(hydroxy)($C_2$-$C_3$ alkoxy), 2-(hydroxy)ethoxymethyl, 1-(chloro)ethyl, 1-((2-fluoro)ethylamino)ethyl, 2-(methylamino)ethoxy, (2-hydroxyethyl)amino, (2-hydroxyethyl)amino($C_1$-$C_2$ alkyl), amino, amino($C_1$-$C_4$ alkyl), amino($C_2$-$C_3$ alkoxy), aminocarbonylmethyl, (1-methyl)-(1-aminocarbonyl)ethyl, ($C_1$-$C_3$ alkyl)amino($C_1$-$C_2$ alkyl), methoxyethylamino, N—($C_1$-$C_3$ alkyl)-N-methylamino($C_1$-$C_2$ alkyl), pyrrolidin-1-yl-methyl, 3-(dimethylamino)-pyrrolidin-1-yl-methyl, 3-(pyrid-3-yl)-pyrrolidin-1-yl-methyl, 3-(amino)pyrrolidin-1-yl-methyl, 3-(methylamino)pyrrolidin-1-yl-methyl, (4,4-dimethyloxalidin-3-yl)methyl, [N-(2-hydroxy)ethyl-N-methyl]-aminomethyl, (azetidin-1-yl)methyl, piperidin-1-yl-methyl, 4-(methoxy)piperidin-1-yl-methyl, 4-(hydroxy)piperidin-1-yl-methyl, 4-(hydroxymethyl)piperidin-1-yl-methyl, piperazin-1-yl-($C_1$-$C_2$ alkyl), 4-(methyl)piperazin-1-yl-methyl, 3,5-(dimethyl)piperazin-1-yl-methyl, or morpholin-4-yl-methyl;
R² is hydrogen;
R³ is hydrogen, methyl, fluoro, or chloro, or R³ is amino and together with R² forms a pyrrolyl ring fused to the pyridine;
R⁴ is hydrogen, methyl, fluoro, or chloro;
R⁵ is hydrogen or hydroxymethyl; and
R⁶ is hydrogen or methyl; or
a pharmaceutically acceptable salt thereof.
2. The compound according to claim 1 wherein:
R¹ is cyclopropylamino($C_1$-$C_2$ alkyl), 1-(hydroxy)ethyl, 2-(hydroxy)ethoxymethyl, 1-(chloro)ethyl, 1-((2-fluoro)ethylamino)ethyl, (2-hydroxyethyl)amino, (2-hydroxyethyl)amino($C_1$-$C_2$ alkyl), amino($C_1$-$C_4$ alkyl), aminocarbonylmethyl, (1-methyl)-(1-aminocarbonyl)ethyl, ($C_1$-$C_3$ alkyl)amino($C_1$-$C_2$ alkyl), N—($C_1$-$C_3$ alkyl)-N-methyl-amino($C_1$-$C_2$ alkyl), pyrrolidin-1-yl-methyl, 3-(dimethylamino)pyrrolidin-1-yl-methyl, 3-(pyrid-3-yl)-pyrrolidin-1-yl-methyl, 3-(amino)pyrrolidin-1-yl-methyl, 3-(methylamino)pyrrolidin-1-yl-methyl, (4,4-dimethyloxalidin-3-yl)methyl, [N-(2-hydroxy)ethyl-N-methyl]-aminomethyl, (azetidin-1-yl)methyl, piperidin-1-yl-methyl, 4-(methoxy)piperidin-1-yl-methyl, 4-(hydroxy)piperidin-1-yl-methyl, 4-(hydroxymethyl)piperidin-1-yl-methyl, piperazin-1-yl-($C_1$-$C_2$ alkyl), 4-(methyl)piperazin-1-yl-methyl, 3,5-(dimethyl)piperazin-1-yl-methyl, or morpholin-4-yl-methyl; or a pharmaceutically acceptable salt thereof.

3. The compound according to claim 1 wherein:
$R^1$ is amino($C_1$-$C_4$ alkyl), ($C_1$-$C_3$ alkyl)amino($C_1$-$C_2$ alkyl), N—($C_1$-$C_3$ alkyl)-N-methyl-amino($C_1$-$C_2$ alkyl), or morpholin-4-yl-methyl; or a pharmaceutically acceptable salt thereof.

4. The compound according to claim 1 wherein:
$R^1$ is amino($C_1$-$C_4$ alkyl), or ($C_1$-$C_3$ alkyl)amino($C_1$-$C_2$ alkyl);
$R^3$ is hydrogen or fluoro;
$R^4$ is hydrogen or fluoro;
$R^5$ is hydrogen; and
$R^6$ is hydrogen; or a pharmaceutically acceptable salt thereof.

5. The compound according to claim 1 wherein $R^1$ is 1-(methylamino)ethyl, $R^3$ is fluoro and $R^4$ is hydrogen, $R^5$ is hydrogen, and $R^6$ is hydrogen, or a pharmaceutically acceptable salt thereof.

6. The compound according to claim 1 wherein $R^1$ is 1-aminoethyl, $R^3$ is fluoro and $R^4$ is fluoro, $R^5$ is hydrogen, and $R^6$ is hydrogen, or a pharmaceutically acceptable salt thereof.

7. The compound according to claim 1 wherein $R^1$ is 1-aminoethyl, $R^3$ is fluoro and $R^4$ is hydrogen, $R^5$ is hydrogen, and $R^6$ is hydrogen, or a pharmaceutically acceptable salt thereof.

8. The compound according to claim 1 wherein $R^1$ is 1-(methylamino)ethyl, $R^3$ is fluoro and $R^4$ is fluoro, $R^5$ is hydrogen, and $R^6$ is hydrogen, or a pharmaceutically acceptable salt thereof.

9. A pharmaceutical composition comprising a compound of claim 1 or a pharmaceutically acceptable salt thereof, in combination with a pharmaceutically acceptable carrier, diluent or excipient.

* * * * *